(12) United States Patent
Yodfat et al.

(10) Patent No.: US 9,248,232 B2
(45) Date of Patent: Feb. 2, 2016

(54) ANALYTE MONITORING AND FLUID DISPENSING SYSTEM

(75) Inventors: Ofer Yodfat, Modi'in (IL); Eli Znati, Kiriat Shmona (IL); Illai Gescheit, Tel-Aviv (IL); Avraham Neta, Gilon (IL); Offer Levy, Modi'in (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 507 days.

(21) Appl. No.: 13/511,578

(22) PCT Filed: Nov. 30, 2010

(86) PCT No.: PCT/IL2010/000997
§ 371 (c)(1),
(2), (4) Date: Jun. 15, 2012

(87) PCT Pub. No.: WO2011/064780
PCT Pub. Date: Jun. 3, 2011

(65) Prior Publication Data
US 2012/0277667 A1  Nov. 1, 2012

Related U.S. Application Data

(60) Provisional application No. 61/264,840, filed on Nov. 30, 2009.

(51) Int. Cl.
*A61M 31/00* (2006.01)
*A61M 5/168* (2006.01)
(Continued)

(52) U.S. Cl.
CPC .......... *A61M 5/14248* (2013.01); *A61B 5/1451* (2013.01); *A61B 5/14532* (2013.01); *A61B 5/14865* (2013.01); *A61M 5/1413* (2013.01);
(Continued)

(58) Field of Classification Search
CPC .......... A61M 5/14248; A61M 5/1413; A61M 2005/14268; A61B 5/4839
USPC ................................ 604/65–67; 600/300, 309
See application file for complete search history.

(56) References Cited

U.S. PATENT DOCUMENTS 3,771,694 A   11/1973   Kaminski
4,498,843 A   2/1985   Schneider et al.
(Continued)

FOREIGN PATENT DOCUMENTS

WO   WO-2007052277 A1   5/2007
WO   WO 2008038274   *   4/2008
(Continued)

OTHER PUBLICATIONS

Tamada, et al., "Noninvasive glucose monitoring: comprehensive clinical results," *JAMA*(1999) 282:1839-1844.
(Continued)

*Primary Examiner* — Matthew F Desanto
(74) *Attorney, Agent, or Firm* — Dinsmore & Shohl LLP

(57) ABSTRACT

Embodiments of the present disclosure are directed to a skin adherable device for delivering therapeutic fluid into a body of a patient. In some embodiments, the device includes a monitoring apparatus, a pump, and a tip for delivering the therapeutic fluid into the body of the patient and for monitoring bodily analyte in the body of the patient. The pump may continuously deliver the therapeutic fluid to the body of the patient and the monitoring apparatus may continuously monitor bodily analytes of the patient.

20 Claims, 54 Drawing Sheets

(51) Int. Cl.

| | | |
|---|---|---|
| A61M 5/142 | (2006.01) | |
| A61B 5/145 | (2006.01) | |
| A61B 5/1486 | (2006.01) | |
| A61M 5/14 | (2006.01) | |
| A61M 5/145 | (2006.01) | |
| A61M 5/172 | (2006.01) | |
| A61B 5/00 | (2006.01) | |
| A61M 5/00 | (2006.01) | |

(52) U.S. Cl.
CPC ........... *A61M 5/1456* (2013.01); *A61M 5/1723* (2013.01); *A61B 5/4839* (2013.01); *A61M 5/002* (2013.01); *A61M 2005/14252* (2013.01); *A61M 2005/14268* (2013.01); *A61M 2005/1726* (2013.01); *A61M 2205/3317* (2013.01); *A61M 2205/3569* (2013.01); *A61M 2205/3592* (2013.01); *A61M 2209/01* (2013.01); *A61M 2230/201* (2013.01)

(56) References Cited

U.S. PATENT DOCUMENTS

| | | | |
|---|---|---|---|
| 4,657,486 | A | 4/1987 | Stempfle et al. |
| 5,957,895 | A | 9/1999 | Sage et al. |
| 6,091,976 | A | 7/2000 | Pfeiffer et al. |
| 6,129,527 | A | 10/2000 | Donahoe et al. |
| 6,139,527 | A | 10/2000 | Laufer et al. |
| 6,360,888 | B1 | 3/2002 | McIvor et al. |
| 6,391,643 | B1 | 5/2002 | Chen et al. |
| 6,485,461 | B1 | 11/2002 | Mason et al. |
| 6,558,351 | B1 | 5/2003 | Steil et al. |
| 6,589,229 | B1 | 7/2003 | Connelly et al. |
| 6,723,072 | B2 | 4/2004 | Flaherty et al. |
| 6,740,059 | B2 | 5/2004 | Flaherty |
| 6,881,551 | B2 | 4/2005 | Heller et al. |
| 6,892,085 | B2 | 5/2005 | McIvor et al. |
| 2005/0043682 | A1 | 2/2005 | Kucklick et al. |
| 2005/0165288 | A1 | 7/2005 | Rioux et al. |
| 2006/0012774 | A1 | 1/2006 | O'Mahony et al. |
| 2007/0076474 | A1 | 4/2007 | Fujisawa |
| 2007/0106218 | A1 | 5/2007 | Yodfat et al. |
| 2007/0191702 | A1 | 8/2007 | Yodfat et al. |
| 2007/0219597 | A1* | 9/2007 | Kamen et al. ............ 607/60 |
| 2008/0214916 | A1* | 9/2008 | Yodfat et al. ............ 600/347 |
| 2008/0215035 | A1* | 9/2008 | Yodfat et al. ............ 604/513 |
| 2008/0319414 | A1 | 12/2008 | Yodfat et al. |
| 2009/0131769 | A1* | 5/2009 | Leach et al. ............ 600/309 |
| 2009/0292189 | A1 | 11/2009 | Say et al. |

FOREIGN PATENT DOCUMENTS

| | | |
|---|---|---|
| WO | WO-2008038274 A1 | 4/2008 |
| WO | WO-2008078318 A2 | 7/2008 |
| WO | WO-2008078319 A1 | 7/2008 |
| WO | WO-2009001346 A1 | 12/2008 |
| WO | WO-2009013736 A1 | 1/2009 |
| WO | WO-2009016636 A2 | 2/2009 |
| WO | WO-2009060432 A1 | 5/2009 |
| WO | WO-2009125398 A2 | 10/2009 |

OTHER PUBLICATIONS

Maran, et al., "Continuous subcutaneous glucose monitoring in diabetic patients: a multi-center analysis," Diabetes Care (2002) 25: 347-352.

Hoogma, et al., "Comparison of the effects of continuous subcutaneous insulin infusion (CSII) and NPH-based multiple daily insulin injections (MDI) on glycaemic control and quality of life: results of the 5-nations trial," Diabet Med (2006) 23(2):141-7.

Boizel, et al., "Glucose monitoring and pump data management software operated on a personal digital assistant can contribute to improve diabetes control in CSII-treated patients," *Diabetes Metab.* (2007) 33:314-315.

Parkner, et al., "Overnight CSII as supplement to oral antidiabetic drugs in Type 2 diabetes," *Diabetes Obes. Metab.* (2007) 10:556-563.

International Search Report for International Application No. PCT/IL 10/00997, date of mailing: Jun. 3, 2011.

* cited by examiner

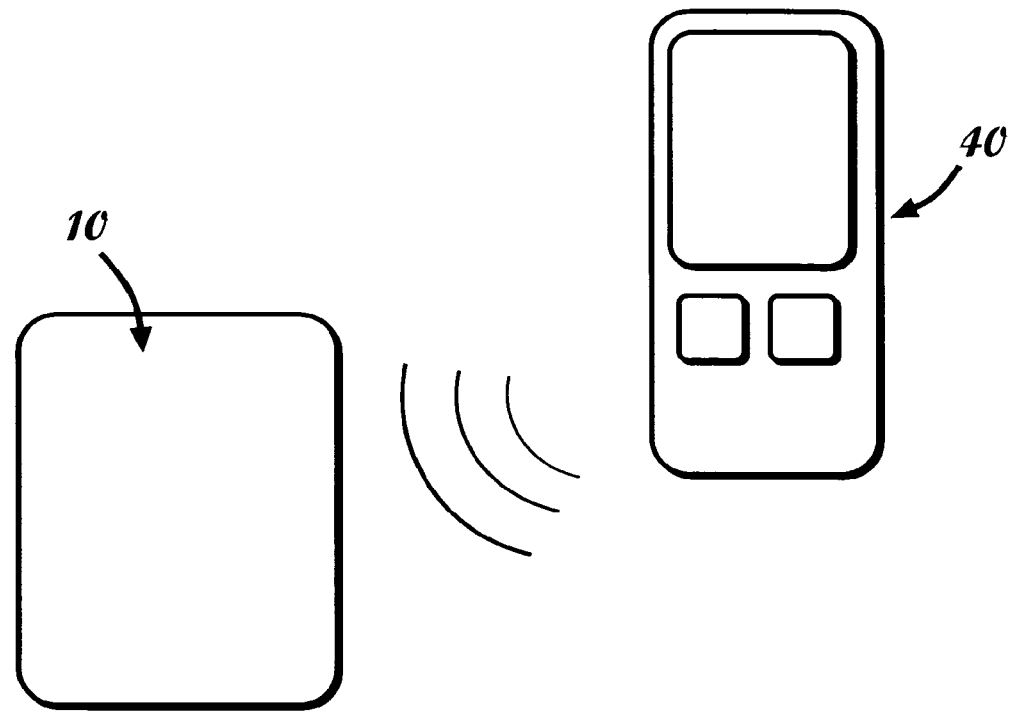
Fig. 1a
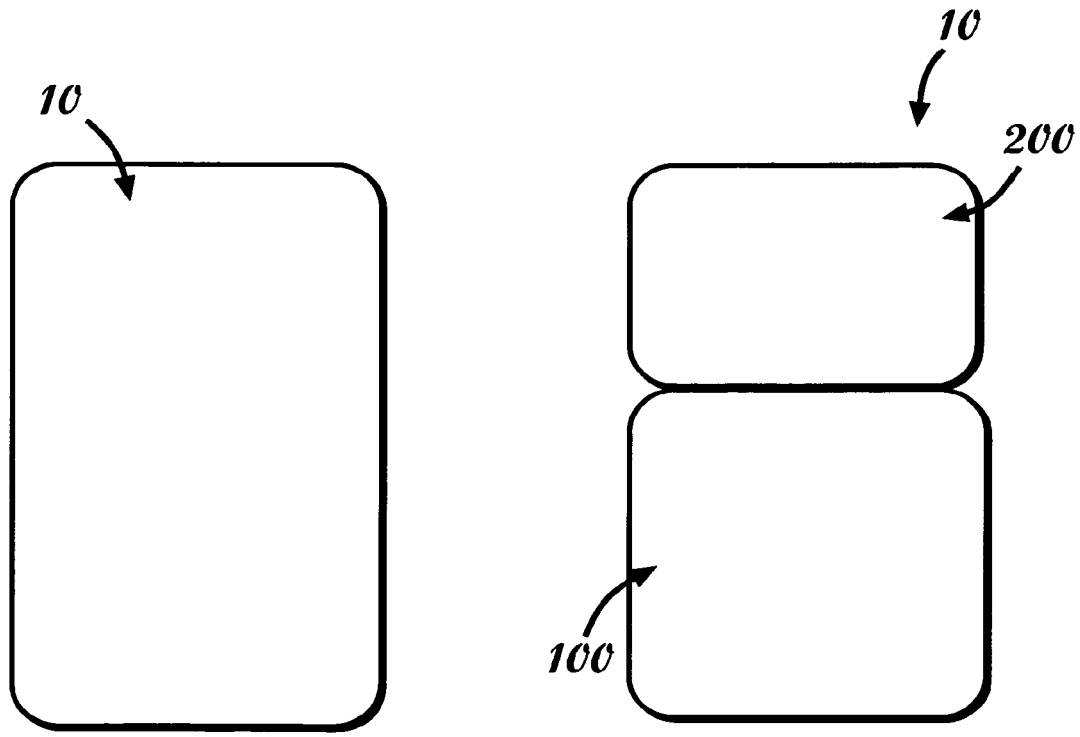
Fig. 1b  Fig. 1c

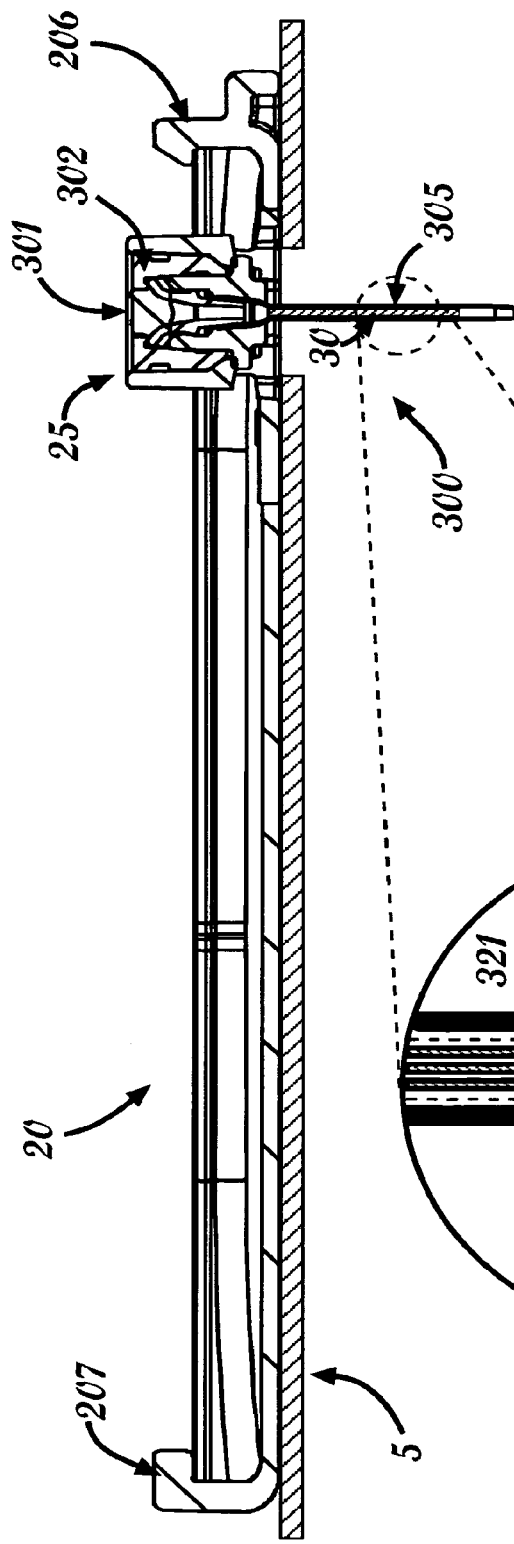
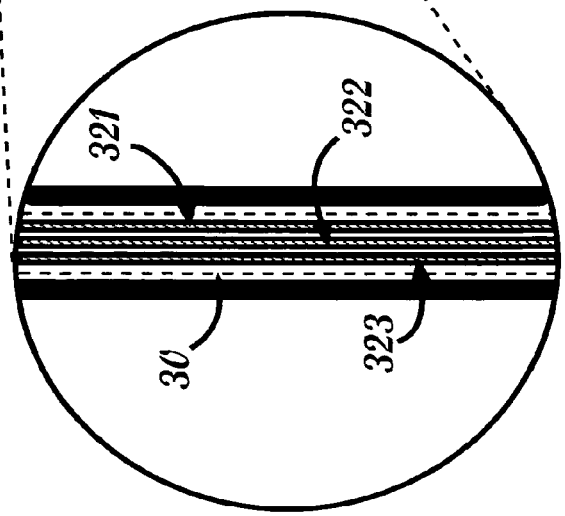
Fig. 6a
Fig. 6b

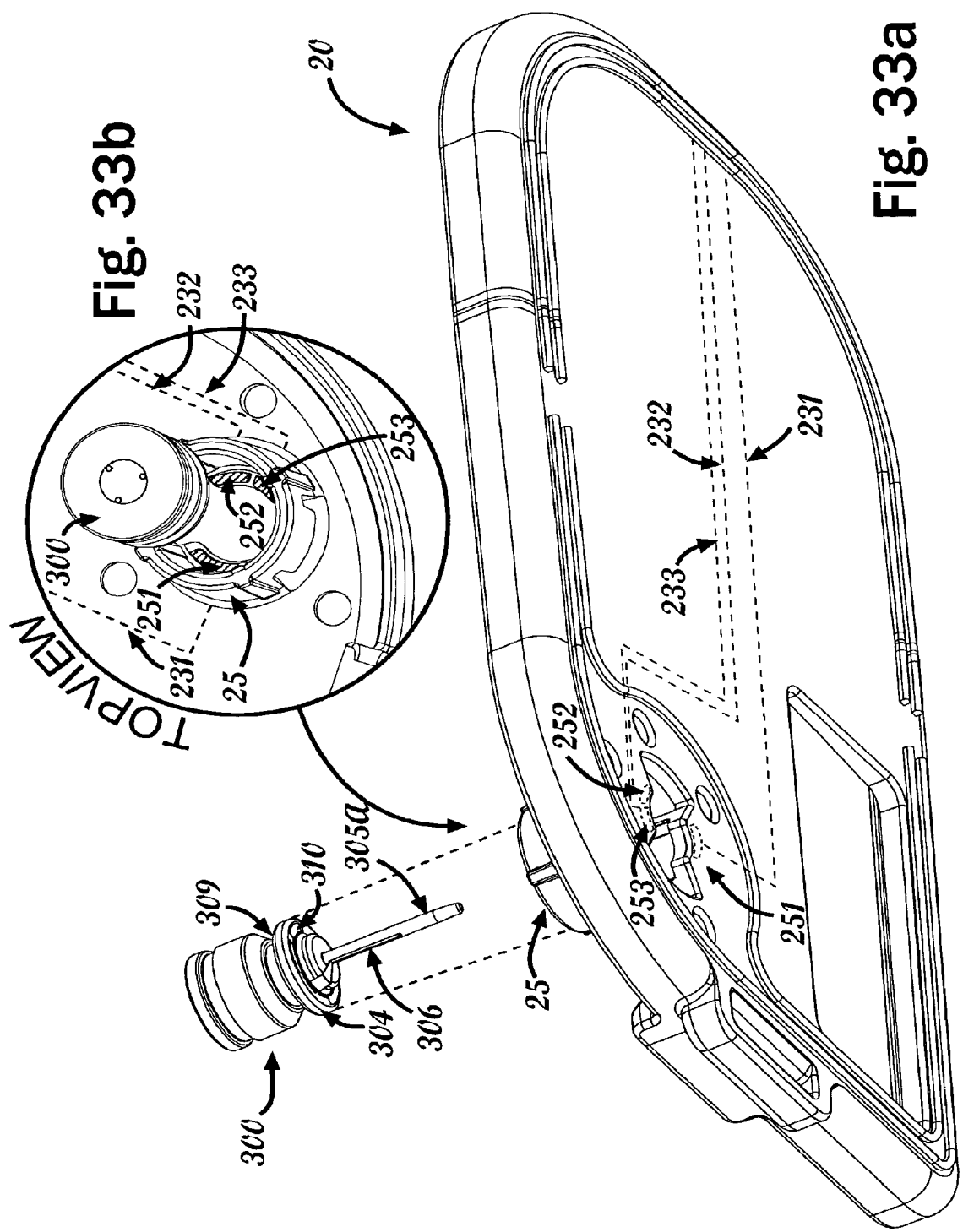

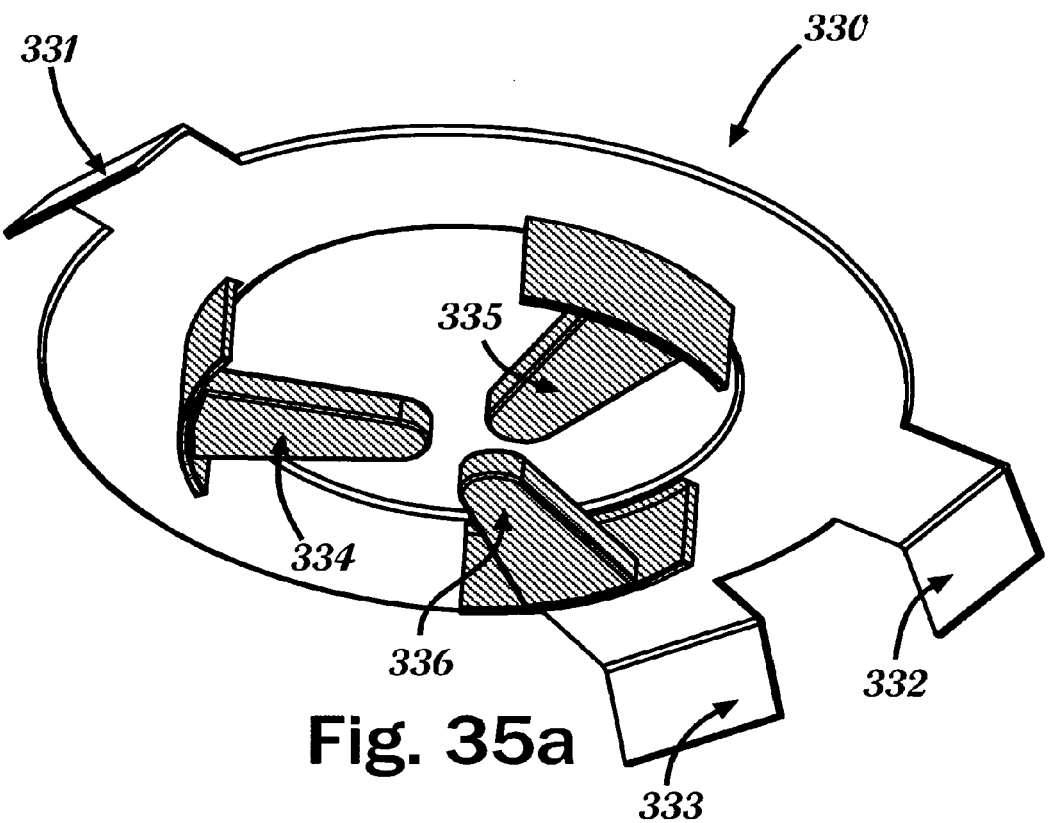
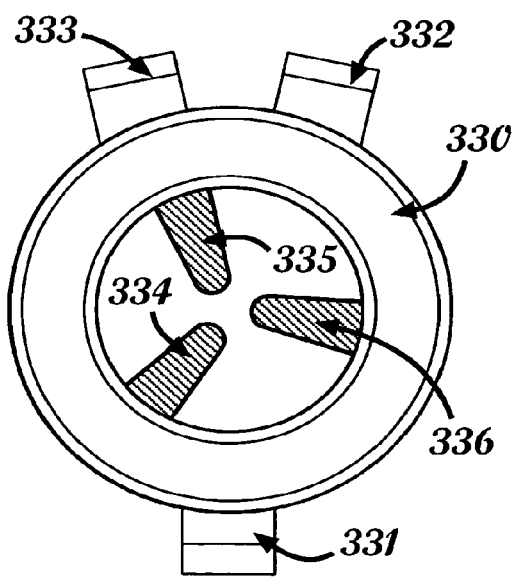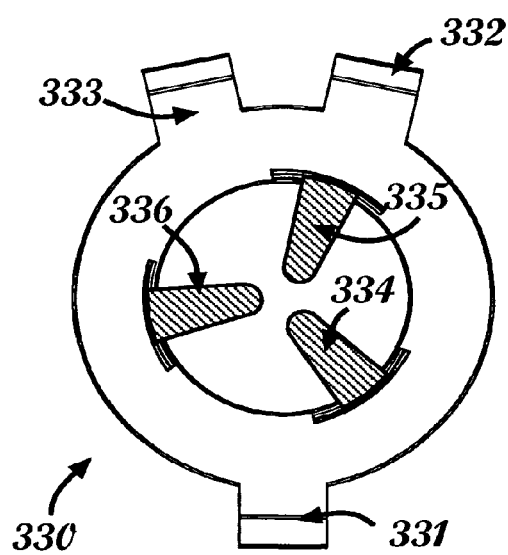
Fig. 35a
Fig. 35b
Fig. 35c

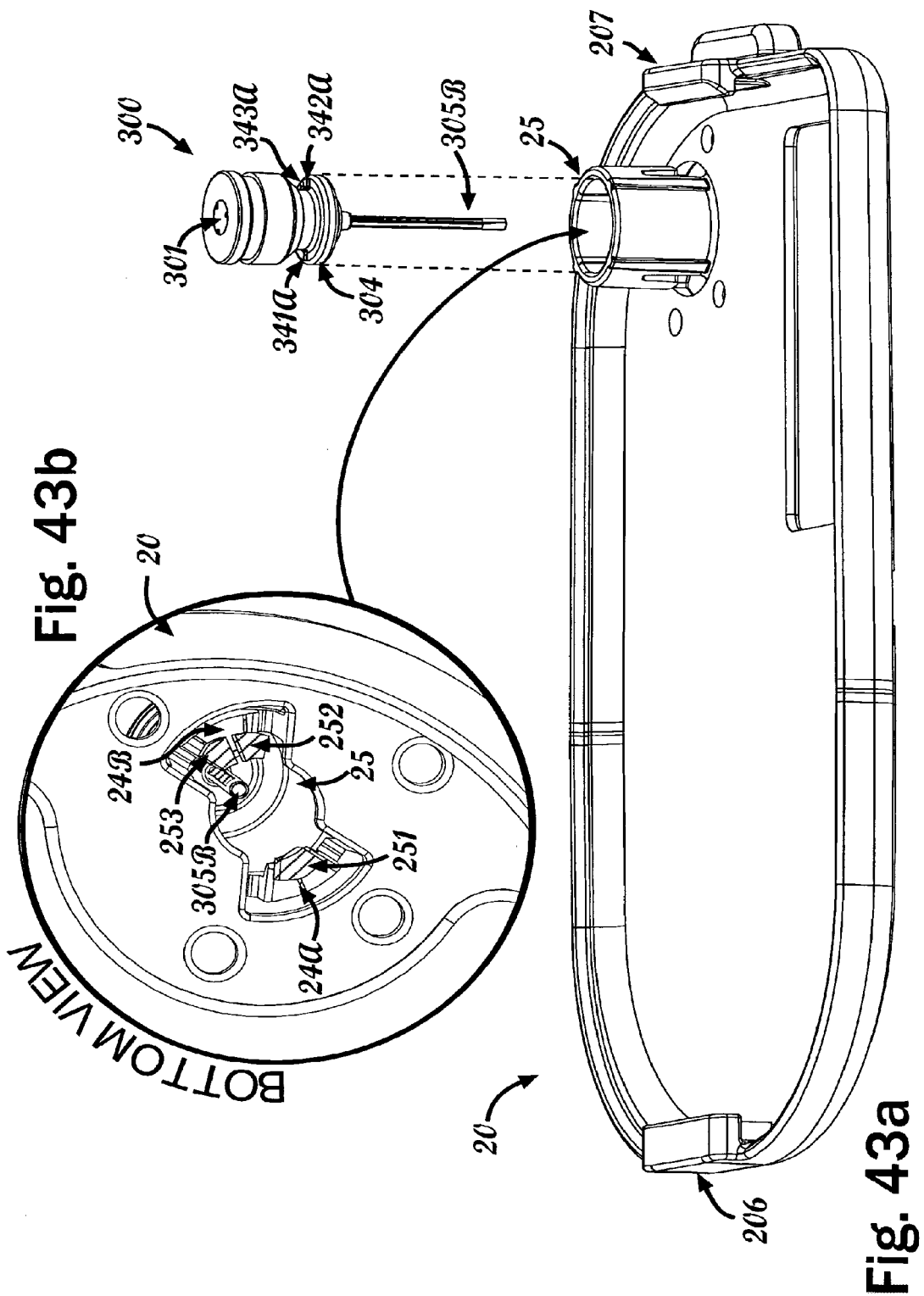

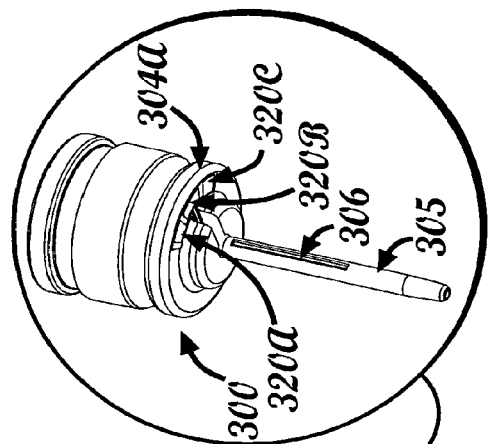
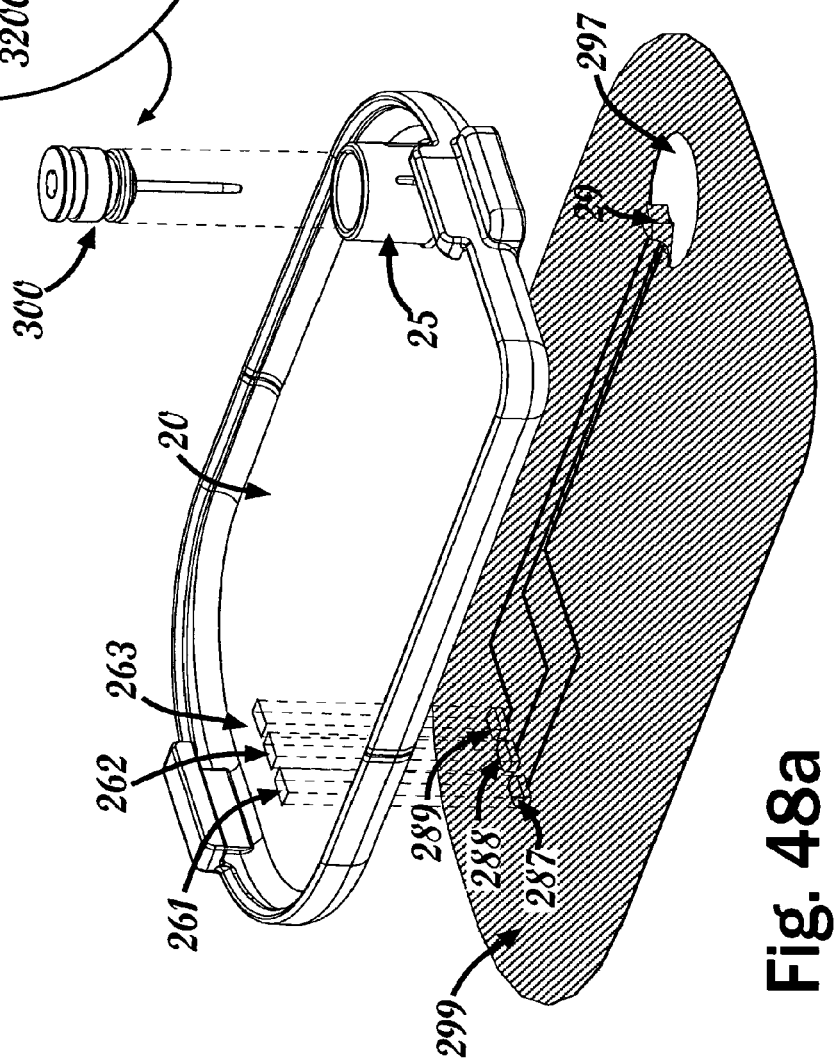
Fig. 48b
Fig. 48a

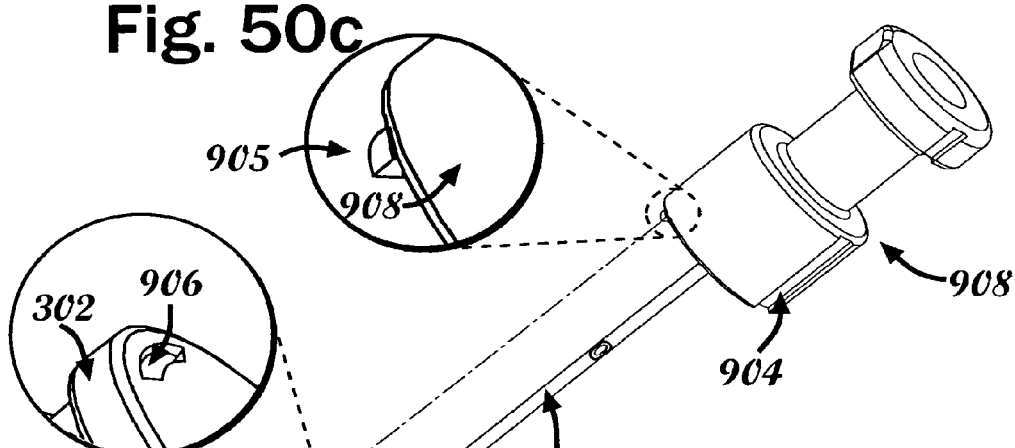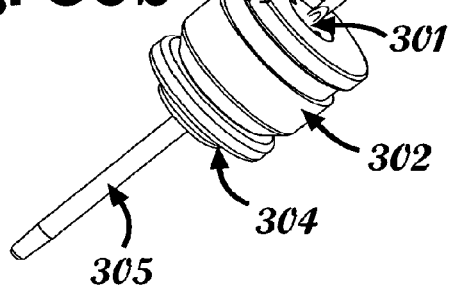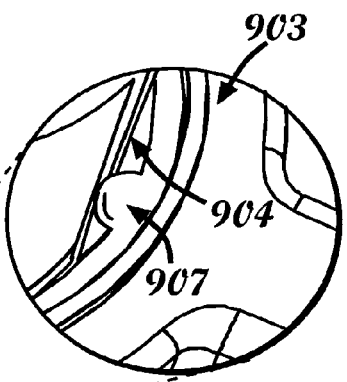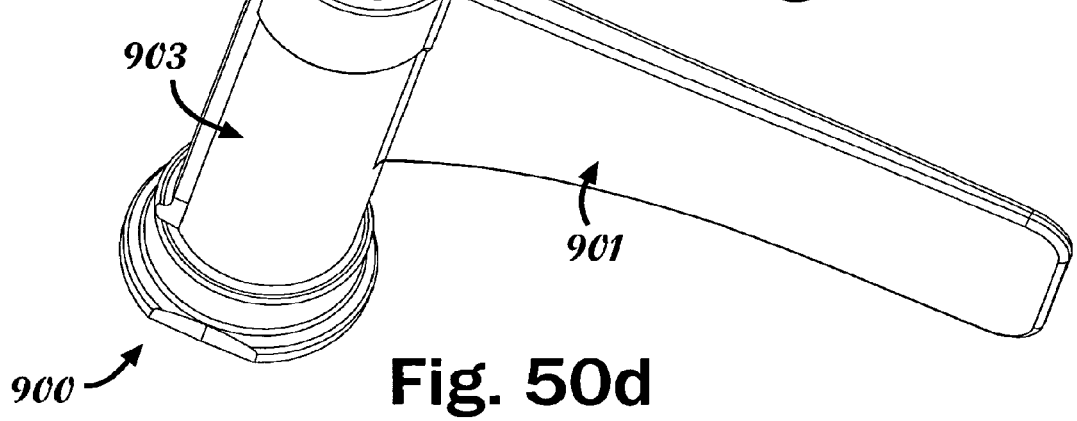

ANALYTE MONITORING AND FLUID DISPENSING SYSTEM

CROSS-REFERENCE TO RELATED APPLICATIONS

The present application is a 35 U.S.C. §371 national stage entry of PCT/IL2010/000997, which has an international filing date of Nov. 30,2010 and claims priority to U.S. Provisional Application No. 61/264,840, filed on Nov. 30, 2009 and entitled "Analyte Monitoring and Fluid Dispensing System" the disclosures of which are incorporated herein by reference in their entireties.

FIELD

Systems, devices, and methods for continuous monitoring of bodily analyte and continuous dispensing of therapeutic fluid are described herein. More particularly, a system comprising a continuous glucose monitor and insulin dispenser is described herein. Even more particularly, a device that is configured as a miniature, portable unit that can be adhered to a patient's skin and connected to one subcutaneous tip to continuously monitor glucose levels and dispense insulin is described herein.

The systems, devices and methods are not limited strictly to delivering insulin and monitoring glucose but, rather, apply to delivering any other drug and concomitantly monitoring any analyte. When used in the following description the term "analyte" means any solute composed of specific molecules dissolved in an aqueous medium.

BACKGROUND

Continuous Subcutaneous Insulin Injection (SCII)

Medical treatment of several illnesses requires continuous drug infusion into various body compartments, such as subcutaneous and intra-venous injections. Diabetes mellitus (DM) patients, for example, require administration of varying amounts of insulin throughout the day to control their glucose levels. In recent years, ambulatory portable insulin infusion pumps have emerged as a superior alternative to multiple daily syringe injections of insulin, initially for Type 1 diabetes patients (Diabetes Medicine 2006; 23(2):141-7) and consecutively for Type 2 diabetes patients (Diabetes Metab 2007 Apr. 30, Diabetes Obes Metab 2007 Jun. 26). These pumps, which deliver insulin at a continuous basal rate as well as in bolus volumes, were developed to liberate patients from repeated self-administered injections, and allow them to maintain a near-normal daily routine. Both basal and bolus volumes must be delivered in precise doses, according to an individual prescription since an overdose or under-dose of insulin could be fatal.

The first generation of portable infusion pumps concerns "pager-like" devices with a reservoir contained within the device's housing. These devices are provided with a long tube for delivering insulin from the pump attached to a patient's belt to a remote insertion site. Both basal and bolus deliveries in these "pager-like" devices are controlled via a set of buttons provided on the device. A user interface means including a screen are provided on the device's housing for advising the user regarding fluid delivery status, programming flow delivery, alerts and alarms. Such devices are disclosed, for example, in U.S. Pat. Nos. 3,771,694, 4,657,486 and 4,498, 843. These devices represent a significant improvement over multiple daily injections (MDI), but nevertheless, they are large sized, heavy, have long delivery/infusion tubing and lack discreetness, which substantially disturb daily activity.

To avoid the consequences of a long delivery tube, a new concept was proposed, which was implemented in second generation pumps. As described in prior art, this new concept concerns a remote controlled skin adherable device having a housing, a bottom surface adapted to be in contact with the patient's skin, a reservoir disposed within the housing, and an injection needle adapted for communication with the reservoir. In these second generation pumps, the user interface means are configured as a separate remote control unit that contains operating buttons and screen providing fluid delivery status, programming flow delivery, alerts and alarms, as described, for example, in U.S. Pat. Nos. 5,957,895, 6,589, 229, 6,740,059, 6,723,072, and 6,485,461. These second generation devices also have several limitations, such as being heavy, bulky, and expensive because the device should be disposed of every 2-3 days (due to insertion site infections and reduced insulin absorption). Another significant drawback of these second generation skin adherable devices is associated with the remote controlled drug administration. The user is totally dependent on the remote control unit. For example, the user cannot initiate bolus delivery or operate the device if the remote control unit is not at hand, if it is lost or if it malfunctions.

A third generation of skin adherable infusion devices was devised to avoid the cost issues associated with the second generation devices and to extend patient customization. An example of such a device was described in U.S. Patent Application Publication No. 2007-0106218 and in International Patent Application Publication No. WO2007/052277. This third generation device contains a remote control unit and a skin securable (e.g., adherable) device/patch unit that may include two parts: (1) a reusable part containing at least a portion of the driving mechanism, the electronics, and other relatively expensive components, and (2) a disposable part containing the reservoir and in some embodiments at least one power source (e.g., a battery).

This third generation concept provides a cost-effective, skin securable infusion device and may allow diverse usage such as various reservoir sizes, various needle and cannula types.

A fourth generation of infusion devices was devised as a dispensing unit that can be disconnected and reconnected from and to a skin adherable cradle unit, as disclosed, for example, in U.S. Patent Application Publication No. 2008-0215035 and International Patent Application Publication No. WO2008/078318. Such skin-securable dispensing units can be operated using a remote control and/or a user interface (e.g., a button-based interface) provided on a housing of the dispensing unit, as disclosed, for example, in International Patent Application Publication No. WO2009/013736 [also published as U.S. Patent Application Publication No. 2010-0204657], and International Patent Application Publication No. WO2009/016636 [also published as U.S. Patent Application Publication No. 2010-0145276], filed Jul. 31, 2008, claiming priority to U.S. Provisional Application Ser. Nos. 60/963,148 and 61/004,019, and entitled "Portable Infusion Device Provided with Means for Monitoring and Controlling Fluid Delivery", the disclosures of which are incorporated herein by reference in their entireties.

Continuous Glucose Monitoring (CGM)

Most diabetic patients measure their glucose levels several times during the day by obtaining finger-prick capillary samples and applying the blood to a reagent strip for analysis in a portable meter. While self-monitoring of glucose levels has had a major impact on improving diabetes care in the last few decades, the disadvantages of this technology are substantial and consequently leading to non-compliance. The drawbacks of this blood sampling technique are associated with discomfort of multiple skin pricking, inability to test the blood during sleep or when the subject is occupied (e.g., driving, running), and missing episodes of hyper- and hypoglycemia due to intermittent testing. A suggested glucose monitoring technology should therefore employ substantially automatic and continuous testing.

It is understood that there are three (3) techniques for continuously monitoring glucose in the subcutaneous interstitial fluid (ISF). The first technique is based on use of glucose oxidase based sensors as described in U.S. Pat. Nos. 6,360,888 to McIvor et al. and 6,892,085 to McIvor et al., both assigned to Medtronic MiniMed Inc. (CGMS, Guardian™ and CGMS Gold), and 6,881,551 to Heller et al., assigned to Abbott Laboratories, formerly TheraSense, Inc., (Navigator™). These sensors consist of a subcutaneously implantable, needle-type amperometric enzyme electrode, coupled with a portable logger.

The second technique is based on use of reverse iontophoresis-based sensors as detailed in U.S. Pat. No. 6,391,643 to Chen et al., assigned to Cygnus, Inc. (GlucoWatch™). A small current passed between two electrodes located on the skin surface draws ions and (by electro-endosmosis) glucose-containing interstitial fluid to the surface and into hydrogel pads incorporating a glucose oxidase biosensor (JAMA 1999; 282: 1839-1844).

The third technique, currently in clinical use, is based on microdialysis (Diab Care 2002; 25: 347-352), as detailed in U.S. Pat. No. 6,091,976 to Pfeiffer et al., assigned to Roche Diagnostics, as well as a marketable device (Menarini Diagnostics, GlucoDay™). In this technique, a fine, hollow dialysis fiber is implanted in the subcutaneous tissue and perfused with isotonic fluid. Glucose from the tissue diffuses into the fiber and is pumped outside the body for measurement by a glucose oxidase-based electrochemical sensor. Initial reports (Diab Care 2002; 25: 347-352) show good agreement between sensor and blood glucose readings, and good stability with a one-point calibration over one day.

Closed and Open Loop Systems

In an "artificial pancreas", sometimes referred to as a "closed loop" system, an insulin pump delivers appropriate dosage of insulin according to continuous glucose monitor readings. An artificial pancreas avoids a human interface and is expected to eliminate debilitating episodes of hypoglycemia, particularly nighttime hypoglycemia. An intermediate step in the way to achieve a "closed loop" system is an "open loop" (or "semi-closed loop") system also called "closed loop with meal announcement." In this model, user intervention is required in a way similar to using of today's insulin pumps by keying in the desired insulin before they eat a meal. A closed loop system is discussed in U.S. Pat. No. 6,558,351 to Steil et al., assigned to Medtronic MiniMed. The system is comprised of two separate devices, a glucose monitor and an insulin pump which are adherable to two remotely body sites and the loop is closed by an RF communication link.

However, the Steil et al. closed loop system has some drawbacks. For example, the glucose monitor and insulin pump are two discrete components which require two insertion sites and two skin-pricking sites for every replacement of the insulin pump and the sensor, typically every 3 days. In addition, being separated apart, the two system components should be connected either by radio communication link or by wires. Moreover, the pump is heavy and bulky, with long tubing, making the system non-discreet and the system is extremely expensive since the pump infusion set and the monitor sensor require disposal every three (3) days.

Thus, it is desirable to provide a skin securable device which is configured for both drug (e.g., insulin) dispensing and continuous body analyte (e.g., glucose) level monitoring. It is also desirable to have such a device which is miniature, discreet, economical for the users and highly cost effective. An embodiment of such a desirable device is preferably connected to a single skin-insertable tip which preferably includes a subcutaneous cannula for delivering the drug to the body as well as a probe for monitoring the analyte via a single insertion site. Such a device is preferably disconnected from and reconnected to a skin adherable cradle unit, such that after connection of the patch to the cradle, current generated on the probe is delivered to the processor within a housing of the device.

SUMMARY

Embodiments of the subject disclosure are directed generally to systems, devices, kits and methods for continuous dispensing of one or more therapeutic fluids and continuous monitoring of one or more bodily analytes. Some embodiments relate to a device that includes both a monitoring apparatus and a dispensing apparatus (the latter of which may be referred to as a pump). The pump may be used for infusing fluid into the body and the monitoring apparatus may be used for monitoring analytes within the body. In some embodiments, the monitoring apparatus and the pump share a single subcutaneously insertable, dispensing and sensing tip (hereinafter "tip"), which may also be referred to as a single subcutaneously insertable, dispensing and sensing cannula, designed to allow both analyte level monitoring and fluid dispensing, and in some embodiments, concomitantly. The tip preferably includes structure, such as a sensor, for monitoring one or more analyte levels within the body—for example, within the interstitial fluid ("ISF"). In some embodiments the sensor may include one or more sensors, which in some embodiments comprise electrodes, for monitoring one or more analyte levels within the body, and thus, embodiments referencing an "electrode(s)" may also be said to reference a sensor(s). In some embodiments, the electrodes may be provided on a probe (e.g., a planar probe), and thus, embodiments referencing a "probe" may also be said to reference a sensor(s).

In some embodiments, at the same time the tip is monitoring an analyte level, it is also performing as a cannula through which fluid is delivered to the body. In some embodiments, the tip comprises structure for multiple sensing (e.g., multiple sensors) for increasing the accuracy and reliability. In some embodiments, the pump and the monitoring apparatus may also work independently of each other, or may work together as a closed loop or semi-closed loop system. In some embodiments, the dispensing fluid comprises insulin to be used with diabetic patients and the analyte comprises glucose. The monitoring apparatus and pump may comprise a fluid delivery device, which may be configured as a skin securable device (hereinafter "patch" or "patch unit").

Some embodiments of the system and device include at least one of the following units and elements:

A patch unit that includes the monitoring apparatus and the pump. The monitoring apparatus includes structure for sensing one or more analytes (e.g., one or more sensors) and electrical communication elements connected thereto (e.g., electrodes, connecting wires, electrical connectors, electrical contacts). The patch unit may include at least one of a reservoir, driving mechanism, and pump. The patch unit may further include a printed circuit board ("PCB"), which includes a processor and can include a transceiver. The processor controls, in some embodiments, operation of the dispensing and monitoring apparatuses (hereinafter "processor-controller" or "processor/transceiver" or "processor"). For programming and data presentation, the device can be provided with a remote control unit, a display and/or with one or more operating buttons/switches on the patch unit. The device can also be provided with a skin adherable cradle unit (hereinafter "cradle") to which the patch unit can be repeatedly connected or disconnected thereto. The pump of the patch unit may employ different dispensing mechanisms, such as (for example) a syringe with a propelling plunger/piston (syringe type) mechanism, a peristaltic mechanism, pressurized reservoir, and the like. The patch unit may further include a reservoir and an outlet port which allows fluid communication between the reservoir and the tip when the patch unit is connected to the cradle unit.

The patch unit may be configured as a single part or consist of two parts, which may include a reusable part (hereinafter "RP") and a disposable part (hereinafter "DP"). The RP may contain the relatively expensive components, including one or more of: a driving mechanism (or a portion thereof), a PCB, a processor, electrical connectors for connection with the cradle unit (for example), and other electrical wirings. The DP may contain the relatively non-expensive and disposable components including reservoir and outlet port. In some embodiments, the patch unit further includes a power source which can be contained either in the reusable part or in the disposable part, or shared therebetween.

A cradle, which may also be referred to as a cradle unit, may also be provided for the patch unit. The cradle may be provided with a preferably flat bottom (according to some embodiments only) covered by an adhesive for adhering the cradle unit to the skin, with a passageway and at least one anchor (or latch) for the tip (the passageway and anchors hereinafter may be referred to as a "well"). The cradle unit may further include latches or snaps for enabling repeated connection and disconnection of the patch unit to and from the cradle unit (hereinafter referred to as "latches" or "snaps"). The cradle unit may further include a first set of electrical connectors surrounding the cradle passageway, electrical wiring, and second set of electrical connectors for connection with the RP, for enabling electrical communication from the tip.

The system according to some embodiments of the disclosure may further include a tip, which is insertable into the body for both fluid delivery and analyte monitoring. Accordingly, upon insertion, the tip is preferably rigidly connected to the well.

The tip, according to some embodiments, preferably includes a soft, multi-lumen tube (hereinafter "cannula"). One of the lumens comprises a fluid dispensing passageway and at least another lumen provides analyte sensing structure (e.g., a sensor, a probe, one or more electrodes). The distal end of the multi-lumen tube preferably converges to provide smooth penetration of skin. To that end, the proximal end of the multi-lumen tube becomes wider preferably forming a conical shaped funnel (according to some embodiments) to provide stable connection with a tip bushing (or tip housing).

Longitudinal openings or windows may also be provided in one or more of the lumens. Such openings (or windows), according to some embodiments, may provide direct contact of bodily fluids with sensing probe/electrodes located in the one or more lumens.

In some embodiments, electrodes may be provided within or on a probe that is located within one lumen of a double lumen cannula. Thus, the probe may include a distal end having sensing electrodes provided thereon, one or more wires for establishing electrical communication with the electrodes, and a proximal end including electrical connectors in electrical communication with the one or more wires, and thus, in electrical communication with the electrodes. The probe's distal end may be configured to be thin relative the diameter of the lumen. In some embodiments, the probe may have a width of about 0.6 mm, a thickness of about 0.1 mm, and a length of between about 5 mm and 9 mm (when inserted perpendicularly, though angled insertion may include longer lengths) and having a length substantially corresponding to the length of the lumen and preferably having a rectangular shape. The probe's proximal end may be wider and preferably matches the distal end of a cannula housing form/shape, and is preferably arched (e.g., circular, half circular or partially circular). The probe, according to some embodiments, includes a "neck" between the narrow distal end and wide proximal end to allow bending of proximal end and fixation of proximal end to distal end of the cannula housing (see below).

In some embodiments, the tip may also include a cannula cover (hereinafter "cover")—to support a septum, the cannula septum (hereinafter "septum") may maintain fluid communication between a connecting lumen and the cannula, a cannula bushing (hereinafter "bushing")—to connect the cannula to a cannula housing and a cannula cover.

The system according to some embodiments of the disclosure may further include a cartridge (which may also be referred to as a "cartridge unit") and/or a penetrating member, preferably a sharpened needle or needle-like piece used for skin pricking during tip insertion while being configured to be removed upon insertion of the tip. In addition, a protector element (which may be also referred to as "protector") may further be included and may be used to shield the tip and the penetrating member.

In some embodiments, the tip insertion can be done automatically by virtue of a spring loaded inserter as described in International Patent Application No. PCT/IL08/000,860 (published as WO2009/001346) and U.S. patent application Ser. No. 12/215,255 (published as US2008/0319414), the disclosures of which are hereby incorporated by their reference in their entireties.

In some embodiments, a remote control unit for controlling the patch unit is provided for example, the remote control may enable at least programming and/or controlling the operation of the pump and/or the sensor. In some embodiments, the remote control comprises a blood glucose monitor.

In some embodiments, the system and/or device includes additional external glucose monitoring (e.g., glucometer) and/or insulin dispensing unit (e.g., insulin pen/injector).

In some embodiments, the system and/or device includes one unit for continuous insulin delivery and continuous glucose monitoring using one common insertion site and one tip.

In some embodiments, the system and/or device may be comprised of one part or two parts and can be connected and disconnected from the body at user's discretion.

In some embodiments, a standalone tip can be inserted into the body, having a proximal end that remains out of the body and that can be connected and reconnected both to an insulin dispenser and glucose monitor.

In some embodiments, the system and/or device includes a glucose monitoring and insulin dispensing unit that can be disconnected and reconnected to a tip inserted in the body.

In some embodiments, the system and/or device includes a glucose monitoring and insulin dispensing unit that is highly cost-effective for the patient.

In some embodiments, a skin securable medical device is provided which may include one or more of: a tip configured for insertion and for delivering therapeutic fluid into the body of a patient, a pump for delivering the therapeutic fluid into the body of the patient via the tip, a sensor provided at the tip and configured for sensing a level of one or more analytes within the body of the patient and configured for providing at least one sensor signal indicative of the level of one or more sensed analytes, a processor for processing the at least one sensor signal and for controlling the therapeutic fluid delivery, at least one first connector provided on the tip for enabling electrical communication between the sensor and the processor, and an adherable housing portion for securing at least part of the device to the skin of the patient, where the adherable housing portion includes an opening and at least one second connector.

In some embodiments, e.g., like those described above, upon insertion of the tip through the opening, the at least one first connector is coupled to the at least one second connector establishing electrical communication therebetween and enabling transfer of the at least one sensor signal from sensor to the processor.

In some embodiments, the tip may comprise a cannula for delivering the therapeutic fluid therethrough.

In some embodiments, the sensor may comprise a plurality of electrodes for sensing the level of one or more analytes.

In some embodiments, the one or more analytes comprises glucose. In further embodiments the therapeutic fluid comprises insulin.

In some embodiments, at least one electrode of the plurality of electrodes may comprise one or more redox enzymes for oxidizing the glucose and generating electrical current for transferring the at least one sensor signal. In some embodiments, at least one electrode of the plurality of electrodes may comprise at least one glucose binding protein.

In some embodiments, the sensor and/or tip may further comprise a plurality of electrical conducting elements for transferring the at least one sensor signal from the sensor to the processor, via the at least one first and second connectors.

In some embodiments, the plurality of electrical conducting elements comprises wires.

In some embodiments, such as those described above, at least a portion of the sensor is bent (or folded or twisted) for enabling physical contact between the at least one first and second connectors upon insertion of the tip through the opening.

In some embodiments, the cannula/tip includes a first lumen for delivering the therapeutic fluid and one or more second lumens for providing at least a portion of the sensor. To that end, the one or more second lumens can include any number including 1, 2, 3, 4, 5, 6, etc.

In some embodiments, the plurality of electrodes comprises one working electrode, one counter electrode and optionally one reference electrode.

In some embodiments, the plurality of electrodes comprises three working electrodes, three counter electrodes and optionally one reference electrode.

In some embodiments, each electrode resides in separate one or more second lumens of the tip.

In some embodiments, the plurality of electrodes is provided on a probe. The probe may reside within a lumen of the one or more second lumens of the tip.

In some embodiments, the one or more second lumens may include one or more windows enabling exposure of at least a portion of the sensor to the surrounding. The surrounding may include the interstitial fluid.

In some embodiments, the one or more windows are configured for enabling mechanical support to the at least a portion of the sensor.

In some embodiments, the one or more second lumens can be substantially shorter than the first lumen.

In some embodiments, the one or more second lumens can be sealed at a distal end.

In some embodiments, the first lumen may have a substantially circular cross section and the one or more second lumens may have a substantially arched cross section.

In some embodiments, the pump delivers the therapeutic fluid in correspondence with the at least one sensed signal.

In some embodiments, the processor automatically operates the pump and the sensor.

In some embodiments, the device can operate in a mode selected from the group consisting of: a closed loop mode, a semi-closed loop mode, and an open loop mode.

In some embodiments, including those described above, the adherable housing portion comprises a cradle, the cradle may include a well for receiving the tip and at least one latch for connecting the cradle and the device. In some embodiments, the adherable housing portion includes a latch which comprises the at least one second connector for establishing electrical communication with the at least one first connector. In some embodiments, a latch may be used interchangeably with one of "connection means", connection mechanism", "protrusion" and/or "anchor".

Embodiments of the adherable housing portion may include any of the features related to the cradle, described in the present disclosure.

In some embodiments, the well may comprise the at least one second connector for establishing electrical communication with the at least one first connector.

In some embodiments, the cradle may comprise at least one third connector configured to transfer the at least one sensor signal received from the sensor to a fourth connector located in another unit (e.g., the pump, RP, DP, external device).

In some embodiments, the cradle may also include one or more electrical wires, which may be embedded (e.g., within one or more tunnels) within the cradle. In some embodiments, the wires are used to transfer sensor signals received from sensor/probes/electrodes in the cannula/tip.

In some embodiments, the adherable housing portion includes an adhesive tape, and the adhesive tape includes at least one second connector, at least one third connector, and at least one wire connecting between the at least one second and third connectors for transfer the at least one sensor signal received from the cannula/tip to the processor.

In some embodiments, the cradle includes an amplifier and/or a power source.

In some embodiments, the opening (e.g., well) is configured to enable tip insertion in an angle with respect to the adherable housing portion (e.g., cradle).

In some embodiments, the device may further comprise a cannula cartridge unit having a penetrating member for piercing the skin of the patient during insertion of the tip, and an inserter. The cannula cartridge and the penetrating member may be configured to align the tip such that upon insertion of the tip through the opening, the at least one first connector contacts the at least one second connectors.

Embodiments of the systems and/or devices may include any of the features described in the present disclosure, including without limitation any one or more of the methods, systems and/or devices, as well as any one or more of the above and/or following features.

In some embodiments, a cannula assembly for use with drug dispensing pump is provided, where the cannula assembly includes a probe including at least one electrode, and a cannula housing. A proximal end of the probe comprises a first wire/connector which conforms to the configuration of the cannula housing and the probe is folded (or bent or twisted) according to the configuration of the cannula housing. The folded probe may enable contact of the first wire/connector with a second wire/connector provided on another unit.

In some embodiments, the cannula housing may include a slot configured to receive the wire/connector in close contact with the bottom or side of the cannula housing. The slot may be configured annularly in a ring-like configuration.

Such cannulae, according to some embodiments, may comprise a double-lumen cannula which includes a first lumen for providing a passageway for fluid dispensing and a second lumen for providing the probe.

In some embodiments, a cannula assembly for use with drug dispensing pump is provided, where the cannula includes a plurality of electrodes and a cannula housing. A proximal end of the plurality of electrodes comprises first wires/connectors which conforms to the configuration of the cannula housing. This arrangement may enable contact of first wires/connectors with second wires/connectors provided on another unit, for example, a skin adherable housing (e.g., a cradle).

In some embodiments, the cannula may comprise multiple lumens: a first lumen for providing a passageway for fluid dispensing, and additional lumens for providing corresponding electrodes such that each electrode corresponds to a separate lumen.

In some embodiments, the additional lumens encircle the first lumen and the cannula assemblies may include a connector plate on one side of the cannula housing, such that the electrodes are connected (e.g., by wires) to the connector plate via an opening provided on each of the additional lumens.

In some embodiments, the connector plate is formed as a circular or annular plate. In some embodiments, the wires and connector plate may be formed as a single integral conducting element.

In some embodiments, the connector plate comprises a first plurality of folded connectors configured to contact the plurality of electrodes provided by the additional lumens via the openings, and a second plurality of folded connectors configured the second wires/connectors provided on the other unit. In some embodiments, the plurality of electrodes are folded according to the configuration of the cannula housing for enabling contact of the first wires/connectors with the second wires/connectors.

Embodiments of the systems and/or devices may include any of the features described in the present disclosure, including without limitation any one or more of the methods, systems and/or devices, as well as any one or more of the above and/or following features.

In some embodiments, a skin-adherable cradle for connection with a patch pump is provided, and may include a well for housing a cannula assembly, a plurality of electrical wires, a plurality of electrical contacts configured as snap connectors, where each corresponding with one of the plurality of electrical wires.

In some embodiments, the skin-adherable cradle may comprise a plurality of first electrical connectors configured to contact electrical connectors of the cannula assembly, each may correspond with one of the plurality of electrical wires, and a plurality of second electrical connectors configured to contact electrical connectors of a patch unit, each may correspond with one of the plurality of electrical wires.

The snap connectors may be configured such that they remain sealed when the patch unit is disconnected from the cradle. To that end, a non-conductive sealed cap may be provided for covering one or more of the snap connectors. Such a sealed cap may also include conducting contacting pads embedded within the cap, such that upon contact with the connectors of the patch unit, electrical current is conducted. In other embodiments, the connectors of the patch unit are configured to prick the non-conductive sealed cap for establishing electrical communication with the plurality of second connectors.

In some embodiments, upon connection of the plurality of first electrical connectors with the connectors of the cannula assembly, the connectors may be sealed (e.g., via O-ring(s) provided by the opening).

Furthermore, in some embodiments, a cannula cartridge unit for use with a cannula insertion device is provided and may include one or more of: a housing, a handle, and a cannula, where the cannula may include one or more of a plurality of electrodes, a plurality of corresponding connectors, each for a respective electrode, and a plurality of lumens including a first lumen for delivering fluids and one or more second lumens for providing the electrodes. The cartridge may also include a penetrating member provided initially longitudinally through one of the lumens. In some embodiments, the cannula of the cartridge unit further includes ate least one of a septum, a cover, and a cannula housing. Moreover, in some such embodiments, the penetrating member may comprise a needle and a needle cover.

In further embodiments of the cannula cartridge, a latch may be provided at a bottom portion of the needle cover as well as a corresponding groove provided in the cover of the cannula for aligning and coupling the needle cover with the cannula. In some embodiments, the groove may comprise a plurality of grooves and a plurality of latches may then be provided on cannula cartridge housing for aligning and/or coupling the needle cover with the cartridge housing. The one or more grooves may be configured as tracks for enabling movement of the needle cover for insertion of the cannula into the body of the patient while being aligned with the cannula cartridge housing.

In some embodiments, a kit for therapeutic treatment of a patient is provided an may comprise one or a plurality of any one or more of the devices and/or elements/components thereof for any one or more embodiments described or otherwise described in this disclosure.

Other embodiments of the subject disclosure include methods for assembly, methods of use, and methods of treatment of any of the device, system, and kit embodiments described in the subject disclosure, or elements/components thereof.

Accordingly, it is an object of some of the embodiments to provide a system and/or device that includes a unit for frequent or continuous measurements of bodily analyte levels and a unit for frequent or continuous delivery of therapeutic fluid into the body.

It is another object of some of the embodiments to provide a system and/or device that includes a unit for frequent or continuous measurements of glucose levels and a unit for frequent or continuous delivery of insulin.

It is another object of some of the embodiments to provide a system and/or device that includes a unit for frequent or continuous measurements of glucose levels and a unit for frequent or continuous delivery of insulin according to the monitored glucose levels.

It is another object of some of the embodiments to provide a system and/or device that is configured as a skin adherable unit which includes a glucose monitoring apparatus and an insulin pump.

It is another object of some embodiments to provide a single patch unit, in which the monitoring and pumps can concomitantly use a common insertion site and one tip that serves both as a probe for monitoring glucose levels and as a cannula for delivering insulin. The glucose level may be monitored within the ISF in the subcutaneous tissue, and the insulin may be delivered into the subcutaneous tissue.

It is another object of some embodiments to provide a patch unit that includes monitoring and pumps and has two-parts—a reusable part and a disposable part. The reusable part may include relatively expensive components, e.g., electronics, a driving mechanism, and the disposable part may include relatively inexpensive components, e.g., a reservoir.

It is another object of some of the embodiments to provide a system and/or device that is configured as a patch unit and contains both a continuous glucose monitoring apparatus and insulin pump. The patch unit can be controlled by a remote control unit or by buttons provided anywhere on the patch unit.

It is another object of some embodiments to provide a patch unit capable both of analyte monitoring and fluid dispensing and that is thin, miniature, can be hidden under the clothes, can be attached to the patient's body at any desired location, avoid long tubing, and does not interfere with normal daily activities.

It is another object of some embodiments to provide a patch unit which includes both monitoring and pumps, where the patch unit can be connected to a tip insertable within various bodily tissue, including, for example, subcutaneous tissue, blood vessels, peritoneal cavity, muscles, and adipose tissue.

BRIEF DESCRIPTION OF THE DRAWINGS

FIGS. 1a-c show a block diagram of a system which includes and a patch unit that can be comprised of one or two parts according to some embodiments of the disclosure. The system may include a remote control unit.

FIGS. 6a-b show a cross sectional view of the tip and the cradle after tip insertion according to some embodiments of the disclosure.

FIG. 9a shows a cannula with two lumens. FIG. 9b shows a cannula with four lumens.

FIGS. 12a-b show electrodes that are located on one probe that is provided by one lumen of a double lumen cannula. The phrase "provided by" includes any arrangement of an electrode(s)—relative to a lumen(s), unless specifically stated otherwise, including, for example, an electrode(s) being inserted into a lumen(s) or located therein.

FIGS. 12c-d show electrodes that are located apart from each other such that each electrode is provided by a separate lumen that is located on the outer circumference of the cannula encircling the lumen that serves as the fluid passageway.

FIG. 17a shows the tip before insertion. FIG. 17b shows the process of tip insertion.

FIGS. 33a-b show the tip before connection to cradle and electrical current conduction from the probe within the tip to the wires within the cradle according to some embodiments of the disclosure.

FIGS. 35a-c show spatial (35a), top (35b) and bottom (35c) views of a connectors plate according to some embodiments of the disclosure.

FIGS. 43a-b show electrical connections between the tip and the cradle according to some embodiments of the disclosure.

FIGS. 48a-b show connection of the tip, the cradle, and the conductive adhesive tape according to some embodiments of the disclosure.

FIGS. 50a-e show assembly of the tip to a needle and to the cannula cartridge according to some embodiments of the disclosure.

DETAILED DESCRIPTION

Figure 2A:
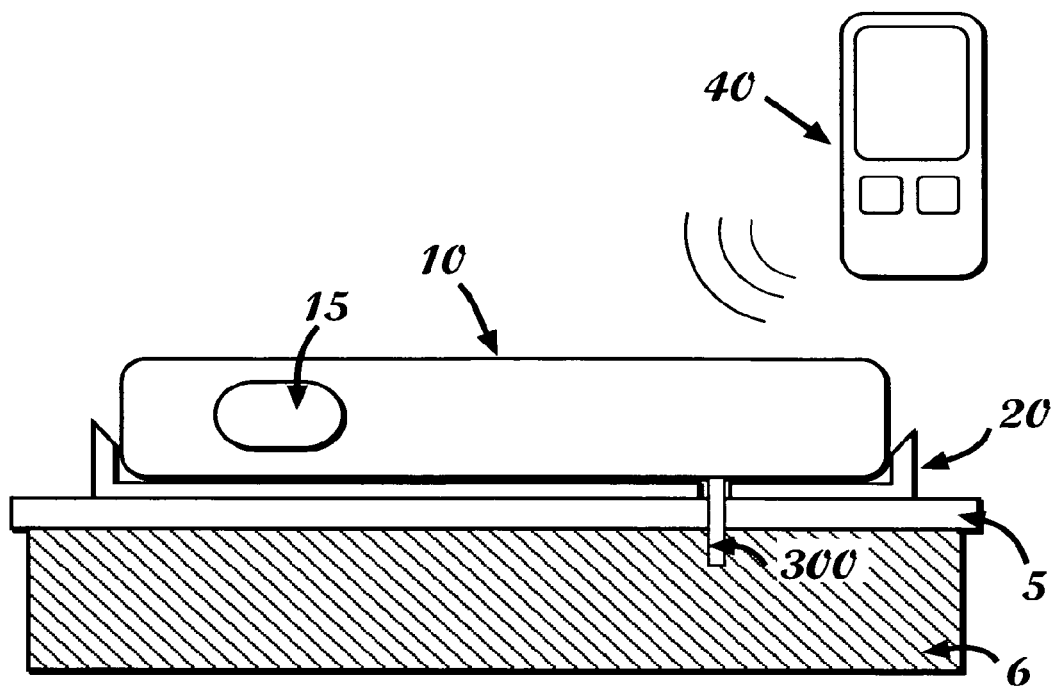
FIGS. 2a-b show a single part (2a) and a two part (2b) patch according to some embodiments of the disclosure. The patch is removable secured to a skin adherable cradle which adheres to skin with adhesive. The tip is rigidly connected to the cradle and resides within the body. The tip serves as a conduit for drug delivery and as a probe for sensing analyte.

Throughout the following detailed description, similar structure/elements referred to in various embodiments illustrated in the figures are referred to with the same reference number. Accordingly, in many circumstances, repetition of the introduction of an already described element/feature introduced in an earlier figure is avoided in subsequently described figures. Moreover, any one or more elements/features/structure and/or step of any one or more disclosed embodiments may be substituted and/or provided with any other disclosed embodiment to provide yet another embodiment of the subject disclosure.

FIGS. 1a-c illustrate a block diagram of a system and device which may include a dispensing unit 10 (i.e., a pump) and, in some embodiments, a remote control unit 40. In some embodiments, the dispensing unit 10 may be referred to as a "patch" due to its structural similarity to a thin patch that can be affixed/secured to the patient's body. In some embodiments, the patch unit 10 may include a pump for delivering one or more fluids into the body and a sensing apparatus for monitoring one or more analyte levels within the body. The fluid delivery may be automatically regulated (via one or more processors or controllers, for example) according to one or more analyte levels (e.g., closed loop system) or partially regulated according to one or more analyte levels (e.g., open loop system). For example, the fluid delivery may be regulated during a portion of a day, just at night, all the time excluding meals, etc.

The patch 10 may include a single part (FIG. 1b) or, in some embodiments, two parts (FIG. 1c). The two-part patch 10 may include a reusable part 100 and a disposable part 200. In some embodiments, the sensing apparatus and/or the pump may be positioned within the reusable part 100, the disposable part 200 or both. The reusable part may contain electronics (e.g., a printed circuit board and/or a processor and/or a memory), driving mechanism (or at least a portion thereof) and other relatively expensive components (e.g., sensors). The disposable part may contain a reservoir, an outlet port, a portion of the driving mechanism (in some embodiments) and other relatively inexpensive components. In some embodiments, the remote control ("RC") 40 may be configured as a handheld device for programming fluid infusion rates, controlling at least the dispensing unit/patch, acquiring data, communicating with other electronic devices (e.g., a personal computer) and providing one or more of visual, audible and vibratory notifications regarding at least the operation and/or programming of the dispensing unit and/or the sensing apparatus. In some embodiments, the remote control 40 may include a screen and a keypad. The remote control 40 may further include a blood glucose monitor, where a test strip may be inserted into a designated slot and glucose readings may be presented on the screen. A two-part patch is disclosed, for example, in U.S. Patent Application Publication No. 2007-0106218, and in International Patent Application Publication No. WO2007/052277, the contents of all of which are incorporated herein by reference in their entireties.

In some embodiments, the remote control may be configured, without limitation, as a watch, a cellular phone, a personal digital assistance ("PDA"), a smartphone (e.g., an iPhone or Android devices), a media player (e.g., an iPod, an mp3 player), an iPad, a laptop, and/or a PC.

In some embodiments, the system may not include a remote control 40 and the patch unit 10 may be operated using a user interface (e.g., a button/switch-based interface and/or a voice commander) provided on a housing of the patch unit 10, as disclosed, for example, in International Patent Applications Publications Nos. WO2009/013736 and WO2009/016636, the contents of all of which are hereby incorporated by reference in their entireties.

Figure 2B:
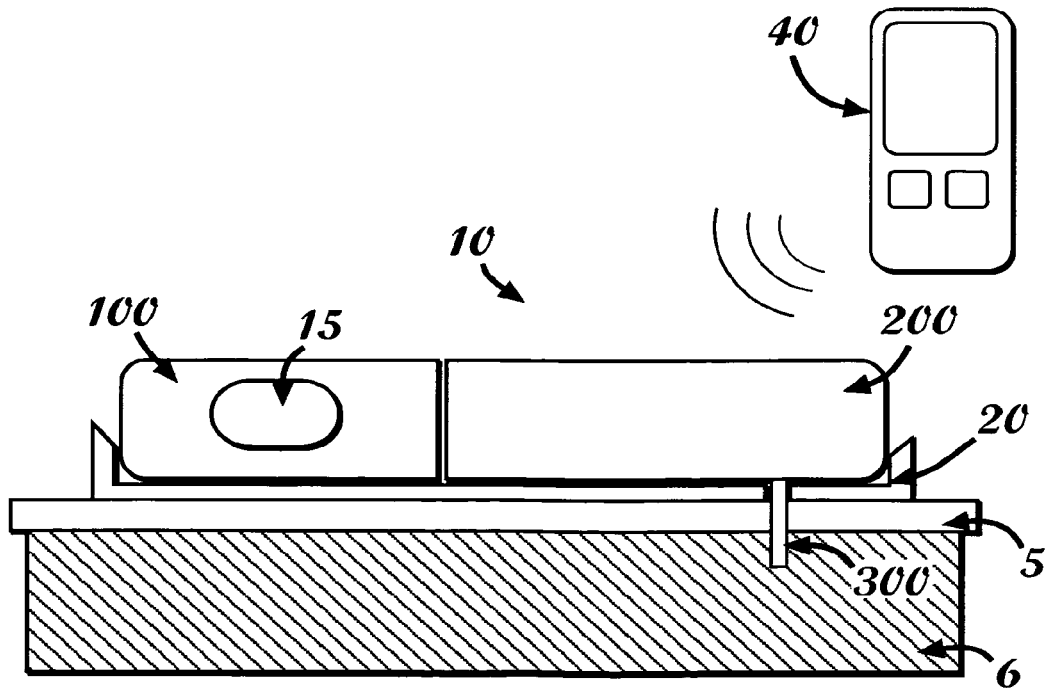

FIGS. 2a-b illustrate embodiments of the patch unit 10 similar to structure of the patch unit shown and described in FIG. 1b-1c. Accordingly, in some embodiments, the disposable part 200 may include an outlet port with a connecting lumen to enable fluid communication between a reservoir (located in the disposable part 200, for example) and the patient's body, via a subcutaneously inserted tip 300.

As also shown in FIGS. 2a-b, in some embodiments, a cradle unit 20 may be provided for securing the patch 10 to the body of the patient. Embodiments of the cradle unit ("cradle") 20 may be configured as a substantially flat sheet or plate including a surface that can be secured (e.g., adherable) to the patient's skin 5, e.g., via an adhesive layer provided on a bottom surface of the cradle. Accordingly, the patch 10 may be disconnected from and reconnected to the cradle 20. The cradle may also contain a passageway (e.g., an opening, window) for insertion of the tip 300 into the body of the patient, to the subcutaneous tissue 6, for example. Embodiments of a device comprising a cradle are disclosed, for example, in U.S. Patent Application Publication No. 2008-0215035 and in International Patent Application Publication No. WO2008/078318.

The tip 300 may penetrate the patient's skin 5 and reside (at least in part) within the body of the patient 6 (e.g., within the subcutaneous tissue). The tip 300 may serve as a conduit for delivering therapeutic fluid to the body of the patient (hereinafter "cannula") and may include a sensor. In some embodiments the sensor may include a probe and/or electrodes for sensing analyte within the body (the probe may comprise one or more electrodes). In some embodiments, the drug comprises insulin and the analyte comprises glucose.

Such a dual function patch 10 may be operated with functional buttons/switches located on the patch and/or by a remote control 40. For example, in a two part patch 10, two operating buttons 15 (e.g., bolus buttons) may be located on the reusable part 100 (illustrating one (1) button out of two (2) in FIGS. 2a-2b) for issuing commands related to fluid delivery, for example.

Figure 3:
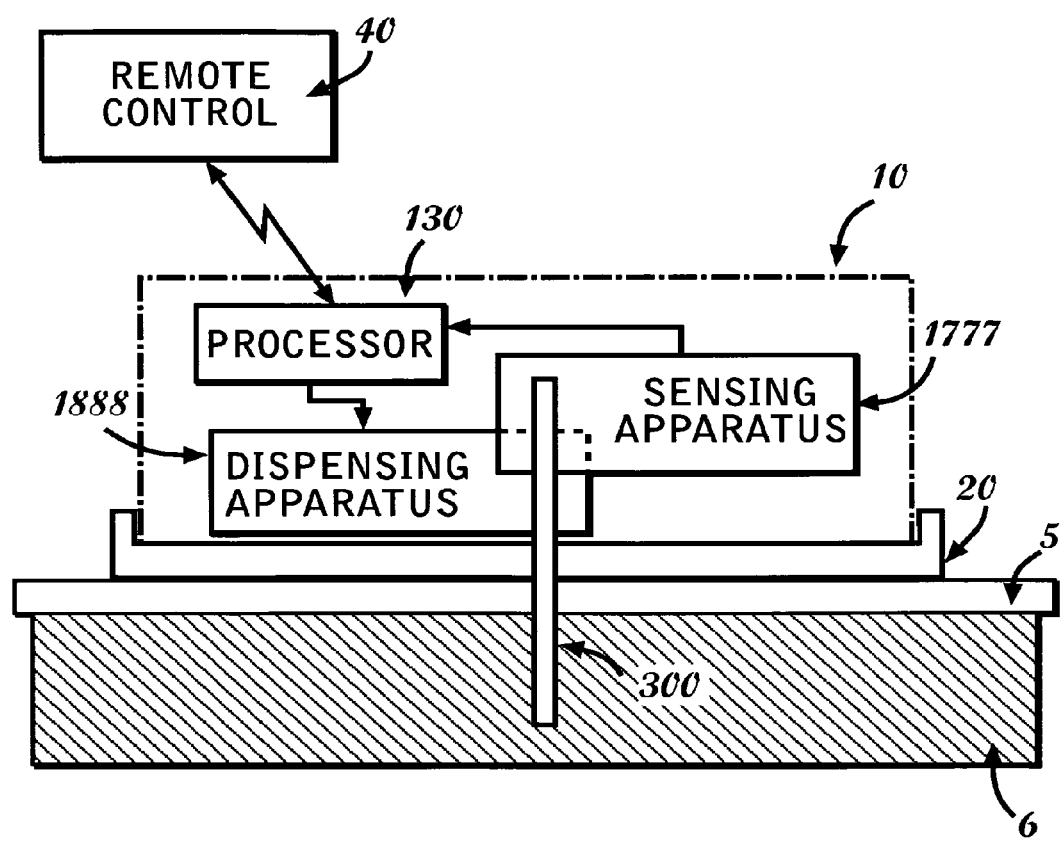
FIG. 3 shows a schematic presentation of a sensing apparatus and a pump of the patch unit according to some embodiments of the disclosure. A single tip is provided for dispensing drug into the body and sensing analyte levels within the body. The pump can be fully (closed loop system) or partially (open loop system) controlled by the sensing apparatus.

FIG. 3 illustrates an embodiment of the patch unit 10 which may comprise a sensing apparatus 1777 for sensing an analyte levels and a pump 1888 for delivering a therapeutic fluid. In some embodiments, the therapeutic fluid may comprise insulin, the analyte may comprise glucose and the sensing apparatus may include a continuous glucose monitor ("CGM"). The sensing apparatus 1777 and/or the pump 1888 may be controlled by a processor (which may also include a transceiver) 130. Analyte levels sensed by the sensing apparatus 1777 may be processed by the processor 130. In some embodiments, the processor 130 may control the delivery of therapeutic fluid by the pump 1888 automatically according to (or based on) the analyte levels sensed by the sensing apparatus 1777 (forming a closed loop system). In some embodiments, the delivery of therapeutic fluid may be controlled by the processor 130 according to a pre-programmed plan set by a caregiver, for example, and/or a plan manually adjusted by the patient via user interface located on the remote control or on the patch unit (e.g., manual buttons or switches) according to the sensed analyte levels (forming an open loop system or semi-closed system), for example. A combination thereof may be also implemented, for example, basal insulin delivery during the night may be dispensed automatically according to glucose levels and meal bolus delivery may be manually programmed by the user.

The processor 130 may be configured to establish two-way communication, via the transceiver, with RC 40 for programming the pump and/or the sensing apparatus using RC interface and/or presenting data relating the pump and/or the sensing apparatus on RC screen. For example, fluid delivery may be programmed using the RC interface and analyte delivery may be presented on the RC screen. In some embodiments, a screen may be provided on the reusable part housing also presenting data relating the dispensing apparatus and/or the sensing apparatus.

In some embodiments, the tip 300 may be shared between the dispensing apparatus (may be referred to as a pump) 1888 and the sensing apparatus 1777. The tip 300 may serve as a conduit for delivering therapeutic fluid to the body of the patient (hereinafter "cannula") and may also include a probe and/or electrodes for sensing one or more analytes within the body. The tip 300 may be inserted through an opening in cradle 20 and through patient's skin 5 into the body of the patient 6 (e.g., subcutaneous tissue). According to some embodiments, the probe may be located within or on the cannula 6, as described in U.S. Patent Application Publication Nos. 2007/0191702 to Yodfat et al. and 2008/0214916 to Yodfat et al., and International Publication No. WO2008/078319 to Yodfat et al., the disclosures of which are incorporated herein by reference in their entireties.

Figure 4:
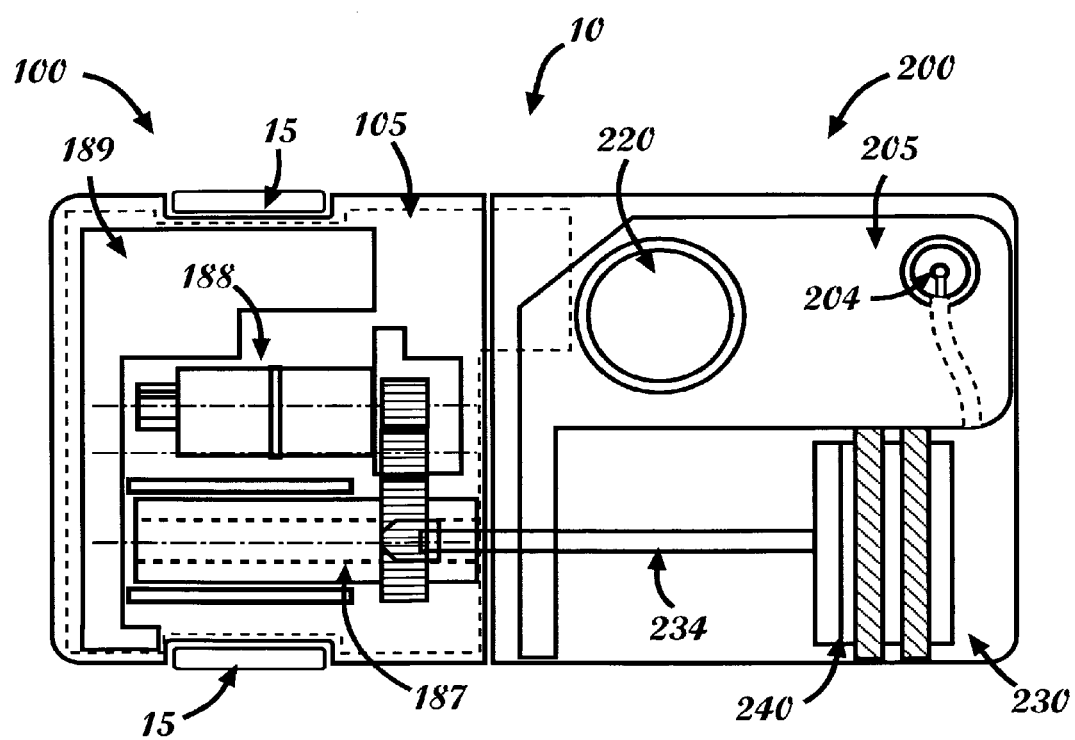
FIG. 4 shows the pump of a two part patch unit according to some embodiments of the disclosure.

FIG. 4 shows a longitudinal cross sectional view of a two-part patch 10, according to some embodiments, including components of the pump. As noted earlier, in some embodiments, the patch 10 may include a reusable part ("RP") 100 and a disposable part ("DP") 200. The reusable part may include a reusable housing and a reusable insert (e.g., reusable chassis) 105 to support RP's components and the disposable part may include a disposable housing and a disposable insert (e.g., disposable chassis) 205 to support DP's components.

Upon RP-DP connection, the RP's insert 105 and the DP's insert 205 are engaged and RP's housing and DP's housing are aligned and sealing is enabled, for example via sealing gaskets providing a waterproof sealing. The reusable part 100 may include a driving mechanism (e.g., a motor and gears) 188, a rotating sleeve 187, and a Printed Circuit Board (PCB) with electronic components (e.g., antenna) 189. The disposable part 200 may include a reservoir 230, a plunger (piston) 240, a plunger rod 234, a battery 220, and an outlet/exit port 204. Upon connection of RP with DP, a toothed tip of the plunger rod 234 may be inserted into a toothed inner side of rotating sleeve 187 such that rotation of the motor and gears may rotate the plunger rod 234. A nut within the DP's insert 205 may convert the rotational movement into a linear displacement of the plunger rod 234 and plunger 240 within reservoir 230 such that the fluid (e.g., insulin) contained within the reservoir 230 is dispensed from the reservoir, through a delivery tube (curved dotted lines) and out via the exit port 204.

Figure 5:
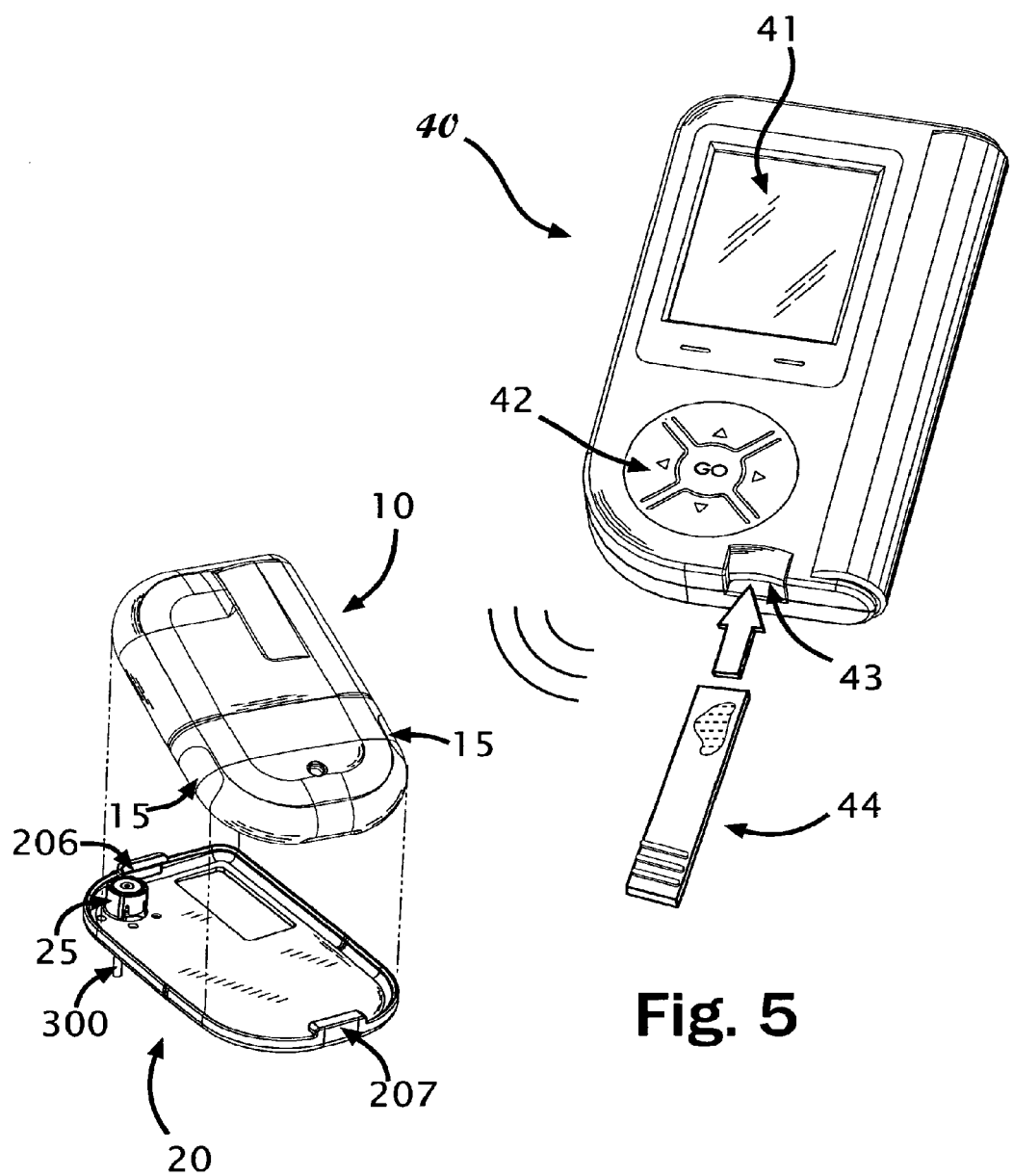
FIG. 5 shows a spatial view of the system that includes a patch unit, a remote control unit, a cradle unit and a tip unit according to some embodiments of the present disclosure.

FIG. 5 shows a spatial view of a system, according to some embodiments, which may include one or more of the following components:

The patch unit ("patch") 10, where fluid dispensing commands may be issued, according to some embodiments, by buttons/switches 15 located on the patch 10. In some embodiments, the RP 100 may be a durable unit/assembly which is replaced every three (3) months, for example, and the DP 200 may be a single-use unit/assembly which is discarded and replaced every 2-3 days, for example.

The remote control unit ("RC") 40 that may include a screen 41 and a keypad 42. In some embodiments, the RC 40 may further include an integrated blood glucose monitor having a slot 43 to receive a blood test strip 44. The RC 40 may be used for patch programming (e.g., fluid dispensing commands) and/or data acquisition. Data acquisition may be accomplished, in some embodiments, by communication of the RC 40 with other electronic devices, such as a PC, to carry out data downloading and uploading, for example.

The cradle unit 20 ("cradle") which may include a substantially flat sheet or plate base with an opening enabling tip insertion via the cradle into the body. The cradle 20 may include an adhesive layer at its bottom surface for securing the cradle to the skin of the patient. The cradle 20 may further include connecting means (e.g., "snaps" or latches) 206, 207 for rigidly securing the patch 10 to the cradle 20 and allowing disconnection and reconnection of the patch from and to the cradle 20, upon patient's discretion. A tubular shaped protrusion around the opening (also referred-to as "well") 25 may provide support for the tip 300 by maintaining rigid connection of tip 300 (and/or tip related assemblies as shown in FIG. 6a) to cradle 20 after insertion of the tip to the body via the well 25.

The tip unit 300 ("tip") which may comprise a fluid conduit for fluid delivery and a probe and/or electrodes for continuously monitoring bodily analyte.

An example of such a device is disclosed in a U.S. Patent Application Publication No. 2008/0215035 to Yodfat et al and International Patent Application Publication No. WO2008/078318 to Yodfat et al, the contents of all of which are hereby incorporated by reference in their entireties. Such a device is further disclosed in U.S. Patent Application Publication No. 2007/0106218, to Yodfat et al, International Patent Application Publication No. WO2007/052277, to Yodfat et al, and in International Patent Application Publication No. WO2009/125398, to Yodfat et al, the contents of all of which are hereby incorporated by reference in their entireties. U.S. Patent Application Publication No. 2007/0191702, the content of which is hereby incorporated by reference in its entirety, discloses a device that includes a dispensing patch unit (e.g., an insulin dispensing patch) and an analyte sensor (e.g., a continuous glucose monitor). This type of dual function device has a similar configuration to that outlined above and can also be disconnected and reconnected from and to the skin at patient's discretion.

FIGS. 6a-b show a cross sectional view of the tip 300 and the cradle 20 after insertion of the tip to the body of the patient. The cradle 20 may be adhered to skin 5 and include connection means 206 and 207 securing the patch unit to the cradle. After insertion of the tip to the body through the well 25, the well 25 may provide support (e.g., mechanical support) for the tip 300 and maintain rigid connection of the tip 300 to the cradle 20. The tip 300 may include a proximal portion and a distal portion. The proximal portion of tip 300 having a cover 302 configured to be secured within the well 25 (after tip insertion). The proximal portion may further include a self-sealable septum 301 providing sealing at least to the cannula 305. The distal portion of the tip 300 is configured to be located within the subcutaneous tissue below the skin 5 after insertion of the tip 300 into the body. The distal portion may include a fluid conduit (hereinafter "cannula" 305) for transferring or dispensing therapeutic fluid (e.g., insulin) to the body of the patient and a probe 30 and/or electrodes for sensing analyte (e.g., glucose) within the body. FIG. 6b shows a magnified view of an example of the probe 30. The probe 30 may include one or more electrodes, for example a working electrode 321, a counter electrode 322, and optionally a reference electrode 323. The working electrode 321 may include an area where an electrochemical, optionally enzymatic, reaction occurs; the counter electrode 322 may complete an electrical circuit with the fluid with which the sensor is in contact; and the reference electrode 323 may be optionally used to determine, by difference or otherwise, a voltage associated with the electrochemical reaction occurring at the working electrode.

In some embodiments, the probe 30 (which may also be referred to as a sensor) may include a plurality of working electrodes and/or a plurality of counter electrodes and or a plurality of reference electrodes. In a specific embodiment, the probe may include three (3) working electrodes, three (3) counter electrodes, and one (1) reference electrode.

In some embodiments, the one or more electrodes may be positioned on an outer circumference of cannula. In other embodiments, the one or more electrodes may be positioned within one or more lumens within the cannula 305. In some embodiments, each of the one or more electrodes (the electrode(s) may also be referred to as a sensor) may be positioned separately within a lumen within the cannula 305.

Figure 7:
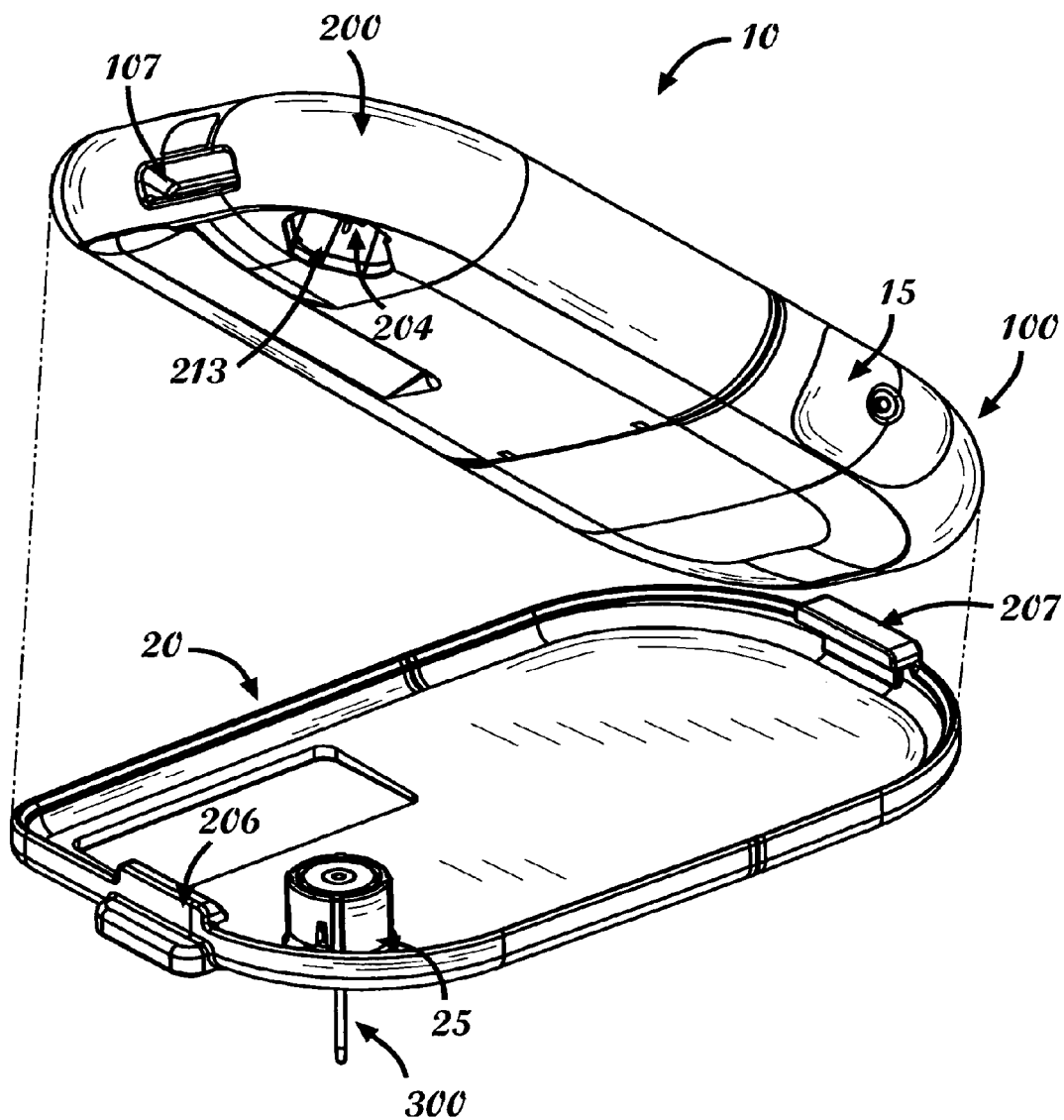
FIG. 7 shows a spatial view of the patch before connection to cradle according to some embodiments of the disclosure.

FIG. 7 shows a spatial view of patch 10 and cradle 20 before connection of the patch to the cradle, and include structure similar to structure described above, and as such, includes the same corresponding reference numbers. The patch 10 may include recesses (one recess 107 is shown) located at both sides of the patch, the recesses are configured to receive corresponding connection means such as snaps 206 and 207 of the cradle 20. The patch 10 may further include the exit port 204 and a connecting lumen 213. After connection of the patch 10 to the cradle 20, the snaps 206 and 207 are engaged with the recesses and the connecting lumen 213 pierces a septum of tip 300 residing in the well 25.

Figure 8:
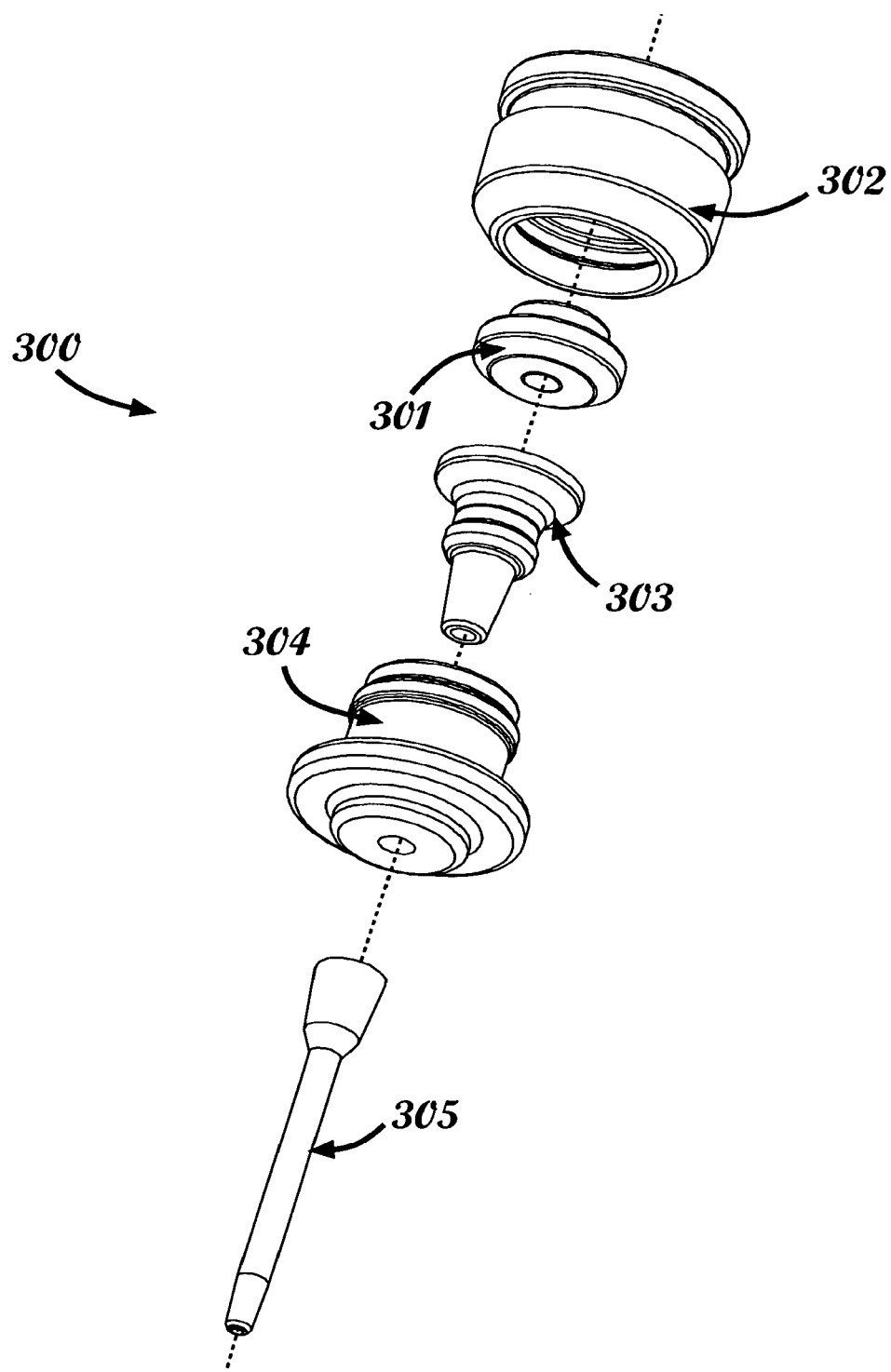
FIG. 8 shows a spatial view of the tip components before assembly according to some embodiments of the disclosure.

FIG. 8 shows a spatial view of tip 300 components before assembly, according to some embodiments of the present disclosure. The tip 300 may be comprised of a cover 302, a septum 301, a bushing 303, a cannula housing 304, and a cannula 305. The cannula 305 may include a proximal portion and a distal portion. The distal portion may be configured for residing within the body of the patient upon insertion of the tip to the body. The proximal portion may be configured for residing within the cannula housing 304 and including, in some embodiments, a conical widening end that is aligned with a conical shaped bushing 303. The bushing 303 is preferably rigidly connected to the cannula 305 and to the inner surface of the housing 304. The septum 301 may be placed on the bushing 303 and within the cover 302. The septum 301 may be made of a self-sealable material (e.g., rubber, silicone, etc.) providing sealing to the cannula 305 and configured to be pierced by a connecting lumen, upon connection of a patch, for example, providing fluid communication between a reservoir, located within the patch, for example, and the cannula 305. The cover 302 may be configured to be received (e.g., via a snap-fit arrangement) within the well of the cradle.

Figure 9A:
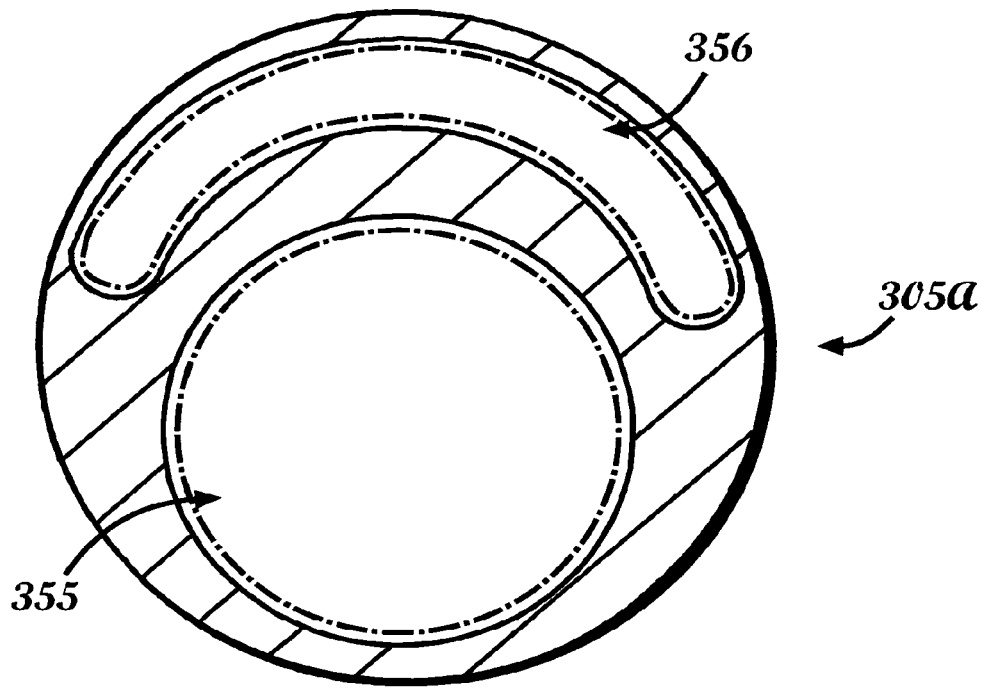
FIGS. 9a-b show a transverse cross sectional view of two preferred configurations of the cannula that includes multiple lumens according to some embodiments of the disclosure.
Figure 9B:
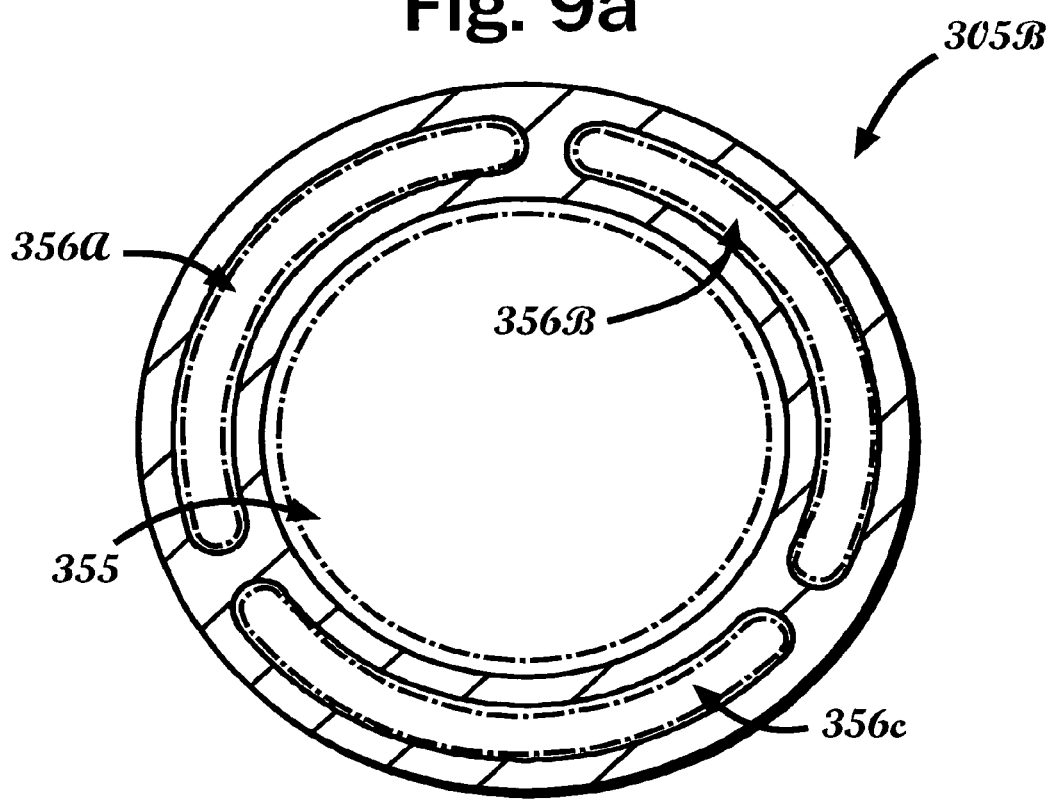

FIGS. 9a-b show a transverse cross sectional view of a multi-lumen cannula 305 according to some embodiments. The cannula 305 may include a lumen providing passageway for fluid (e.g., insulin) delivery (being a portion of the pump), and one or more additional lumens for providing one or more electrodes or probe (being a portion of the sensing apparatus).

In some embodiments, the cannula or tip may be characterized in length of about 6 mm, 9 mm, or 12 mm. In further embodiments, in which the tip is inserted to the body non-perpendicularly (i.e., the cannula or tip are tilted by an angle ($\alpha$) in respect to the skin surface), the cannula or tip can be even longer. For example, penetrating to a perpendicular depth of about 6 mm within the subcutaneous tissue with $\alpha=45°$, can be carried out with a cannula or tip having the portion within the body characterized by length of about 8.5 mm (i.e., 6/cos(45)). Having a lengthier portion of the cannula or tip within the body, may enlarge the contact surface of the one or more electrodes (or probe) with the analyte, and improve analyte monitoring.

In some embodiments, the one or more lumens providing the one or more electrodes (or the one or more electrodes themselves) may be shorter (e.g., by about 3 mm) than the lumen providing passageway for fluid delivery or the cannula itself. In some embodiments, the one or more additional lumens may include an opening/window (e.g., longitudinal) providing a direct contact between the surrounding (e.g., ISF) and the one or more electrodes. In some embodiments, the one or more lumens which include a longitudinal opening (for example) may be closed/sealed at their distal end.

Some embodiments of the present disclosure, may enable maintaining a distance (e.g., about 3 mm) separating apart between the fluid dispensing location (e.g., the distal opening of the cannula) and the analyte sensing location (e.g., contact area between the one or more electrodes and the body). In some embodiments, the outer surface of the one or more additional lumens may be provided with a plurality of holes/openings exposing the active surface (sensing surface) of the one or more electrodes to the ISF, for example.

FIG. 9a specifically illustrates a cannula 305a with two lumens, a first lumen 355 for fluid delivery and a second lumen 356 providing the one or more electrodes (or probe). In this configuration, the one or more electrodes may be printed on a planar probe provided by one lumen as further shown schematically in FIGS. 12a and 12b and spatially in FIGS. 25a-b and FIG. 26, for example. In some embodiments, the shape of the cannula 305a may be substantially circular, the first lumen 355 may be substantially circular and the second lumen 356 may be substantially arched. In some embodiments, the cannula 305a may have a "D" shape, wherein the first lumen 355 may be substantially circular and the second lumen 356 may be substantially planar or having a substantially rectangular shape. In some embodiments the one or more electrodes may each be provided by a separate lumen as shown schematically in FIGS. 12c and 12d and spatially in FIGS. 34a-c, for example. In some embodiments, the one or more electrodes may be embedded within the material of the walls of the cannula 305b, as illustrated in FIG. 9b. For example, lumens (may be also referred-to as "grooves" or "recesses") may be formed in the cannula's wall(s). These lumens (designated in FIG. 9b as 356a, 356b, 356c, for example) may be filled with conductive material. Alternatively, the one or more electrodes may be deposited within these lumens via at least one of vapor deposition, sputtering, painting, printing, replication, electro-less deposition, or any other method or technique known in the art, or any combination thereof.

Referring to FIG. 9b, a cannula 305b with four lumens is specifically illustrated. A first lumen 355 for fluid delivery and additional three (3) lumens 356a, 356b, and 356c are provided. The additional three (3) lumens may include three (3) electrodes, for example, a working electrode, a counter electrode and a reference electrode. In some embodiments, the cannula may include three (3) lumens, one for fluid delivery and an additional two lumens where each includes one electrode—a working electrode and a counter electrode, for example. In some embodiments, more than one electrode of each kind may be provided (e.g., three (3) working electrodes, three (3) counter electrodes, and one (1) reference electrode). In some embodiments, each electrode may be provided in a separate lumen. In some embodiments, the shape of the cannula 305b may be substantially circular, the first lumen 355 may be substantially circular and the one or more additional lumens 356a, 365b, 365c may be substantially arched. For example, the first lumen may be centered within the cannula 305b and the one or more lumens may be located on an outer circumference of the cannula, encircling the first lumen. In some embodiments, the one or more electrodes may be embedded within the material of the walls of the cannula 305b. Any other combinations of shapes of cannula and/or lumens may be implemented.

Figure 10:
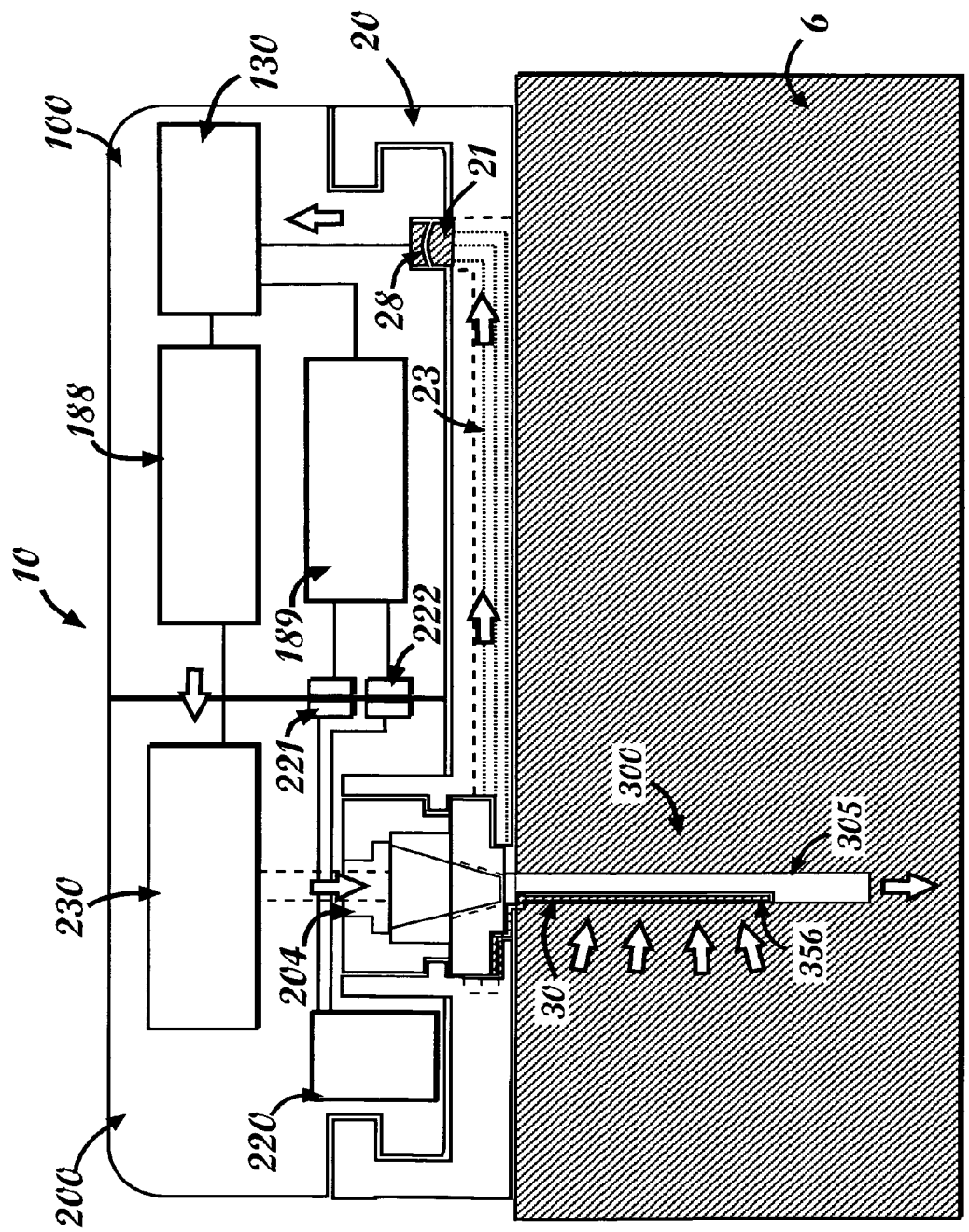
FIG. 10 shows schematic presentation of the dual function (sensing and dispensing) patch which comprises a reusable part and a disposable part, according to some embodiments of the disclosure.

FIG. 10 illustrates schematically the dual function ("sensing and dispensing") patch 10 according to some embodiments. The structure/elements of patch 10 include similar structure/elements of earlier described embodiments in other figures, and accordingly, refer to the same reference numbers for the similar structure. The two part patch 10 may be removably secured to the cradle 20 which may be rigidly connected to the tip 300, after insertion of the tip to the body of the patient. In some embodiments, the cradle 20 may include one or more electrical wires 23 and/or other conducting elements, and one or more RP connectors and/or contacts (e.g., electrical connectors to the reusable part) 21. The wires 23 and/or other conducting elements may be embedded within the cradle (and/or disposed on the cradle). The connector(s) 21 may be coupled with connector(s) 28 included in the reusable part 100. The tip 300 may include a cannula 305 having at least two lumens including a first lumen (e.g., 355 as illustrated in FIGS. 9a-b, for example) providing passageway for fluid delivery and one or more other lumens (e.g., 356 or 356a-c as illustrated in FIGS. 9a-b, for example) including the one or more electrodes or probe 30. The one or more electrodes preferably, continuously sense glucose levels within the body 6 (e.g., at the interstitial fluid (ISF) of the subcutaneous tissue). In some embodiments, the one or more lumens may include a longitudinal opening providing a direct contact between the ISF, for example, and the one or more electrodes (as illustrated by the arrows).

In some embodiments, the power source (e.g., battery) 220 may be located within the disposable part. In some embodiments, the power source may reside in the reusable part and may be rechargeable and/or replaced periodically. In some embodiments, the power source may reside in the cradle. In some embodiments, the pump and analyte sensing apparatus may be shared between (at least) the reusable part 100 and the disposable part 200. In some embodiments, electrical connectors 221, 222 (RP-DP connectors) may be provided at the disposable part and the reusable part (respectively), for maintaining electrical connection between the power source 220 located in the disposable part 200 and the electronics 189 or processor 130 located in the reusable part 100. The connectors 221 and 222 may, in some embodiments, establish electrical communication related to the sensing apparatus, for example, transmitting glucose readings from the probe, via the disposable part to the reusable part.

Upon processor 130 assessment (or determination) of delivery commands/instructions, the driving mechanism 188 may be activated and fluid may be expelled from reservoir 230, through the exit port 204 and the cannula 305 into the body of the patient 6 (e.g., to the subcutaneous tissue). The one or more electrodes (and/or probe 30, which may comprise the one or more electrodes) may be positioned within the body of the patient 6 upon insertion of the tip to the body. In some embodiments, the one or more electrodes may sense analyte levels within the body of the patient via electrochemical reactions generating an electrical current. This current may be transferred (designated by arrows) to the processor 130 via the wires 23 and the connectors 21, 28. For example, the one or more electrodes may sense glucose levels within the subcutaneous tissue by oxidation of glucose, generating an electrons (electrical) current, as well known in the art.

The current (e.g., signals) may be converted by the processor into glucose levels. Glucose levels may be presented as glucose readings on a screen located on a remote control or on the patch unit, for example.

Figure 11:
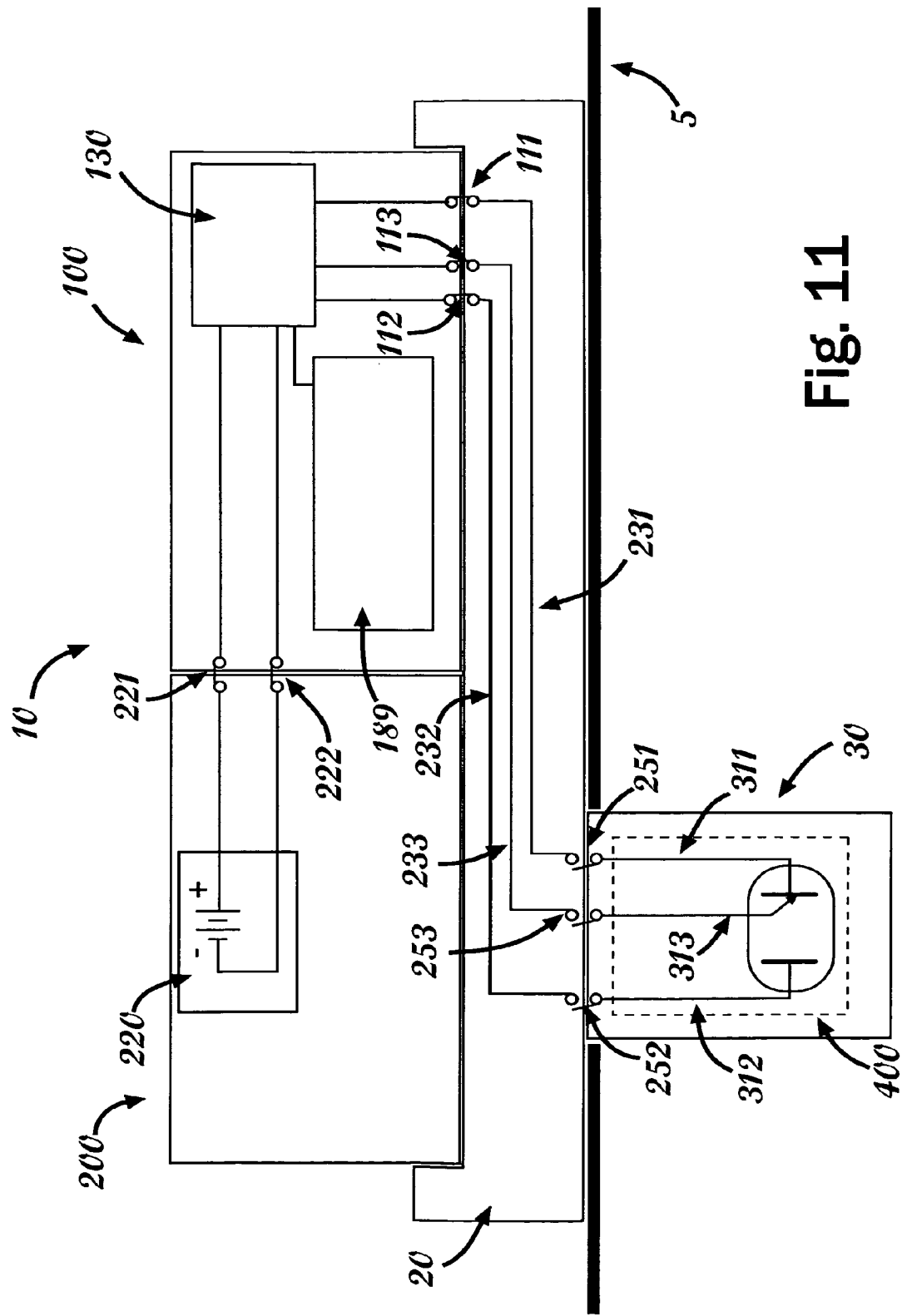
FIG. 11 shows the electrical wiring and connections of the sensing apparatus according to some embodiments of the disclosure.

FIG. 11 illustrates electrical connections of the sensing apparatus, according to some embodiments of the present disclosure. Accordingly, when inserted into the body of the user, the tip may be rigidly connected to cradle 20 which may be secured (e.g., adhered) to the patient's skin 5. In some embodiments, the one or more electrodes of the probe 30, for example (e.g., working electrodes, counter electrodes, and optionally, reference electrodes) may be embedded within a polymer 400 (e.g., flexible polymer). Each electrode may be connected to one or more wires (and/or conducting elements) located on the probe ("probe wires"), for example wires 311, 312, and 313. The probe wires may be connected to one or more probe-cradle connectors, for example connectors 251, 252, and 253, providing electrical communication between the probe wires and one or more wires or other conducting elements ("cradle wires") provided within (and/or on) the cradle, for example wires 231, 232 and 233. In some embodiments, one or more electrical connectors/contacts, for example connectors 111, 112, and 113, may be provided on the cradle for maintaining electrical communication between the cradle wires and RP wires located within the reusable part 100 providing electrical communication with processor 130.

The locations of the various wires and various connectors on probe 30, cradle 20, and reusable part 200 are shown in the figure as an example only. In other embodiments, only a portion of the wires and connectors may be implemented, such as for example establishing a direct electrical connection between the probe and the reusable part, via the cradle. The one or more connectors 111, 112 and 113 and/or 251, 252 and 253 may be configured to be sealed (or embedded) when the patch unit is disconnected from the cradle, as will be further described in FIG. 27, for example. In some embodiments, the cradle may include an amplifier for amplifying the signals conveyed from the electrodes to the processor, or further include other electronic components required for its function. In some embodiments, the cradle may include a power source enabling continuous (or periodic) operation of the electrodes/probe even when the patch is disconnected. In such as embodiment for example, desirable hydrogen peroxide decomposition may be maintained (at least to some extent).

FIGS. 12a-d show longitudinal cross sectional views of the tip 300 having one or more electrodes. Components of the tip 300 are similar to those shown and described in FIG. 8.

Figure 12A:
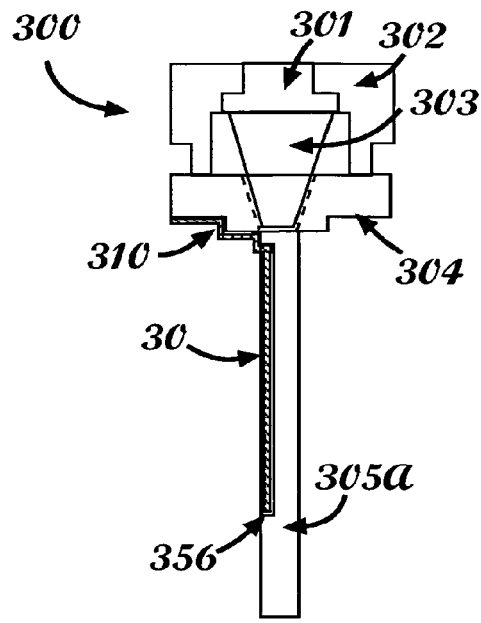
FIGS. 12a-d show longitudinal cross sectional views of the tip that includes a cannula and sensing electrodes according to some embodiments of the disclosure.
Figure 12C:
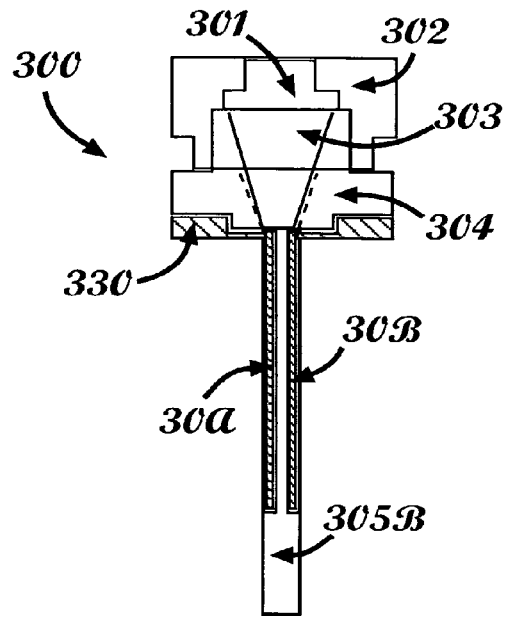
Figure 12B:
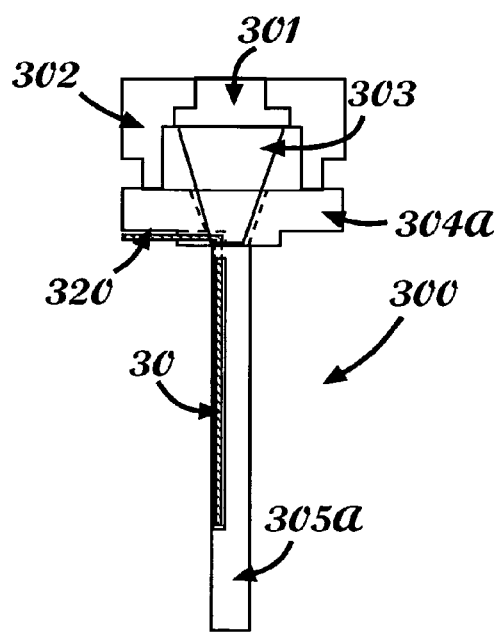

In some embodiments, as illustrated in FIGS. 12a-b, the one or more electrodes may be configured (e.g., printed or disposed) on a planar probe 30 provided by the second lumen 356 of a double lumen cannula 305a. In this configuration, the first lumen 355 may serve as a fluid passageway and the second lumen 356 may serve as a "pocket" for accommodating/housing and/or supporting the probe 30. In some embodiments, the second lumen 356 may be provided with a longitudinal opening (window) enabling direct contact between the ISF, for example, and the one or more electrodes provided by the second lumen 356. The probe 30 may further include electrical conductive wires, and/or connectors.

FIG. 12a illustrates a specific example in which the probe is bent several times over the cannula housing 304 such that the electrical wires and/or connectors 310 are in close (e.g., mechanical, physical or press-fit) contact with the bottom side of the cannula housing 304. Detailed illustrations of this configuration are shown in FIGS. 30a-32c. FIG. 12b illustrates a specific example in which the cannula housing 304a includes a slot (window), for example at its bottom side, as further shown in FIGS. 24-26. In this configuration, the probe is folded once and resides within the slot of the cannula housing 304a such that the electrical wires and/or connectors 320 are in close contact with the bottom side of the cannula housing 304.

In further embodiments, the wires and/or connectors (e.g., 310 or 320) for the probe may form an annular shape. For example, the slot may be formed annularly, receiving an annular wire/connector in close contact with the bottom or side of the cannula housing.

Figure 12D:
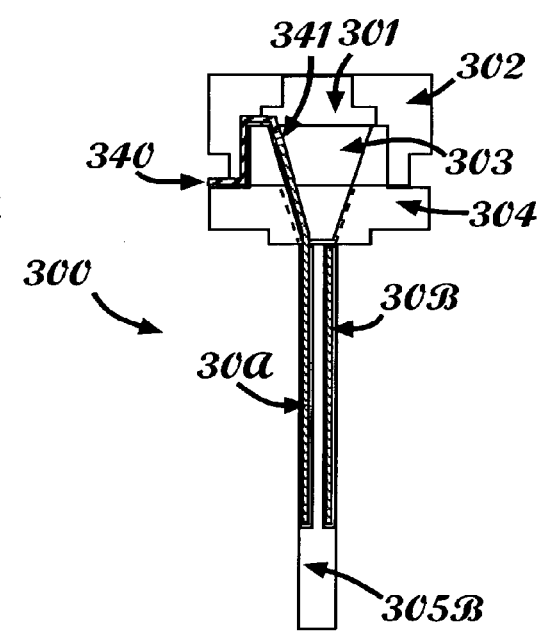

In some embodiments, as illustrated in FIGS. 12c-d, the one or more electrodes are located apart from each other such that each electrode corresponds to (provided on or within) a separate lumen (30a, 30b, for example, referring to FIG. 12c-d).

FIG. 12c illustrates a specific example in which a multi-lumen cannula 305b includes four (4) lumens: a first lumen for providing a passageway for fluid dispensing, and additional three (3) lumens (shown only two lumens) for providing three (3) electrodes (shown only two electrodes 30a and 30b). The electrodes 30a, 30b are preferably connected by conductive wires to a connector plate 330 located at the bottom side of the cannula housing 304. The connector plate 330 provides electrical communication between the electrodes and the connectors located on the plate as further shown in FIGS. 35a-37b. In some embodiments, the connector plate may be formed as a circular or annular plate ("connector ring"). In some embodiments, the conductive wires and the connector plate may be formed as a single integral conducting element. FIG. 12d illustrates a specific example in which a multi-lumen cannula 305b includes four (4) lumens: a first lumen for providing a passageway for fluid dispensing and additional three (3) lumens (shown only two lumens) for providing three (3) electrodes (shown only two electrodes 30a and 30b). The electrodes 30a, 30b can be connected by folded (e.g., bent, twisted, curved) conductive wires and connectors 340 located on an upper side of the cannula housing 304. Upon assembly of the tip's components, electrical wires 341 that connect the electrodes 30a, 30b and the connectors 340 can be provided through bushing 303 and bent underneath the cover 302 and the septum 301 as further shown in FIGS. 40-42. In some embodiments, the electrodes (e.g., 30a, 30b) and/or conductive wires and/or connectors (340 and/or 341) may be formed as a single integral conductive element. Some (or all) of these conducting elements may be embedded within the tip components (e.g., the connector 341 may be embedded, at least in part, within the cannula housing 304 and the bushing 303).

Figure 13A:
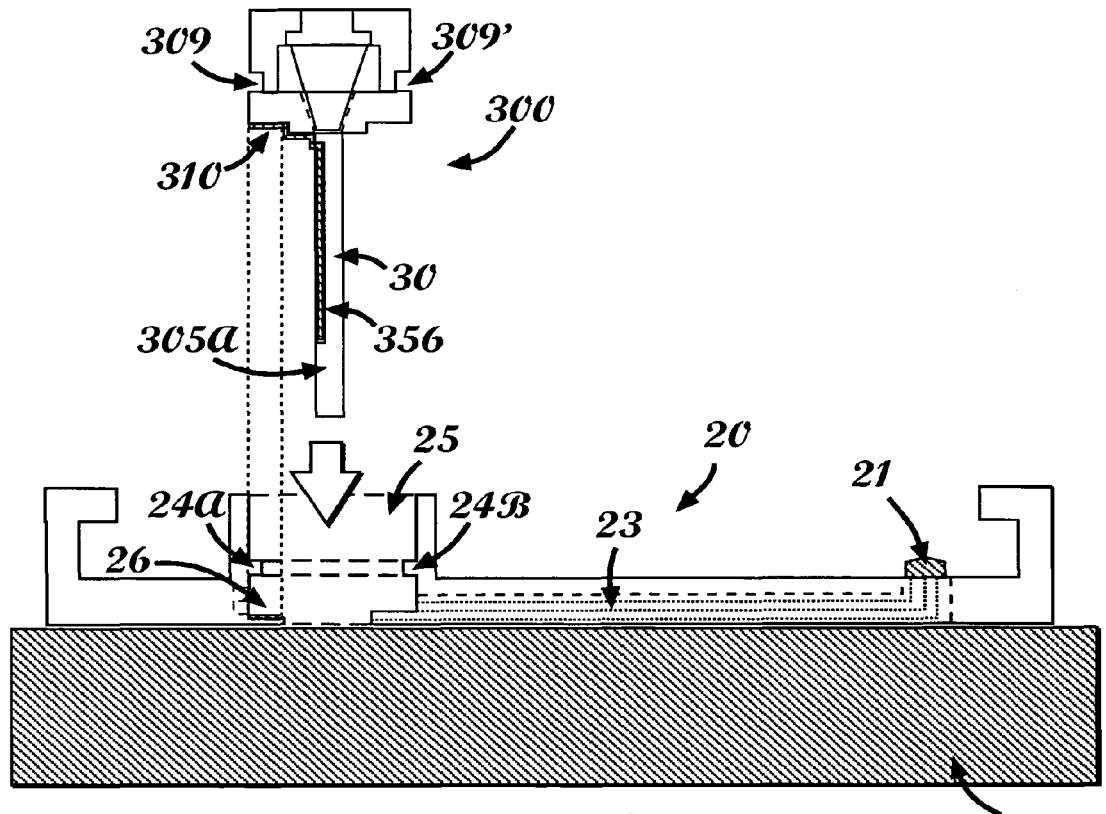
FIGS. 13a-b show a schematic presentation of a tip that comprises two lumens before (13a) and after (13b) insertion of the tip into the body, according to some embodiments of the disclosure.
Figure 13B:
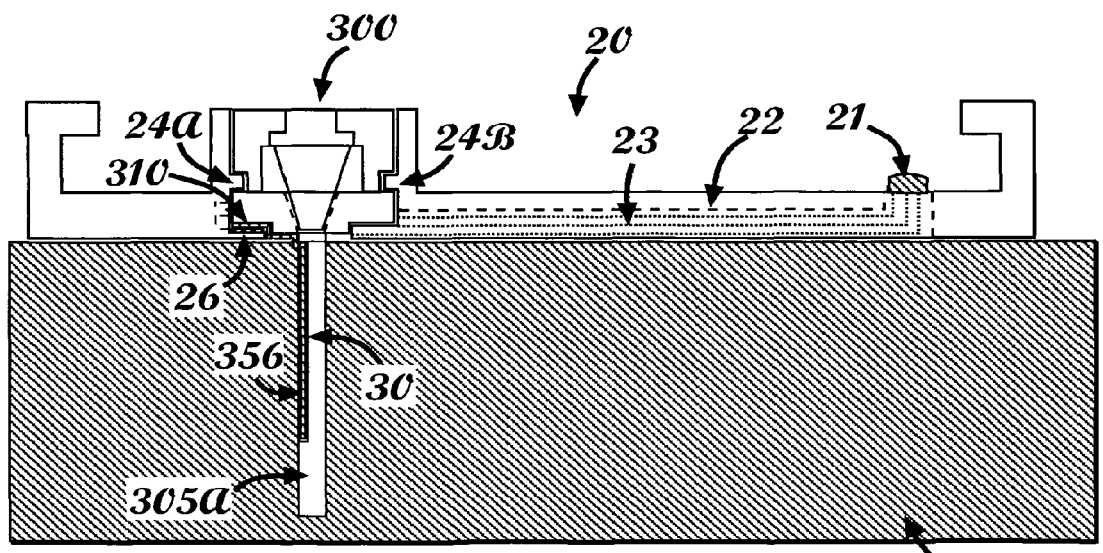

FIGS. 13a-b illustrate a schematic presentation of a tip 300 including one or more connectors 310, before (FIG. 13a) and after (FIG. 13b) insertion of the tip 300 into the body 6 (e.g., subcutaneous tissue). The tip 300 includes a double-lumen cannula 305a as described in one or more previous descriptions above.

In some embodiments, the cradle 20 may be used and may be secured to the patient's skin before insertion of the tip 300 to the body, for example, the cradle may be adhered to the skin of the patient/user via an adhesive layer at the bottom side of the cradle. The cradle 20 may include an opening (e.g., a well) 25 to secure the tip 300 to the cradle 20 upon insertion of the tip to the body of the user. At least one anchoring mechanism may be provided for establishing a secure connection of the tip 300 to the cradle 20 after tip insertion. For example, one or more latches or protrusions 24a and 24b provided at the well 25 may be engaged with one or more recesses/grooves (e.g., an annular recess 309, 309') of the tip 300, forming a snap-fit arrangement (for example). In some embodiments, as illustrated in FIGS. 13a-b, the cradle connector(s) 26 may be located on the bottom side of the well 25, and upon insertion of the tip to the body of the patient, the tip connector(s) 310, as shown for example in FIG. 12a, are engaged with the cradle connector(s) 26 such that electrical current generated on the electrodes or probe 30 can be transmitted via cradle electrical wires 23 to the RP (via RP connector(s) 21). The well 25 and/or the tip 300 may be configured such that upon connection of the tip 300 to the well 25, the connectors 26 and 310 remain sealed. For example, the well may include two O-rings, one (1) at its bottom side and another at its upper side, both substantially sealing the connectors.

As noted above, the RP connector(s) 21 provide electrical communication between the cradle 20 and reusable part 100 of the patch after connection of the patch to the cradle and may be located, for example, on a base of the cradle, as shown in FIGS. 13a-b. In some embodiments, the connector(s) 21 may be located on a cradle latch, or may be located on a side wall of the cradle, as further illustrated hereinafter. The cradle electrical wires 23 and RP connector(s) 21 may be embedded within the cradle. The RP connector(s) 21 may be configured to be sealed when the patch unit is disconnected from the cradle, as will be further described in reference to FIGS. 27a-b.

Figure 14A:
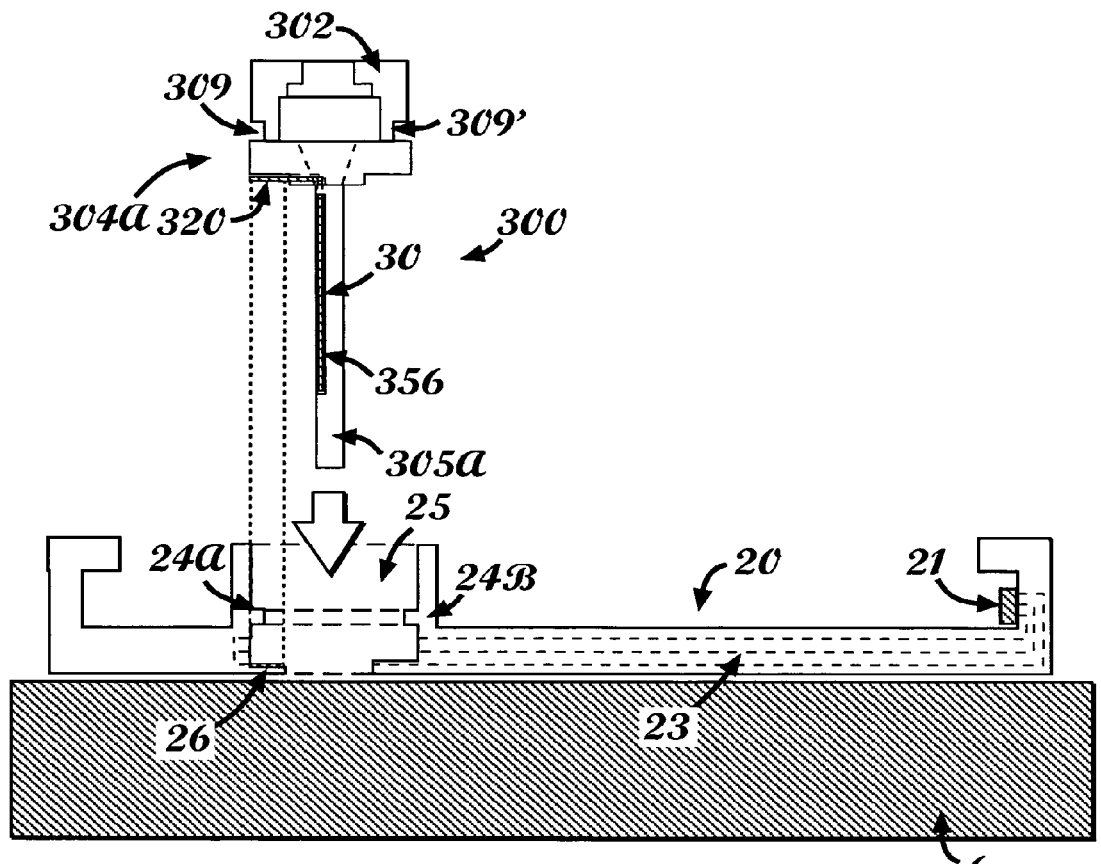
FIGS. 14a-b show a schematic presentation of a tip that comprises two lumens before (14a) and after (14b) insertion of the tip into the body according to some embodiments of the disclosure.
Figure 14B:
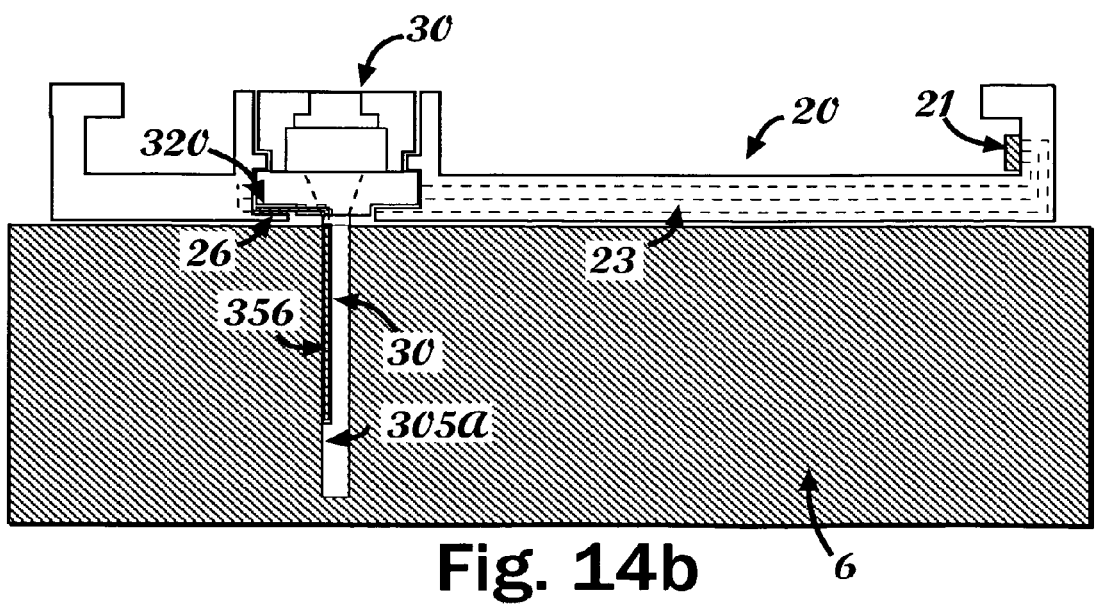

FIGS. 14a-b illustrate a schematic presentation of tip 300 including one or more connectors 320, as shown for example in FIG. 12b, before (FIG. 14a) and after (FIG. 14b) insertion of tip 300 into the body 6 of the patient (e.g., to the subcutaneous tissue), where the one or more connectors 320 may be located at the bottom side of cannula housing 304a. The one or more connectors 320 configured to engage cradle connector(s) 26 located on the bottom surface of the well 25.

In some embodiments, illustrated in FIGS. 14a-b, the RP connector(s) 21 may be located on a cradle latch and/or on a side wall of the cradle. The RP connector(s) 21 may be configured to be sealed when the patch unit is disconnected from the cradle, as will be further described in reference to FIGS. 27a-b.

Figure 15A:
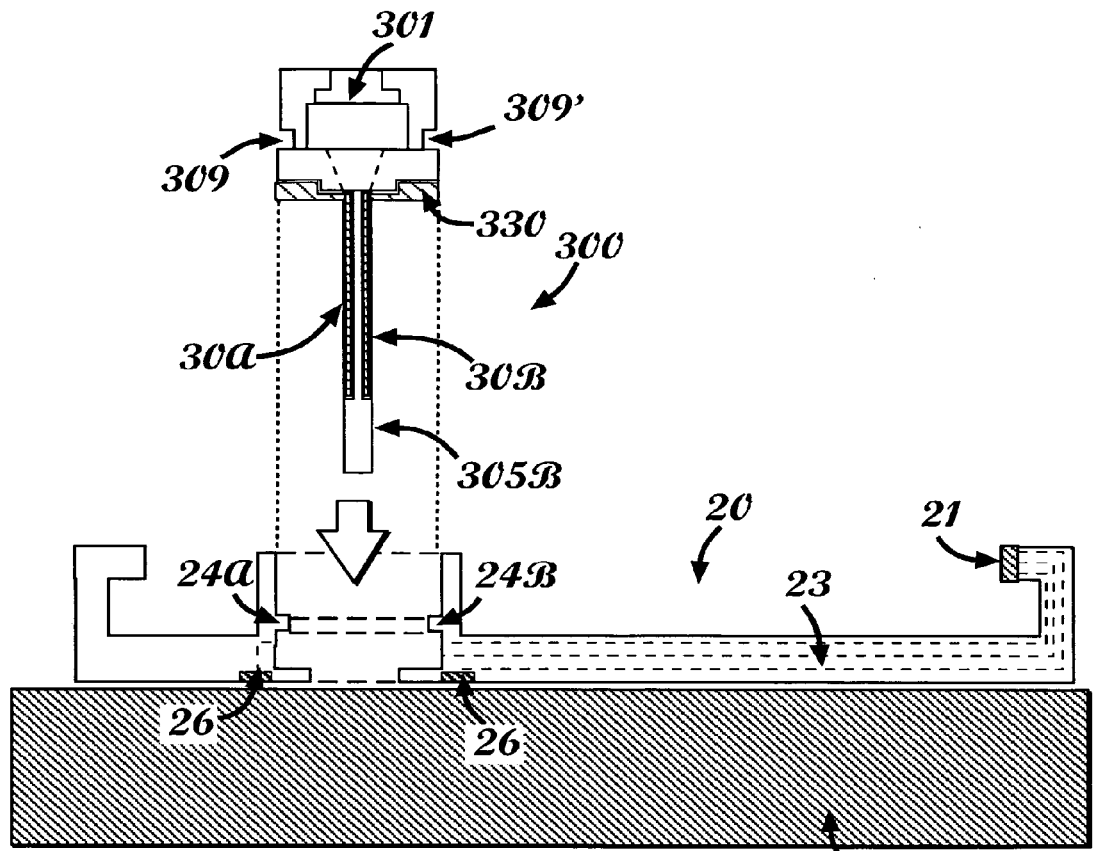
FIGS. 15a-b show a schematic presentation of a tip that comprises more than two lumens before (15a) and after (15b) insertion of the tip into the body according to some embodiments of the disclosure.
Figure 15B:
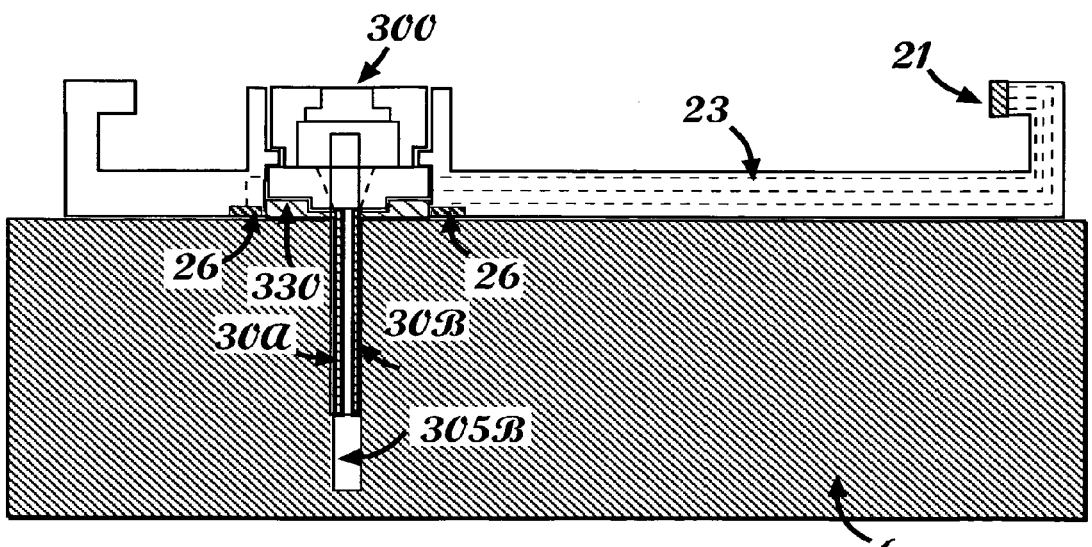

FIGS. 15a-b illustrate a schematic presentation of tip 300 including connectors plate 330, before (FIG. 15a) and after (FIG. 15b) insertion of tip 300 into the body 6 of the patient (e.g., to the subcutaneous tissue). The tip 300 may include four (4) lumens as shown, for example, in FIG. 12c, where a first lumen serves as fluid passageway and each of the three (3) additional lumens includes an electrode of the three (3) electrodes (shown only two electrodes 30a, 30b) which may be electrically connected to connector plate 330 located at the bottom side of cannula housing 304. The connector plate 330 configured to engage cradle connector(s) 26 located at the bottom of the side walls of the well 25.

Figure 16A:
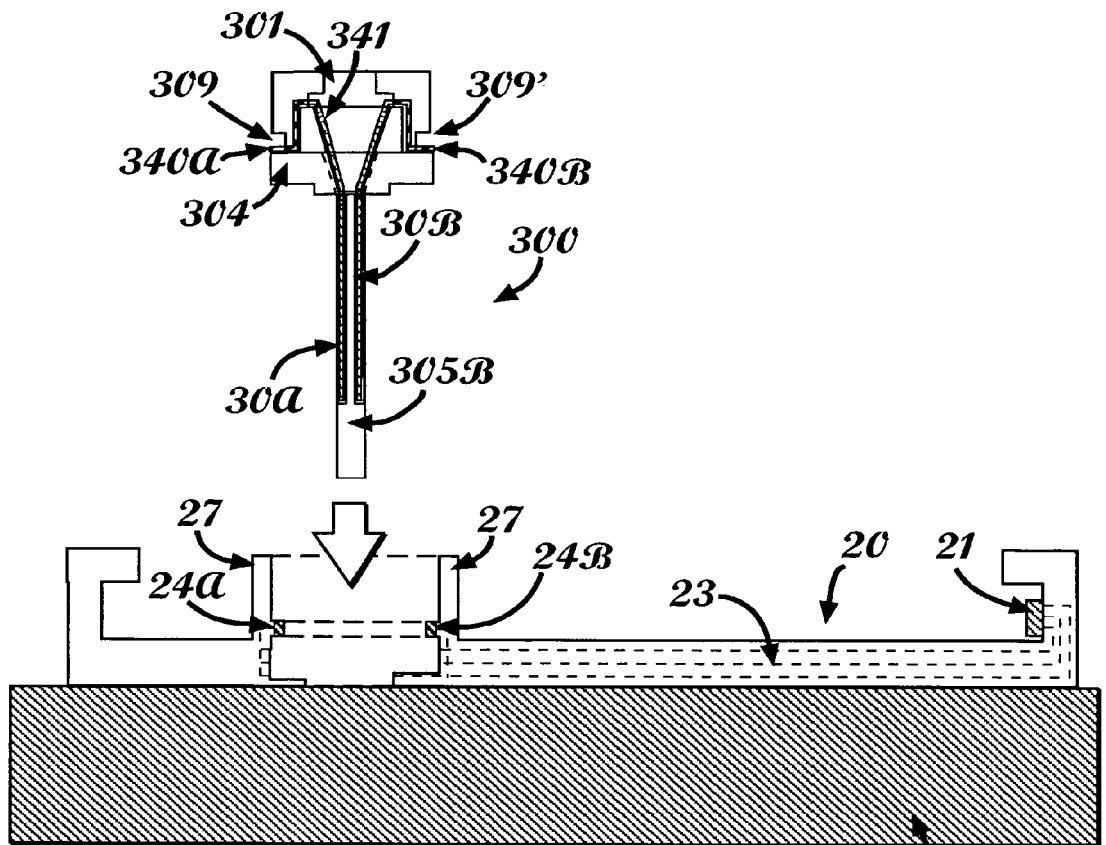
FIGS. 16a-b show a schematic presentation of a tip that comprises more than two lumens before (16a) and after (16b) insertion of the tip into the body according to some embodiments of the disclosure.
Figure 16B:
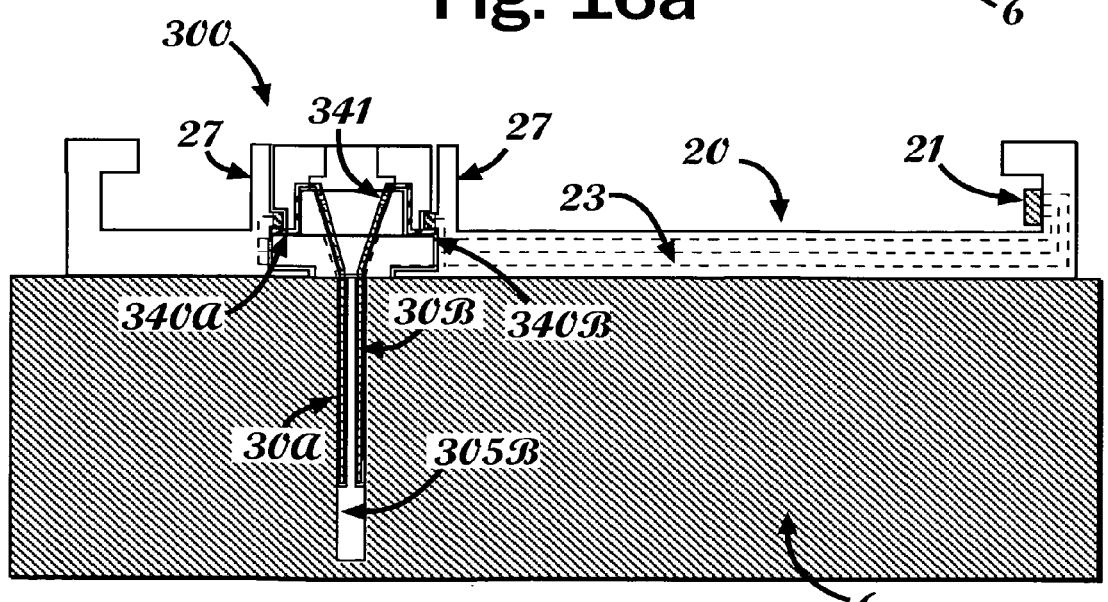

FIGS. 16a-b illustrate a schematic presentation of tip 300 including one or more connectors 340, before (FIG. 16a) and after (FIG. 16b) insertion of the tip into the body 6 of the patient (e.g., to the subcutaneous tissue). The tip 300 may include four lumens as shown for example in FIG. 12d, a first lumen serving as a fluid passageway and each of the three (3) additional lumens may provide (either within or on) an electrode out of the three (3) sensing electrodes (shown for example electrodes 30a and 30b in FIGS. 16a-b). The electrodes may be electrically connected to one or more connectors (shown for example connectors 340a and 340b), for example the three (3) electrodes may be connected to three (3) connectors.

In some embodiments, the protrusions 24a and 24b may include electrical connectors ("well connectors"), such that after insertion of the tip 300 to the body 6 of the patient, the one or more tip connectors (e.g., 340a, 340b) may be engaged with the one or more well connectors.

Figure 17A:
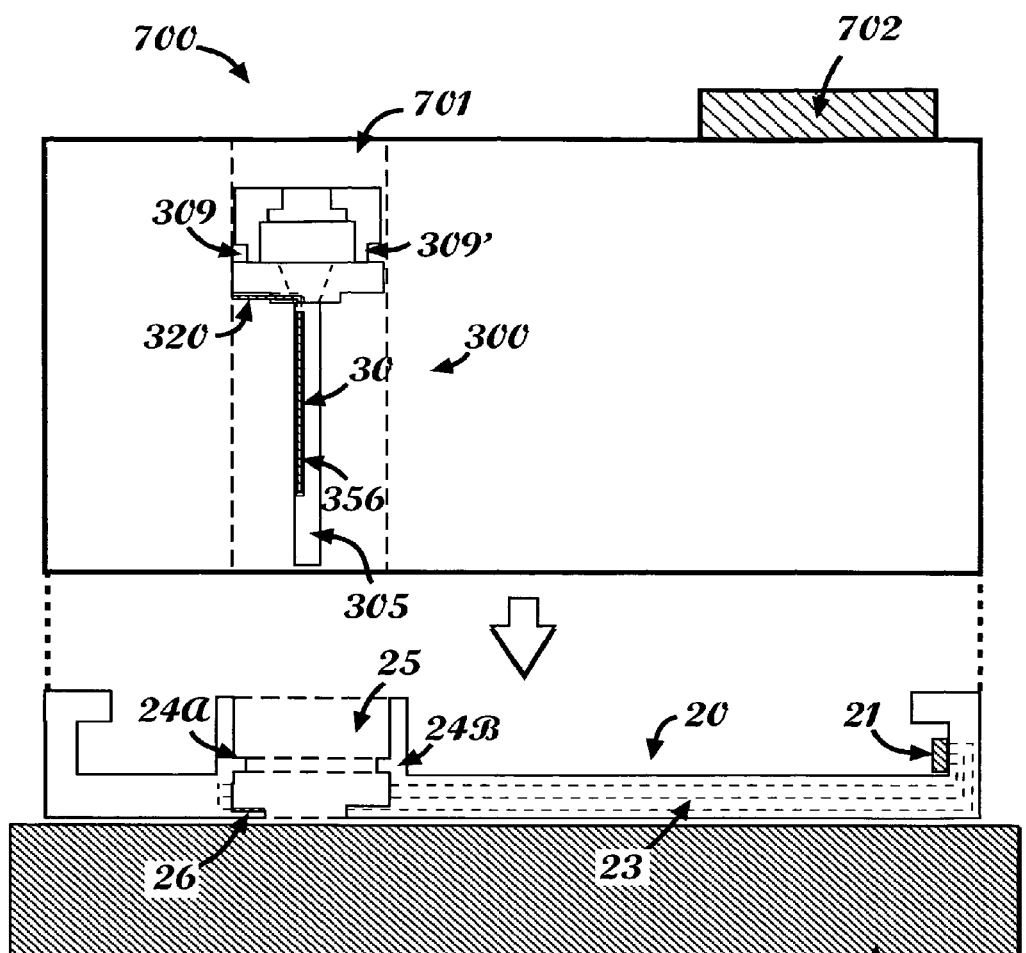
FIGS. 17a-b show insertion process of a tip into the body and connection of the tip to the cradle with the aid of an automatic inserter according to some embodiments of the disclosure.
Figure 17B:
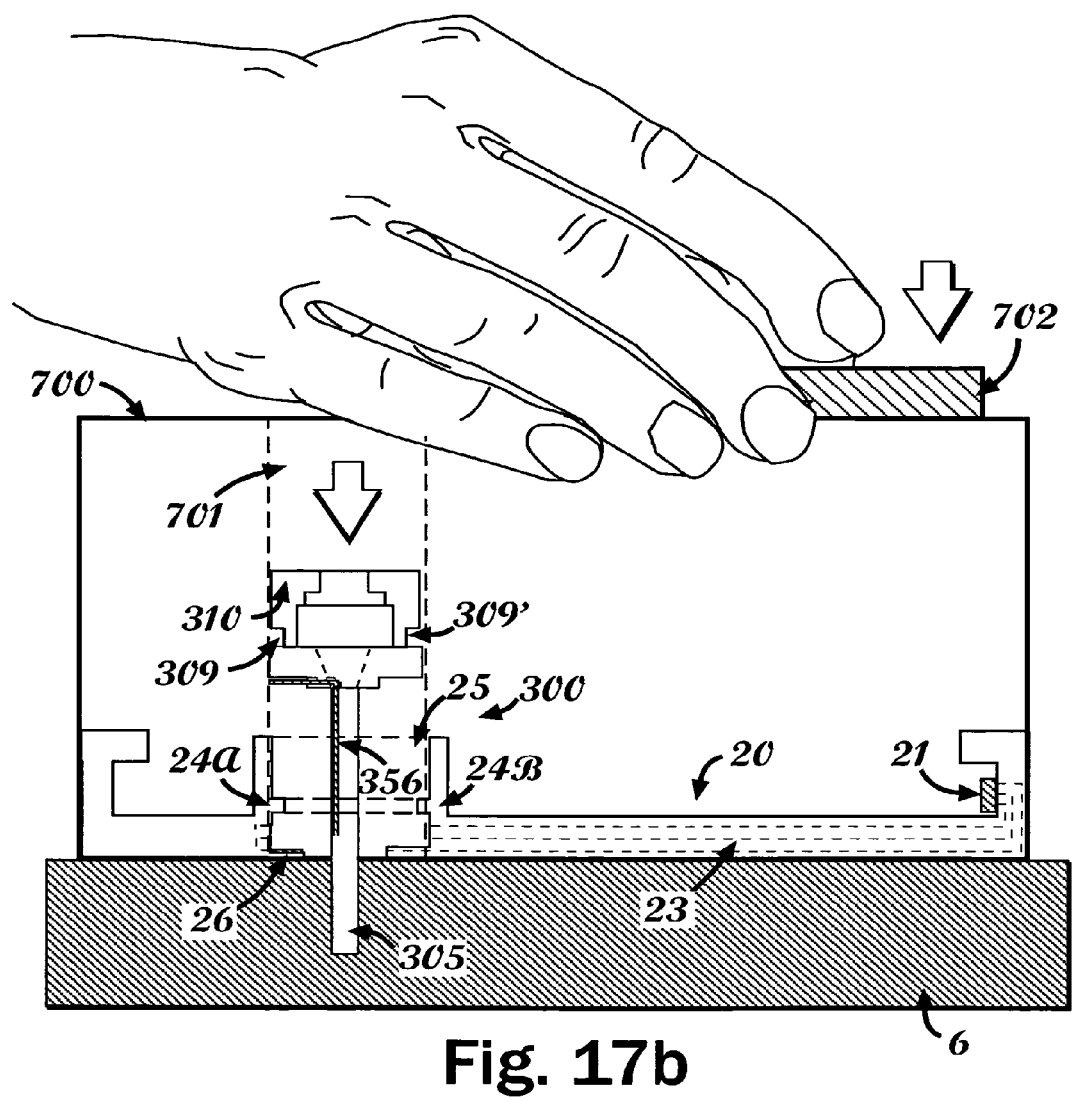

FIGS. 17a-b illustrate insertion of tip 300 into the body 6 of the patient, according to some embodiments of the present disclosure.

In some embodiments, an automatic inserter 700 may be used for inserting the tip 300 to the body 6 of the patient and connecting the tip 300 to the cradle 20. The inserter may include a slot (or receiving opening/recess) 701 configured for receiving a tip cartridge, having a tip, a tip protector and a penetrating member (i.e., a sharp needle). According to some embodiments, the tip cartridge is configured to align the tip with the well such that upon engagement of the tip within the well, the tip connectors contact the well connectors. An example of a tip cartridge is shown in FIGS. 50a-e and 51 and an example of an inserter is shown in FIG. 52. As illustrated in FIG. 17a, before insertion to the body the tip cartridge may be loaded within the inserter 700 and positioned in the inserter slot 701. The cradle 20 may be secured (e.g., adhered) to the body 6 of the patient prior to the insertion process. In some embodiments, the cradle can be provided with different wells which may be slanted (or tilted) with respect to the cradle 20 at different angles to allow various penetration angles. Examples for such angular/tilted insertion are described in U.S. Patent Application Publication No. 2008/0319414, the disclosure of which is incorporated herein by reference in its entirety.

FIG. 17b illustrates an example for tip 300 insertion via the inserter 700. After the tip 300 is loaded onto (or within) slot 701, the inserter 700 may be coupled to the cradle 20. Upon operation of button 702, a spring loaded mechanism may fire the tip 300 through the well 25 into the body 6, such that the tip is engaged with the well and the electrical connectors 320 and 26 are also engaged. Current generated over the electrode(s) may be conducted via the connectors 320 (for example), 26 and the wires 23 to the RP (further via RP connectors 21). The arrow designated at the inserter slot 701 illustrates the movement direction of the tip 300 during insertion.

Figure 18A:
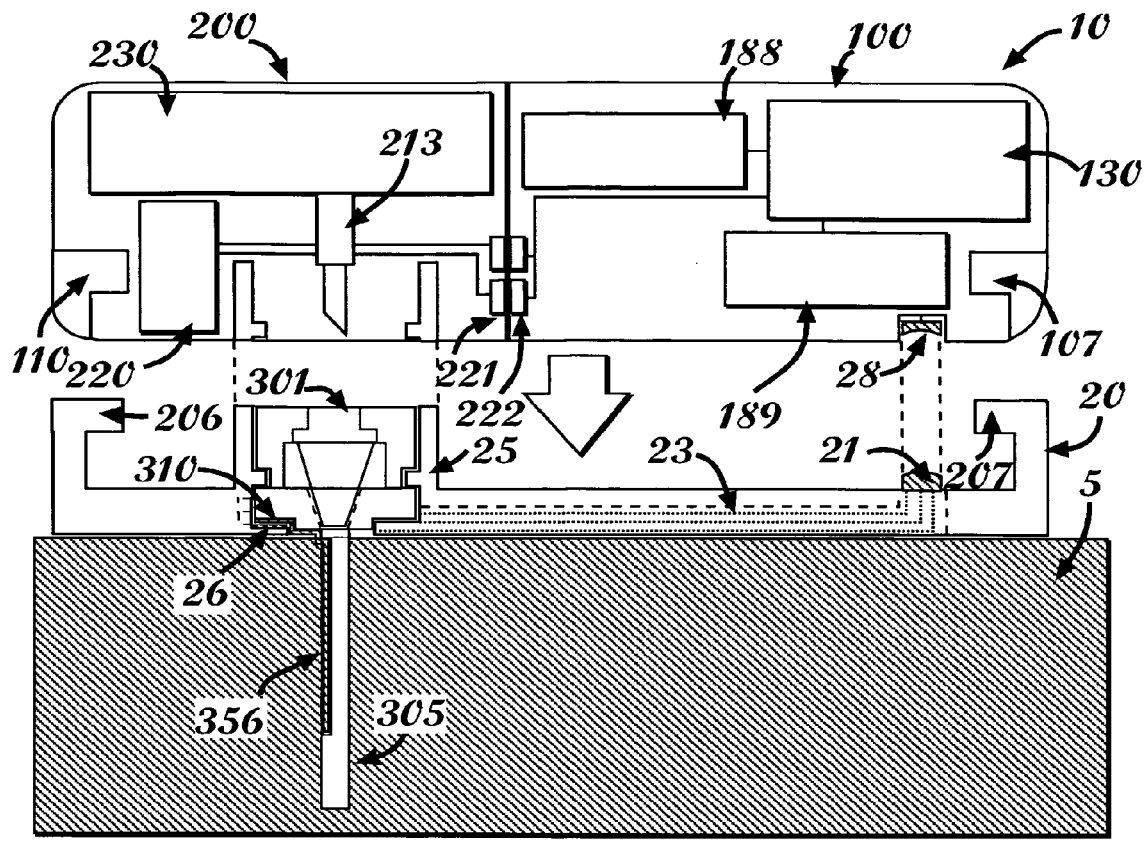
FIGS. 18a-b show the patch and cradle before (18a) and after (18b) connection of patch onto cradle according to some embodiments of the disclosure.
Figure 18B:
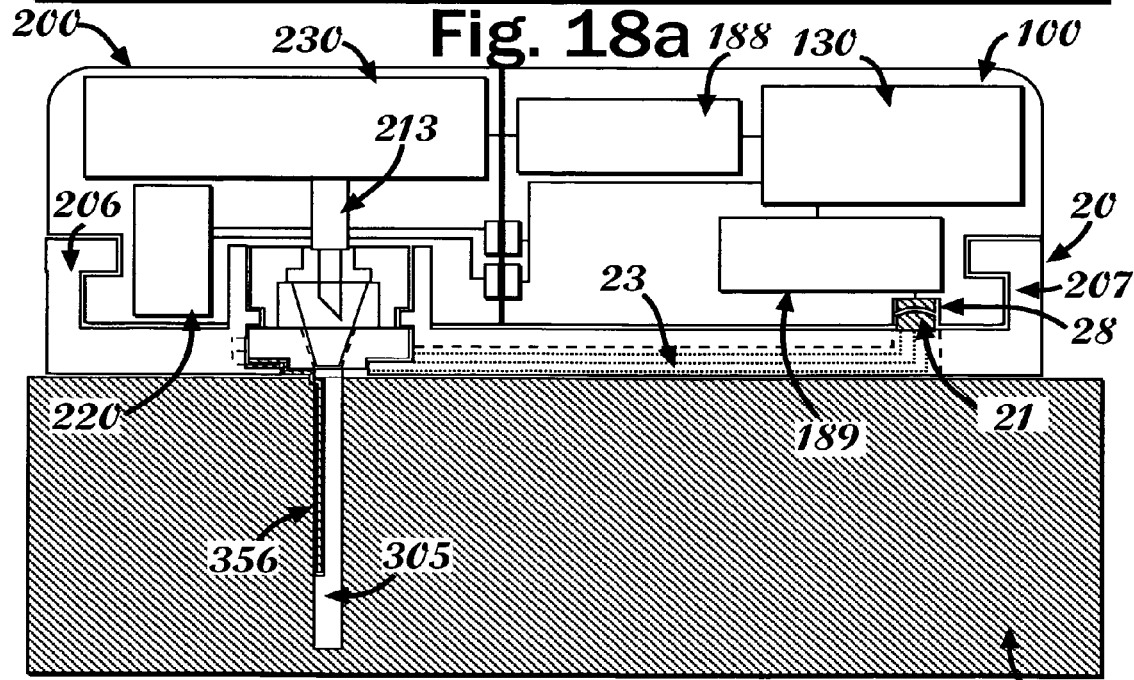

FIGS. 18a-b illustrate a patch 10 and a cradle 20, according to some embodiments of the present disclosure, before (FIG. 18a) and after (FIG. 18b) connection of the patch 10 to the cradle 20.

Figure 19:
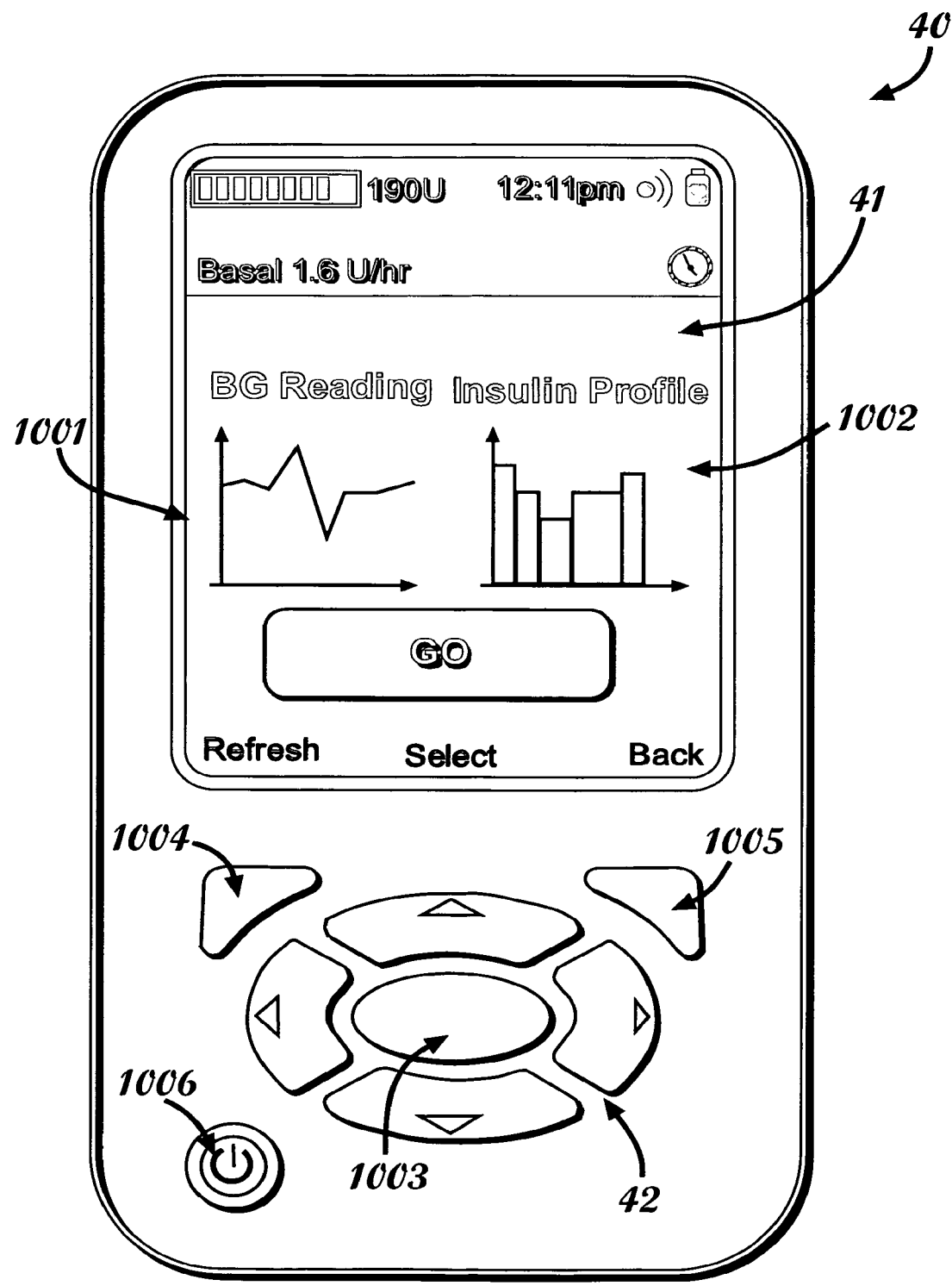
FIG. 19 shows an example of a remote control graphical user interface (GUI) and operating buttons according to some embodiments of the disclosure.

FIG. 19 illustrates an example of a user interface (UI) that may be used in various embodiments of the present disclosure. The UI may be provided, in some embodiments, on a remote control 40 and include a screen 41 and one or more keys, for example, navigation keys ("operating buttons") 42. The screen 41 may present data related to the sensing apparatus (e.g., glucose readings) and/or to the pump (e.g., insulin delivery profiles). In this example shown in FIG. 19, glucose readings are presented via curve/graph 1001 (entitled "BG Reasing") and insulin delivery profile (e.g., daily basal profile) is presented via bar graph 1002. The user may navigate between and/or within screen elements (e.g., displays, menus) using navigation keys 42 and/or soft keys 1003, 1004, 1005. The function of the soft keys may correspond to instruction indicated on the screen (in a soft key strip e.g., on the bottom of the screen) and may depend on the context of usage and the specific function currently active. In the example shown in FIG. 19, key 1003 corresponds to a "Select" function, key 1004 corresponds to a "Refresh" function, and key 1005 corresponds to a "Back" function. The user may use the navigation keys 42 and/or the soft keys 1003, 1004, 1005 to program and/or activate the pump and/or sensing apparatus. An on/off button/key 1006 may be provided for turning on or shutting down the remote control 40. Other remote controls may be used, for example implementing touch-sensitive screen, etc.

Figure 20A:
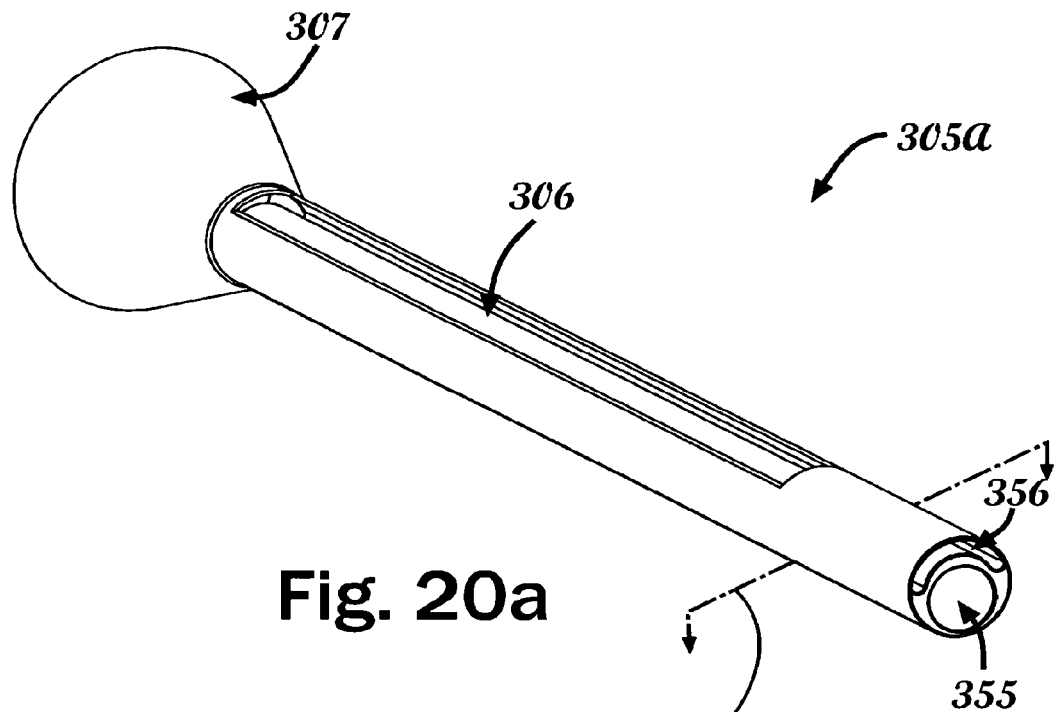
FIGS. 20a-b show a spatial view (20a) and a transverse cross sectional view (20b) of a double lumen cannula according to some embodiments of the disclosure.
Figure 20B:
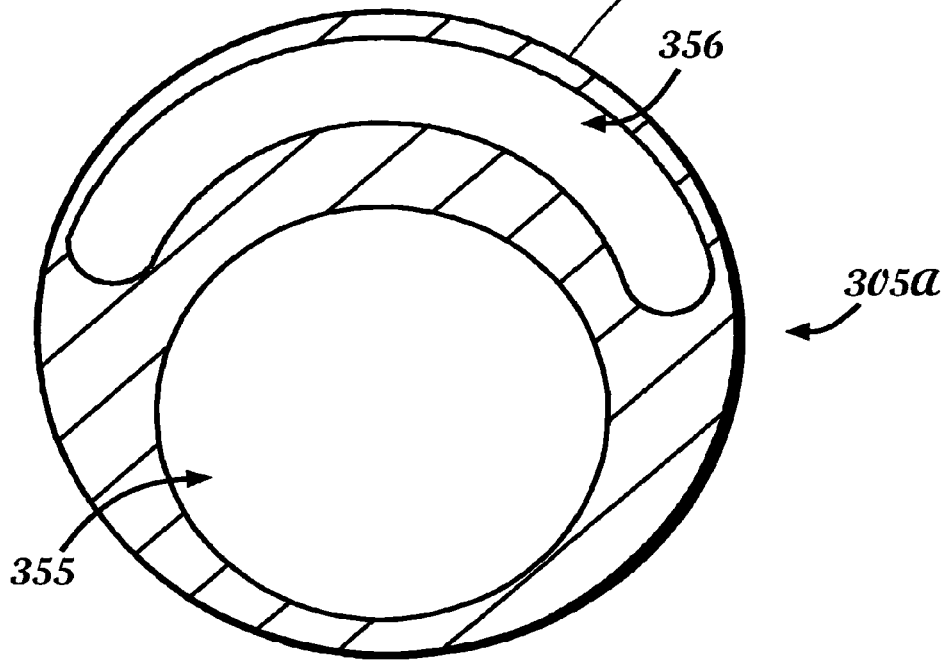

FIGS. 20a-b show a spatial view (FIG. 20a) and a transverse cross sectional view (FIG. 20b) of a tip having a double lumen cannula 305a, according to some embodiments of the present disclosure. As shown, the cannula 305a includes two lumens, a first lumen 355 providing passageway for insulin delivery and a second lumen 356 providing the sensing probe that contains/provides the one or more sensing electrodes. A longitudinal window 306 may be provided at the outer surface of the second lumen 356 enabling contact of interstitial fluid (ISF) within the body with the one or more sensing electrodes provided by the second lumen 356. The longitudinal window 306 enables exposure of the active surface of the one or more electrodes while mechanically holding (or supporting) the probe within the second lumen. For example, the distal portion of the window 306 may be configured with smaller dimensions (e.g., smaller diameter) than the proximal portion of the window 306, to enable mechanical support of the probe (or electrodes) within the lumen. In some embodiments, the outer surface of the second lumen may be provided with a plurality of holes or openings exposing the active surface of the one or more electrodes to the ISF, for example.

In some embodiments, the proximal portion of cannula 305a may be widened to acquire a conical shape configuration 307 precisely aligned with a corresponding conical bushing (as shown for example in FIG. 8). In some embodiments, the widening of the proximal portion of the cannula may be accomplished via heating (e.g., ultrasonic welding) and/or via any other techniques known in the art.

Figure 21:
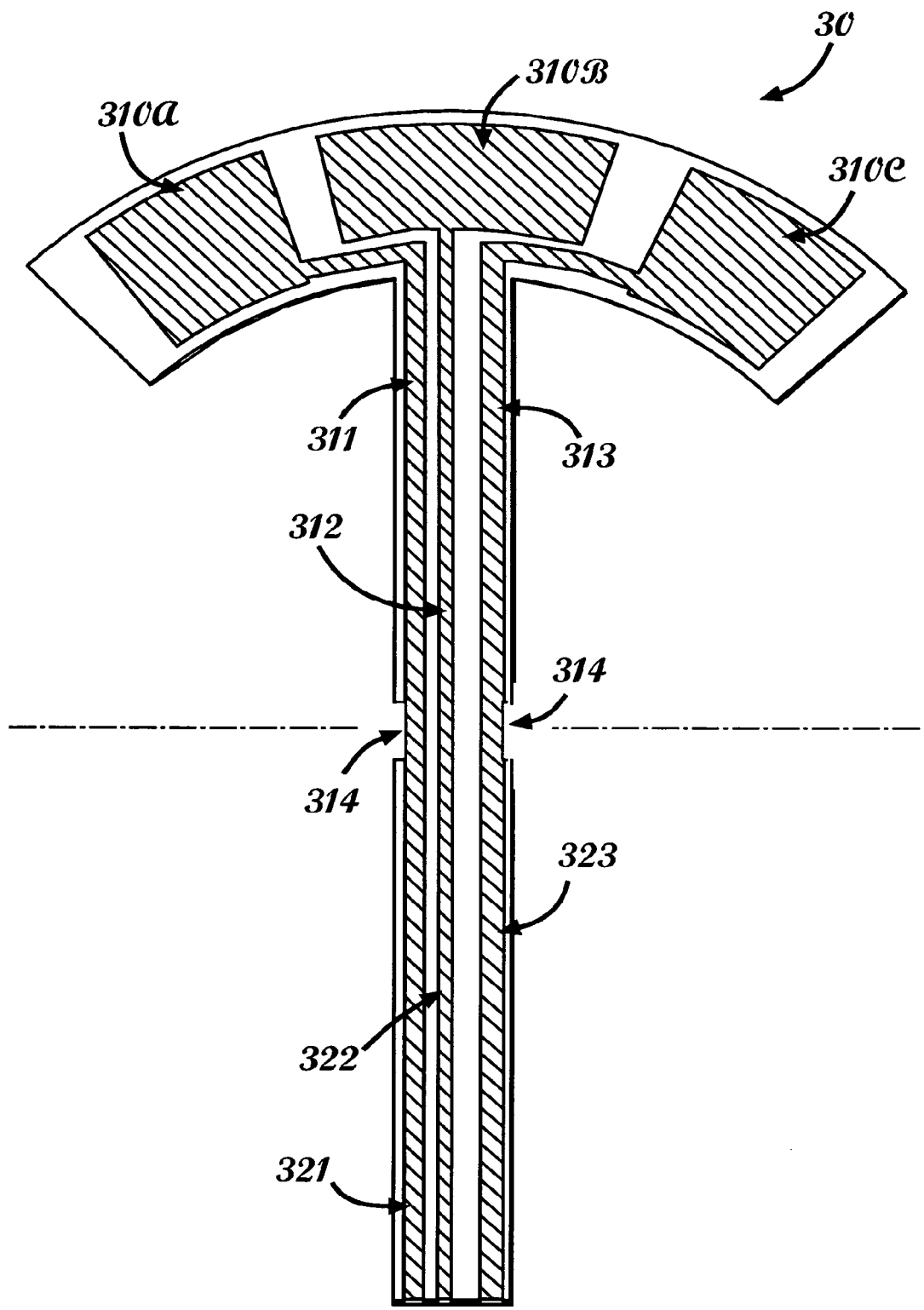
FIG. 21 shows a preferred embodiment of a single sensing probe that comprises three (3) electrodes according to some embodiments of the disclosure.

FIG. 21 illustrates an example embodiment of a planar sensing probe 30 having three (3) electrodes: a working electrode 321, a counter electrode 322, and a reference electrode 323. In some embodiments, the probe may include more than one electrode of each kind, e.g., three (3) working electrodes, three (3) counter electrodes, and one (1) reference electrode. The electrodes may be connected via wires 311, 312, and 313 to electrical connectors 310a, 310b, and 310c. The electrical connectors 310a, 310b, and 310c may be located on a wider surface to enlarge the conducting contacting area. The wider surface may be arched (e.g., partially circular) to match a shape of a bottom side of a cannula housing. In some embodiments, the probe 30 may be folded (e.g., bent, twisted, curved) to fit the tip's configuration. One or more gaps (or nodes) 314 may be formed in the probe surface to enable probe's flexibility and allow folding of the probe (e.g., along the dotted line).

Figure 22:
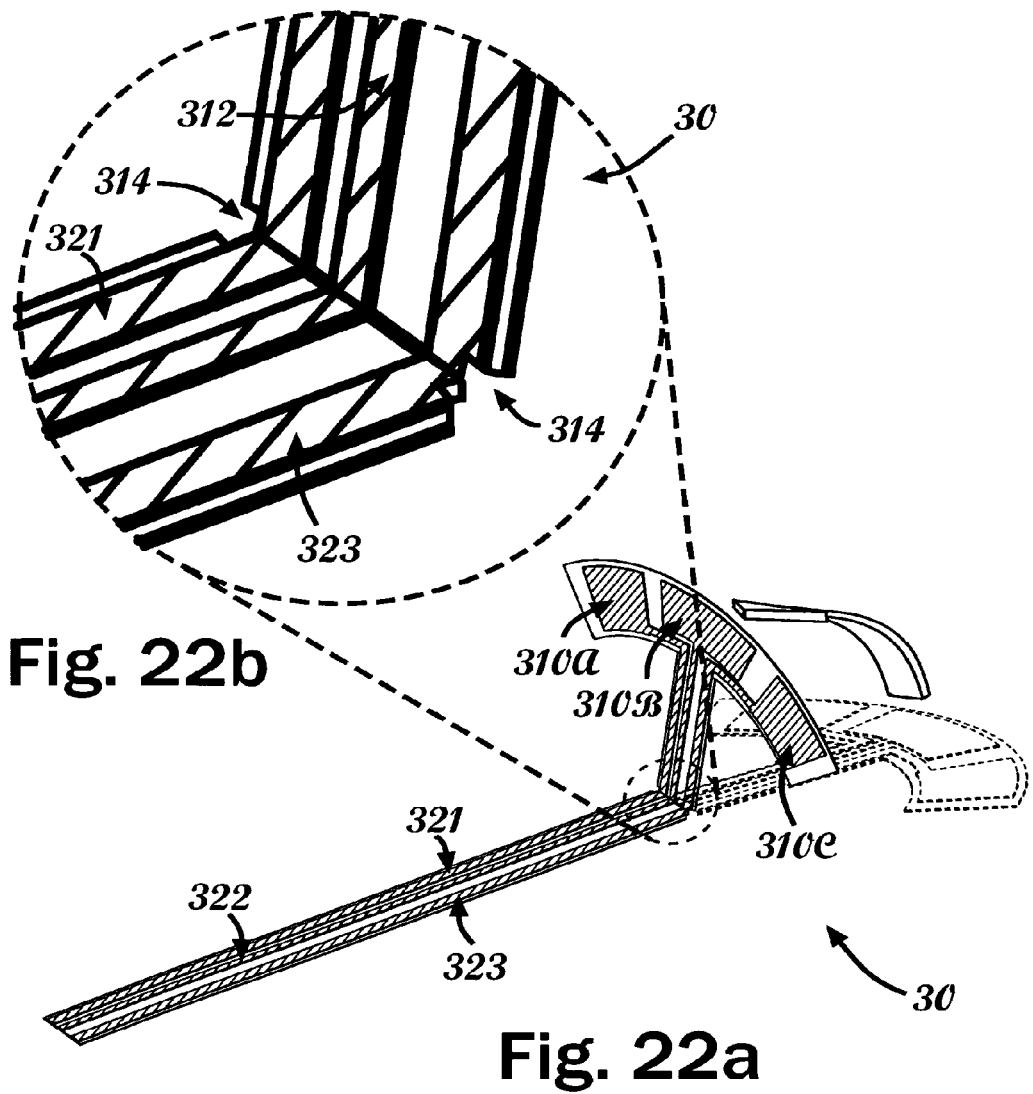
FIG. 22a-b shows a spatial configuration of a folded probe that comprises three (3) electrodes according to some embodiments of the disclosure.

FIGS. 22a-b illustrates a probe 30, according to some embodiments of the present disclosure, having three (3) electrodes 321, 322, 323, wires (e.g., 312), and respective connectors 310a, 310b, 310c. In some embodiments, the probe is configured to be folded at a folding line at one or more gaps 314. As shown in the magnified view (FIG. 22b), the wires 312 are folded accordingly.

Figure 23:
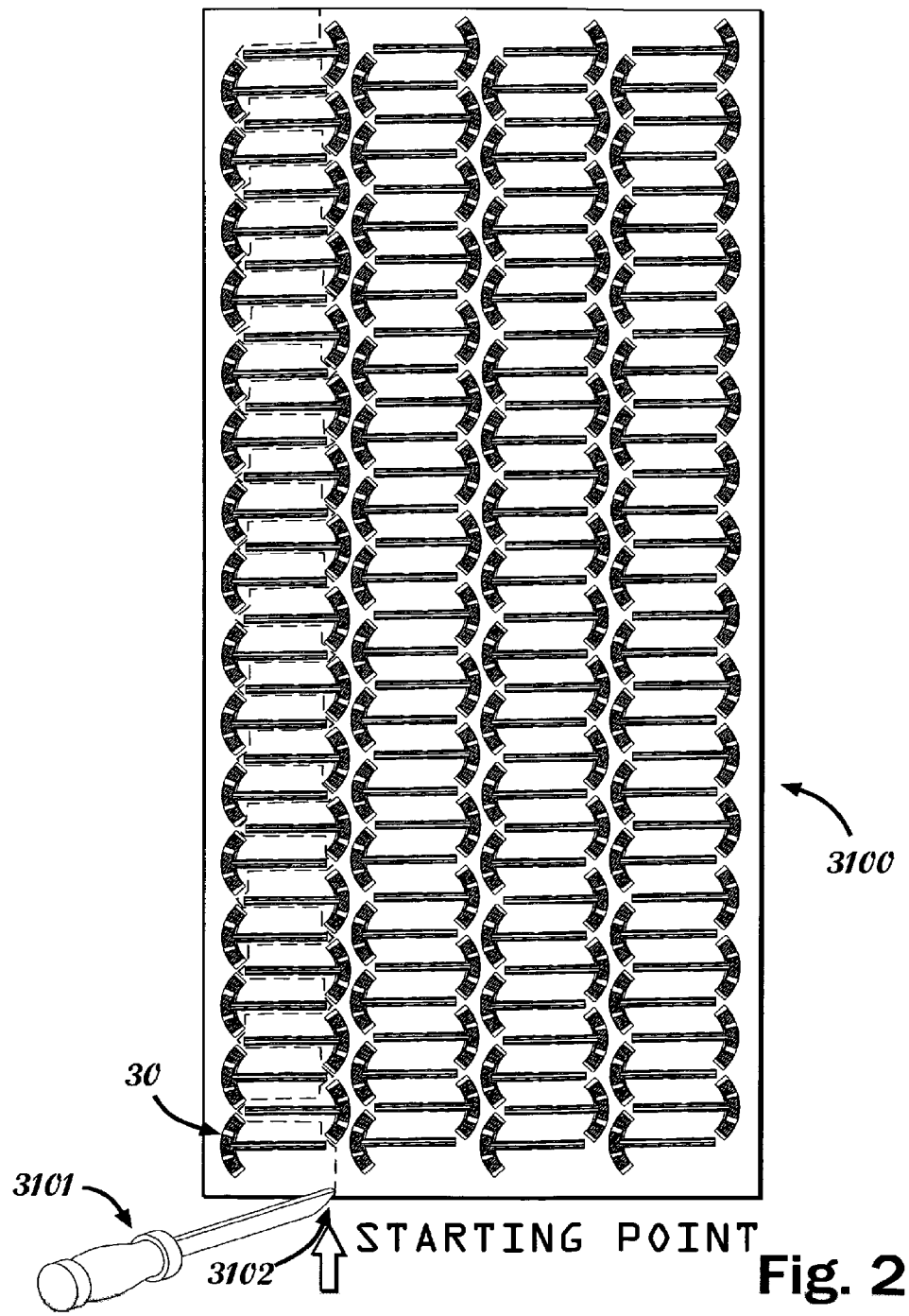
FIG. 23 shows an example of manufacturing process of multi-probes according to some embodiments of the disclosure.

FIG. 23 shows an example of manufacturing process of plurality of probes 30. A plate or film 3100 made of a non-conducting flexible polymer (for example polyimide/Kapton®) may be provided. Electrodes made of a conductive metal (e.g., gold, titanium covered/coated with gold) may be sputtered on the polymer at a desired shape(s) by using protective masks as known in the art (e.g., photolithography). Probes 30 may be configured around electrodes in the desire shape and subsequently may be cut 3102 to a final desired shape with any cutting means 3101 known in the art.

Figure 24:
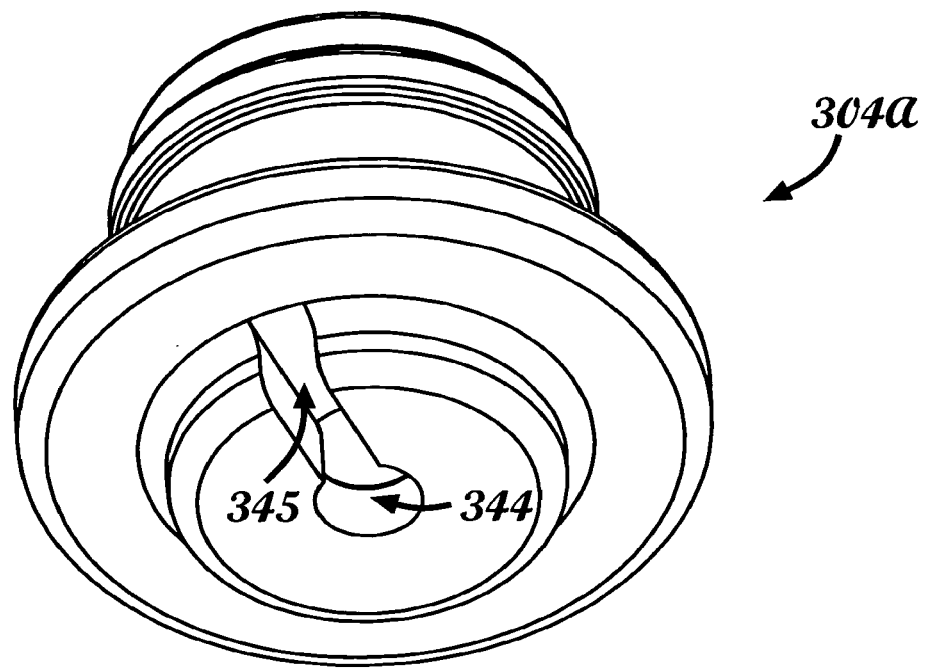
FIG. 24 shows a spatial view of a cannula housing according to some embodiments of the disclosure.
Figure 25A:
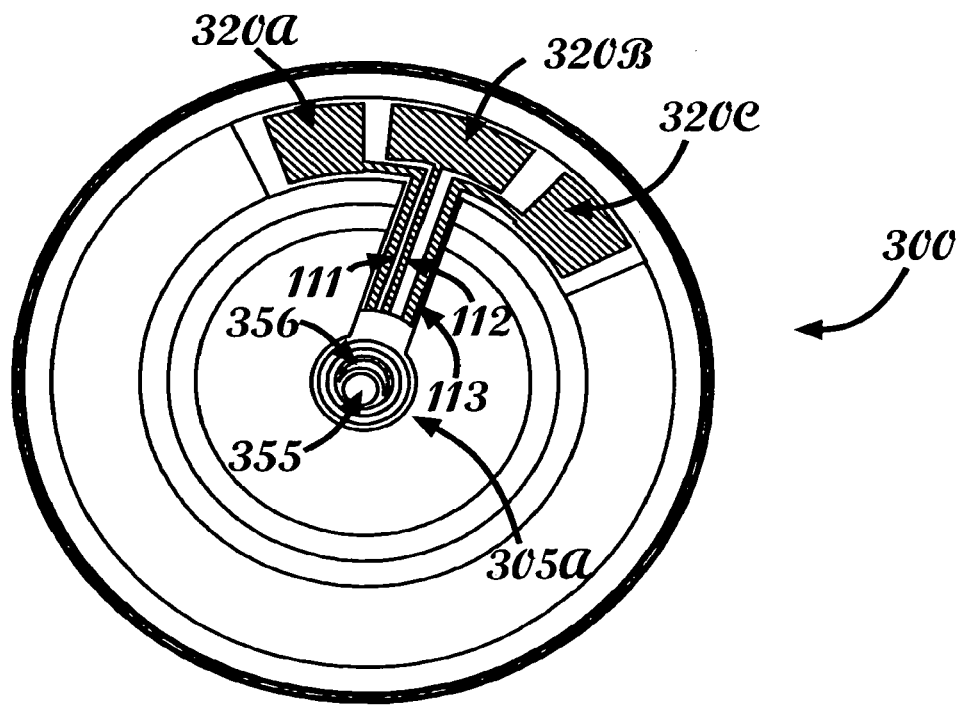
FIG. 25a shows a transverse cross sectional view of the bottom side of a tip according to some embodiments of the disclosure.
Figure 25B:
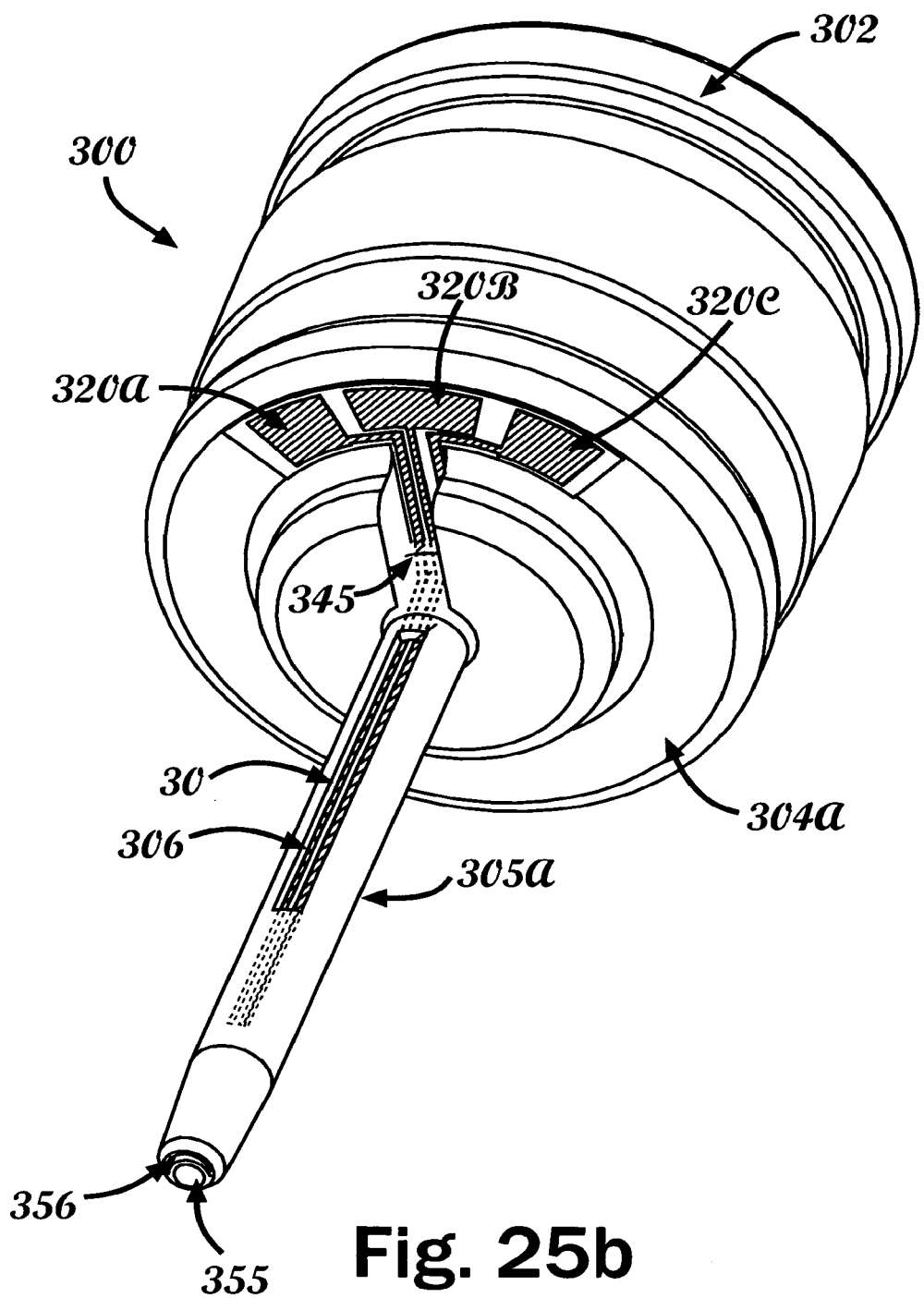
FIG. 25b shows a spatial view of a tip according to some embodiments of the disclosure.
Figure 26:
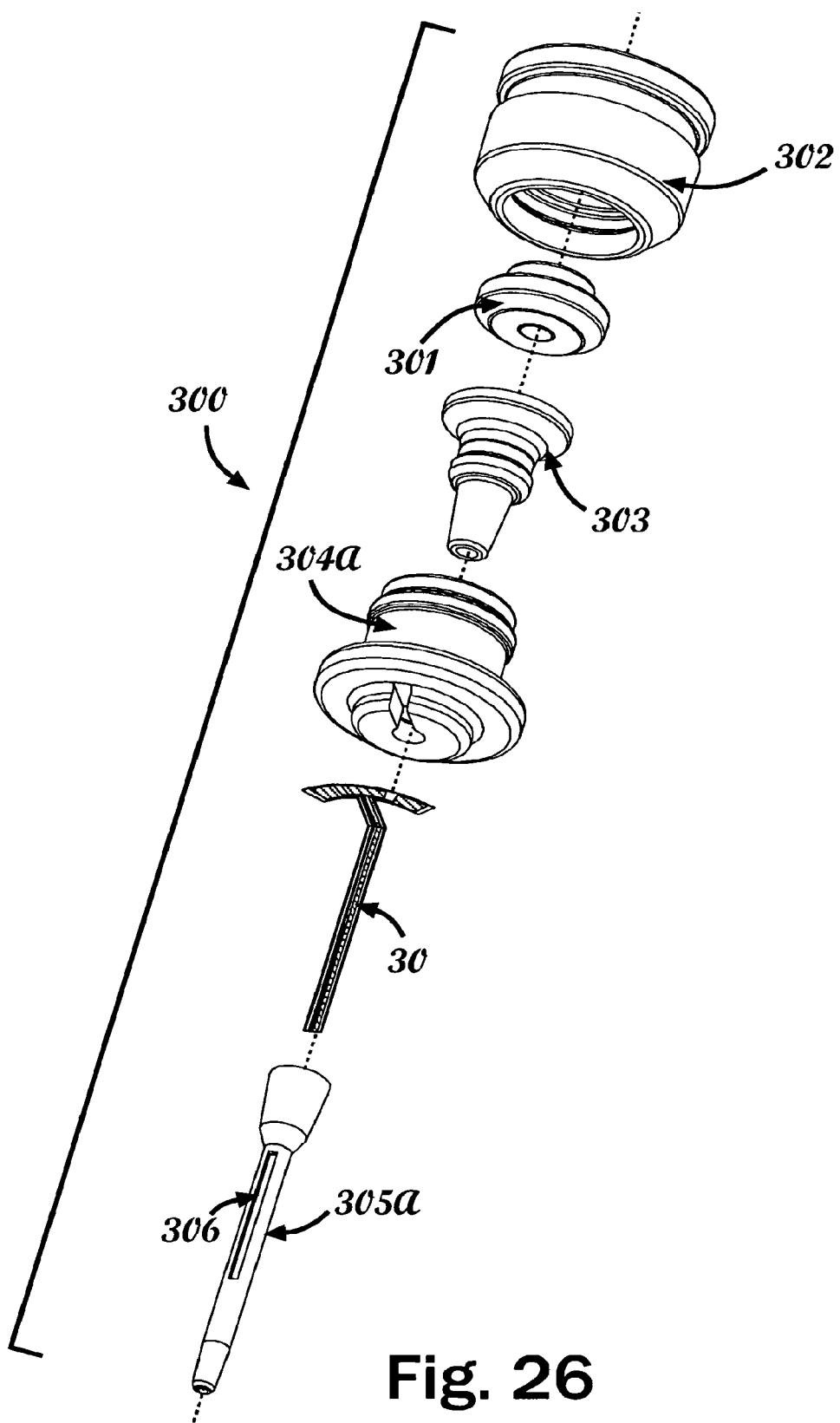
FIG. 26 shows a spatial view of the tip components before assembly according to some embodiments of the disclosure.

FIGS. 24-26 show spatial views of a tip (or portions of a tip), according to some embodiments of the present disclosure, having a probe as shown schematically in FIG. 12b. FIG. 24 shows a spatial view of a cannula housing 304a, according to some embodiments of the present disclosure. The cannula housing 304a may include a cannula passageway 344 and a cannula slot 345. The cannula passageway 344 is configured for receiving a multi-lumen cannula such as for example a double-lumen cannula having one lumen for delivering fluids and another for providing a probe. The cannula slot 345 is configured for occupying a folded portion of the probe.

FIG. 25a shows a transverse cross sectional view of the bottom side of a tip 300, according to some embodiments of the present disclosure. Cannula 305a may be located within cannula passageway (designated as 344 in FIG. 24, for example) of cannula housing. As noted in earlier disclosed embodiments, the cannula may include two or more lumens, where a first lumen 355 provides the passageway for insulin delivery and the second lumen 356 providing the probe. The probe may include a proximal portion and a distal portion and the distal portion of the probe may reside within or on lumen 356 and contain sensing electrodes. The probe may be folded as shown in FIG. 22a, and its proximal portion may reside on or within a cannula slot on a bottom side of a cannula housing. Electrical wires 311, 312, and 313 (not shown in FIG. 25a) may connect the electrodes to connectors 320a, 320b, and 320c located at the proximal side of the probe.

FIG. 25b shows a spatial view of a tip 300, according to some embodiments of the present disclosure. The tip 300 may include a cannula cover 302, a cannula housing 304a having a cannula slot 345 and a cannula 305a that includes two lumens (355 and 356) for delivering fluids and providing the probe. The connectors 320a, 320b, and 320c that are located at the bottom side of cannula housing 304a are configured to fit corresponding connectors located, for example, within the well of the cradle. Longitudinal opening (window) 306 may provide direct communication of interstitial fluid with probe electrodes.

FIG. 26 shows a spatial view of various parts of tip 300, according to some embodiments of the present disclosure. In some embodiments, the tip 300 may be configured similarly to the tip described in FIG. 8 for example, yet including a cannula housing 304a with a slot (designated as 345 in FIG. 24 for example), a probe 30 and a cannula 305a having two or more lumens for delivering fluids and providing a probe 30.

Figure 27A:
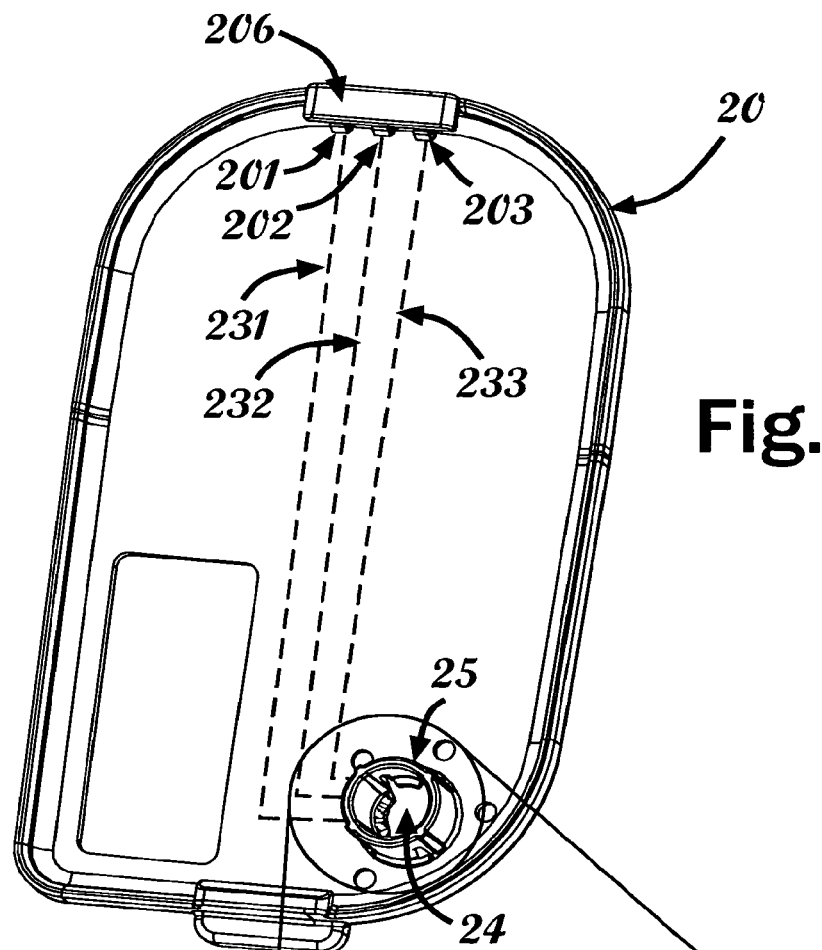
FIGS. 27a-b show electrical wires and electrical connectors of the cradle transmitting current from well connectors to snap connectors according to some embodiments of the disclosure.
Figure 27B:
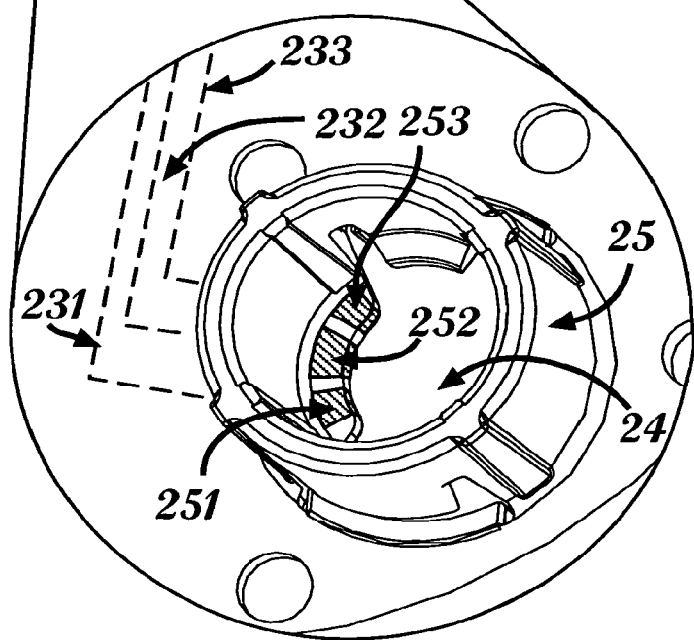

FIGS. 27a-b shows an example of cradle 20, according to some embodiments, which may include one or more electrical wires (or conducting elements) 231, 232, 233 for transferring electrical current from one or more connectors (e.g., 251, 252, and 253) located within well 25 to one or more connectors 201, 202, 203 provided, for example, on a connection means (e.g., snap) 206 (e.g., "snap connectors"). In some embodiments, the cradle may include conductive paths (e.g., miniature tunnels formed in the cradle) for housing the wires 231, 232, 233 transferring the electrical current. In some embodiments, the cradle may further include other electronic components such as an amplifier, for example, for strengthening the signal generated on the electrodes locate within the tip, preventing possible signal attenuation. In some embodiments, the cradle may further include a power source enabling continuous operation of the electrodes. The connectors 251, 252, and 253 ("well connectors") may be provided within or on the well opening 24 and are configured to establish electrical communication with one or more tip connectors located on a tip configured to be received within well opening 24. In the example shown in FIG. 27b, the connectors 251, 252, 253 are located on a lower surface of the well 25. In other embodiments, the connectors may be located on at least one protrusion within the well 25 and configured to receive any of the tip configurations described herein. The well 25 and/or the tip may be configured such that upon connection of the tip to the well 25, the connectors 251, 252, 253 remain sealed. The snap connectors 201, 202, 203 are configured to enable electrical communication with RP connectors located in a recess within a patch configured to be connected to the snap 206 of the cradle 20. In some embodiments, the one or more snap connectors 201, 202, 203 may be provided on a side wall of the cradle under snap 206 and contact RP connectors located under the recess.

Figure 28A:
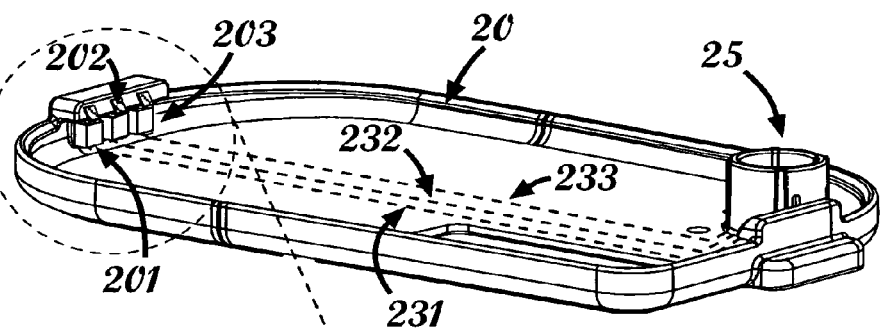
FIGS. 28a-b show a spatial view of electrical pathway in the cradle according to some embodiments of the disclosure.
Figure 28B:
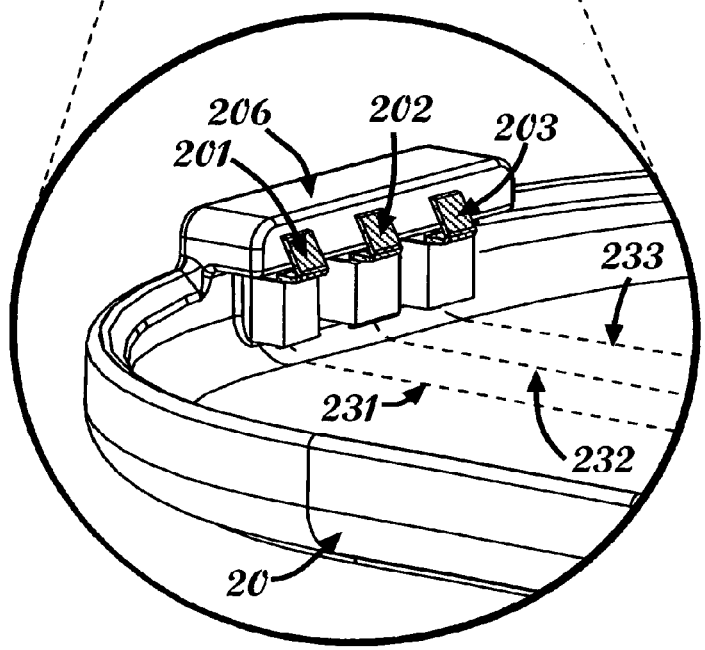

FIGS. 28a-b show spatial views of an example for electrical pathway in cradle 20. In some embodiments, the cradle may comprise a well 205, a snap 206, electrical wires 231, 232, and 233 and electrical contacts/snap connectors 201, 202, 203 as described in reference to FIGS. 27a-b. The snap connectors 201, 202, 203 shown in FIGS. 28a-b (for example) may be configured such that they remain sealed when the patch unit is disconnected from the cradle. For example a non-conductive sealed cap may be provided to cover the connectors 201, 202, 203. The sealed cap may be made of a sealing material (e.g., rubber, silicone, etc.) providing sealing to the connectors 201, 202, 203. In some embodiments, the RP connectors may be configured to prick the sealing cap for contacting the snap connectors. In other embodiments, the sealing cap may be removed when the patch is connected to the cradle. In yet other embodiments, the sealing cap may include contacting pads embedded within the sealing material, such that upon contact with connectors located on the reusable part, electrical current is conducted.

Figures 28C, 28D:
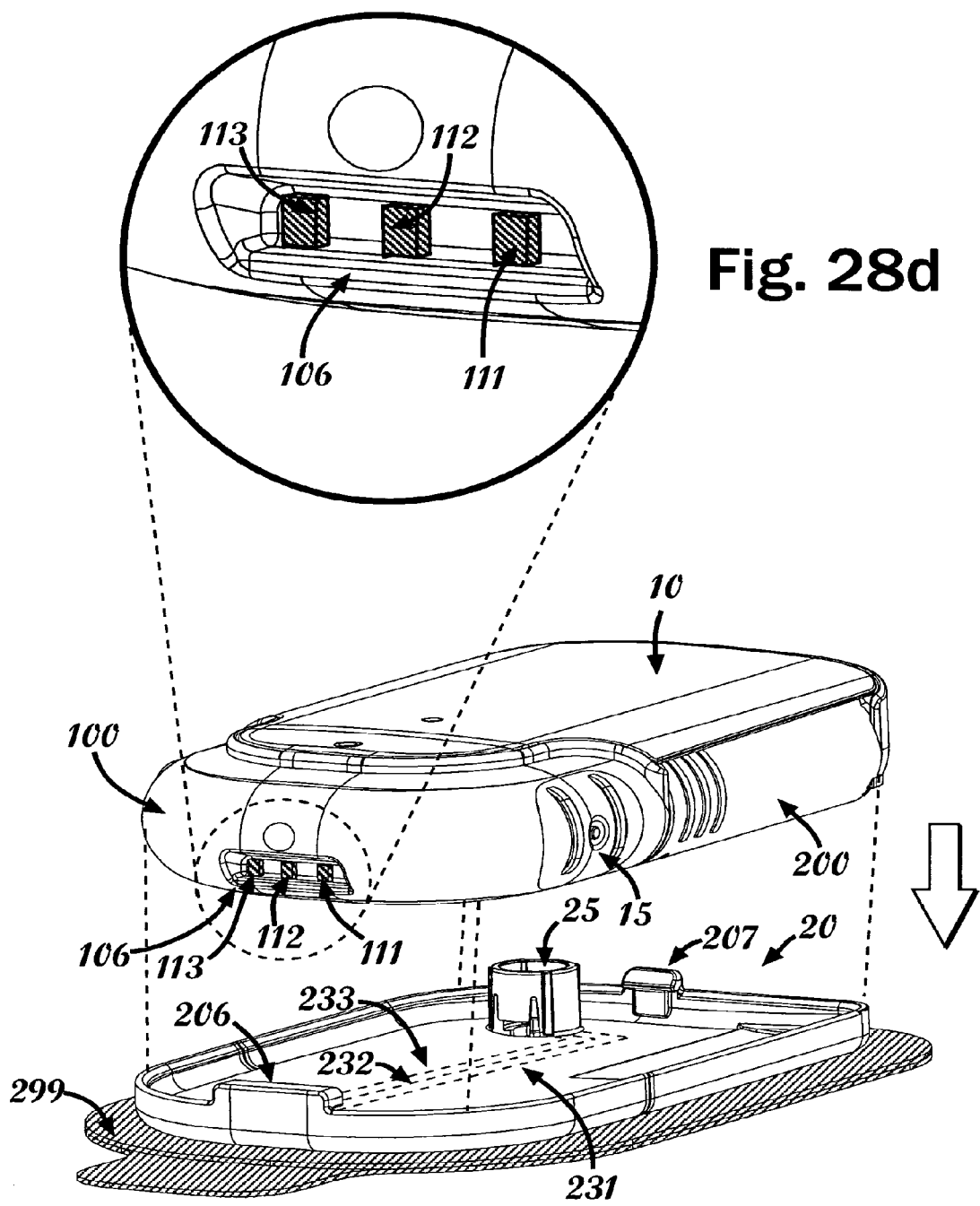
FIGS. 28c-d show a spatial view of the patch and the cradle before connection and the electrical path between the cradle well and the reusable part of patch according to some embodiments of the disclosure.

FIGS. 28c-d show spatial views of patch 10 and cradle 20 before connection and an example of electrical path between the cradle and the patch 10. After connection of the patch 10 to the cradle 20, the cradle snap 206 is engaged with the recess 106 and the snap connectors contact RP connectors 111, 112, and 113, such that currents are being conveyed from the one or more electrodes to the processor.

Figure 29A:
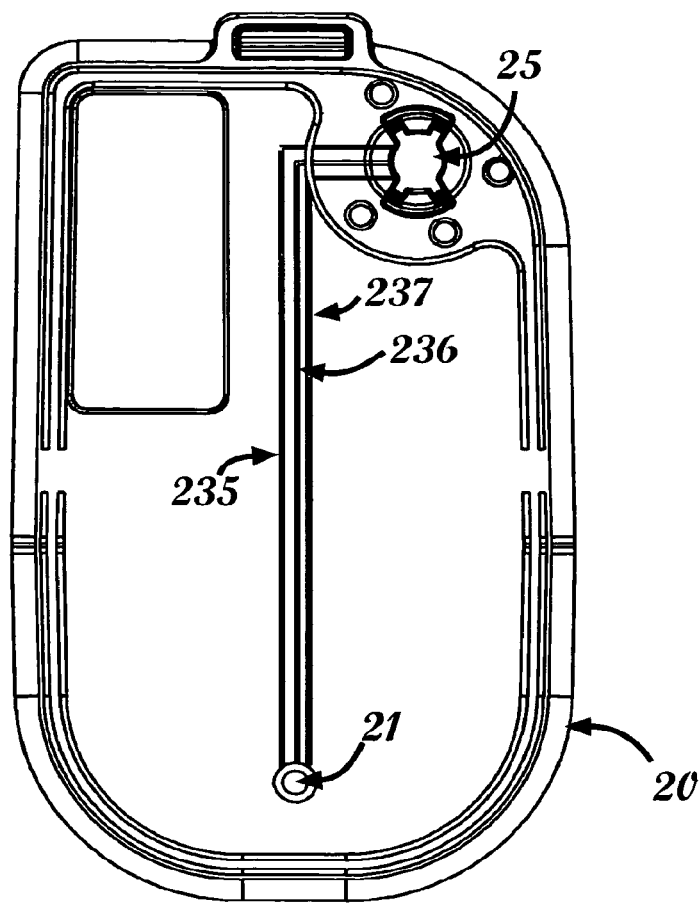
FIGS. 29a-d show a cradle electrical path according to some embodiments of the disclosure.
Figure 29B:
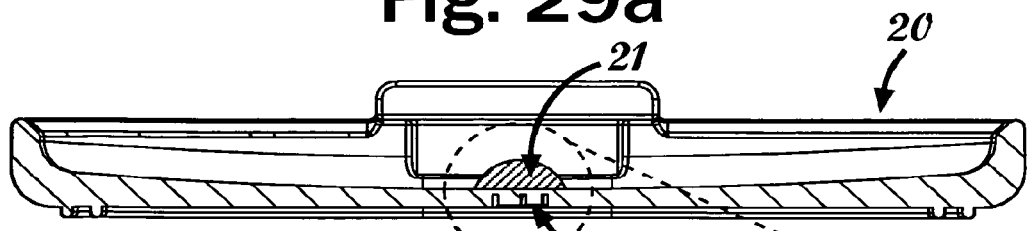
Figure 29C:
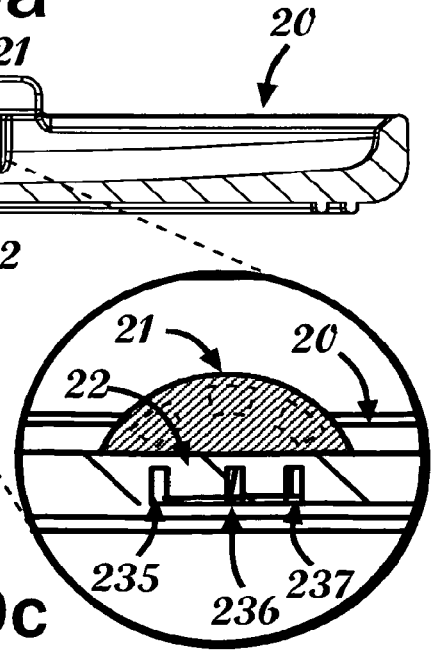

FIGS. 29a-d illustrate another example of electrical path between cradle 20 and patch 10. In some embodiments the connector(s) to the patch unit may be configured as a conductive protrusion 21. FIGS. 29b-c show a transverse cross sectional view of cradle 20 illustrating the contact between the wires within the miniature tunnels 22 and the conductive protrusion 21. The conductive protrusion 21 may be composed of any conductive material (e.g., conductive polymer, composite material, graphite, etc.), which may be elastic, and provide electrical communication between the wires 235, 236, 237 and the patch 10. A sealed cap may be provided to cover the conductive protrusion 21 when the patch unit is disconnected from the cradle. In other embodiments, the conductive protrusion 21 may be configured to remain sealed when the patch unit is disconnected from the cradle. For example contacting pads may be embedded within a sealing material (e.g., rubber, silicone, etc.), such that the wires 235, 236, 237 may contact the contacting pads and upon contact with connectors located on the reusable part, electrical current is conveyed to the RP.

Figure 29D:
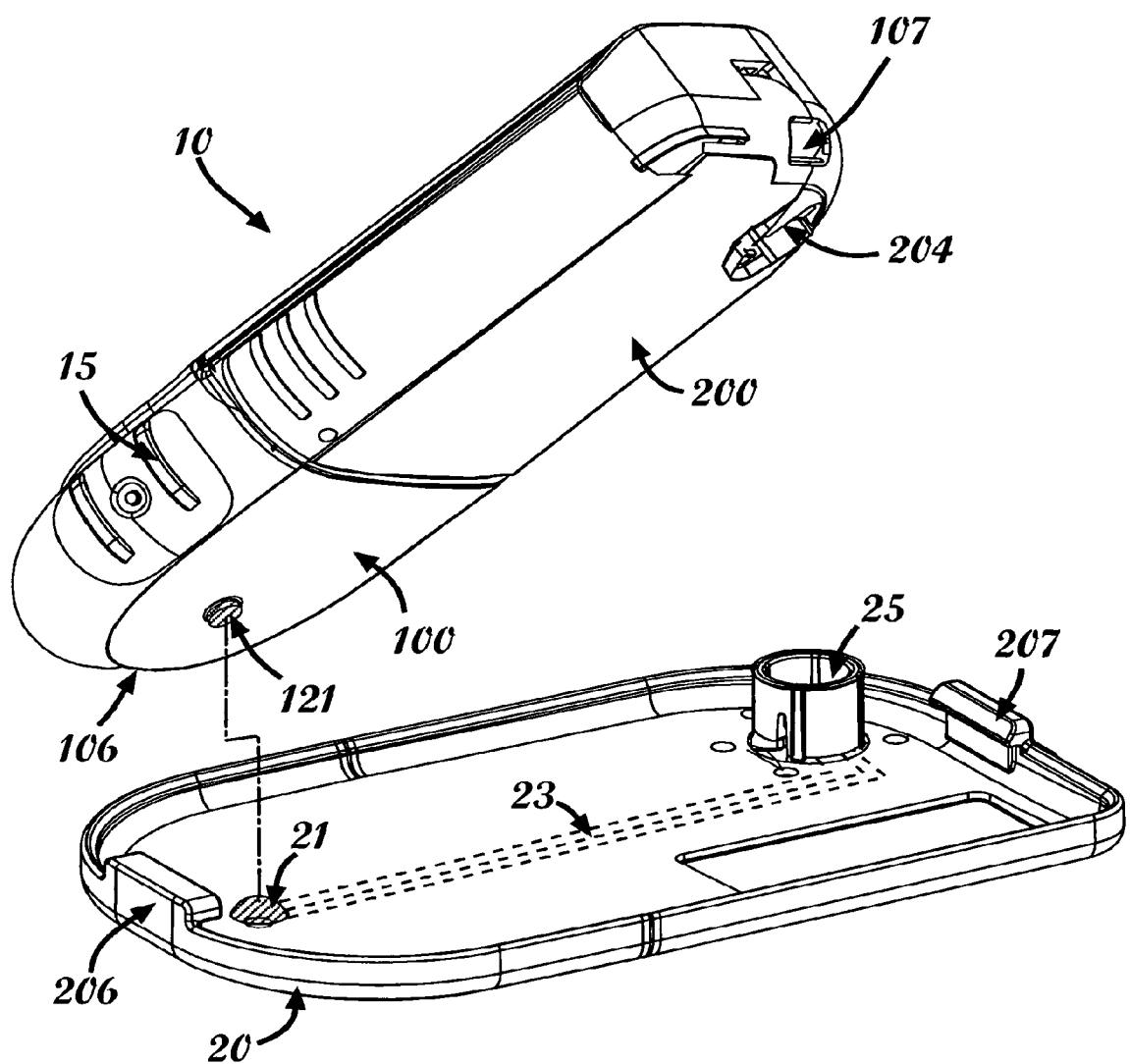

FIG. 29d illustrates a connection of patch 10 to cradle 20. Accordingly, upon a connection of the patch 10 to the cradle 20 electrical communication is established between the conductive protrusion 21 and a connector 121 in the patch 10. In some embodiments the electrical connector 121 provided at the bottom of the RP 100. The connector 121 may be composed of any conductive material (i.e. conductive polymer, composite material, graphite, etc.), which may be elastic, and may be configured to contact the conductive protrusion 21. The connector 121 may be configured to remain sealed when the patch is disconnected from the cradle. For example, a sealed cap may be provided to cover the connector 121 when the patch is disconnected from the cradle. Upon connection of the patch 10 to the cradle 20 the electrical connector 121 may be pressed against the conductive protrusion 21, such that wires 235, 236, 237 may contact contacting pads within the conductive protrusion 21 for conveying currents generated on the one or more electrodes to the processor.

FIGS. 30a-33b illustrate a configuration of a tip having a probe as described in FIG. 12a and FIGS. 13a-b, for example. According to some embodiments, the tip may include a cannula housing such that a proximal end of the probe is folded over outer curves of the cannula housing.

Figure 30A:
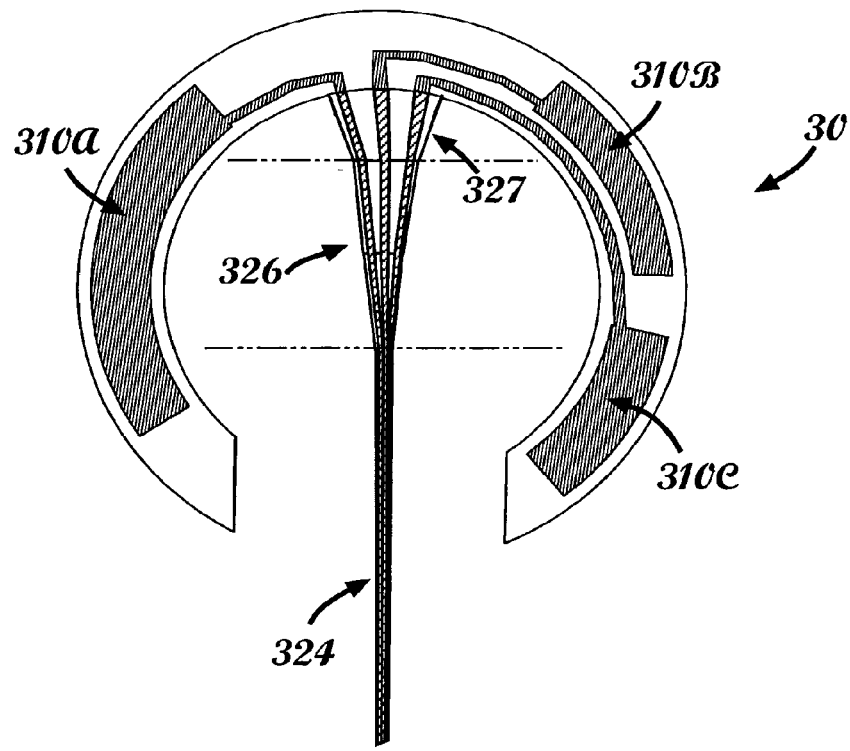
FIGS. 30a-d show a probe before and after folding and before insertion of the probe into the cannula lumen according to some embodiments of the disclosure.
Figure 30B:
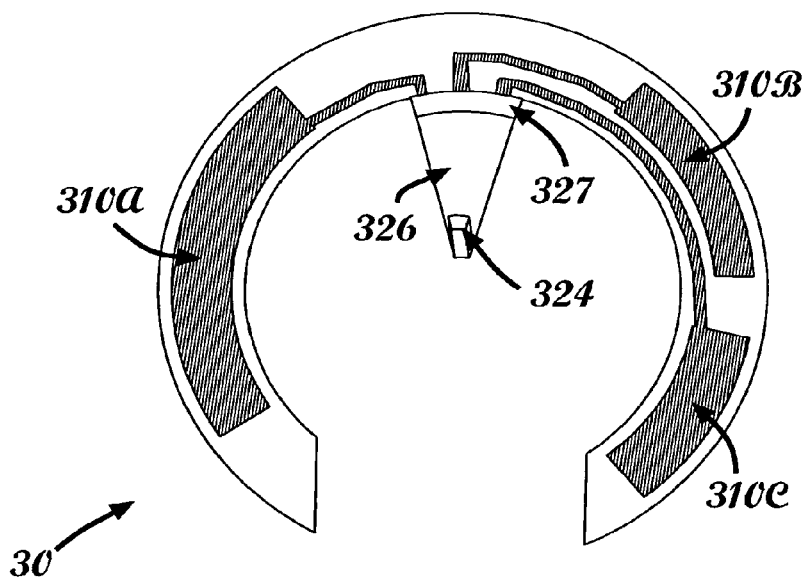
Figure 30C:
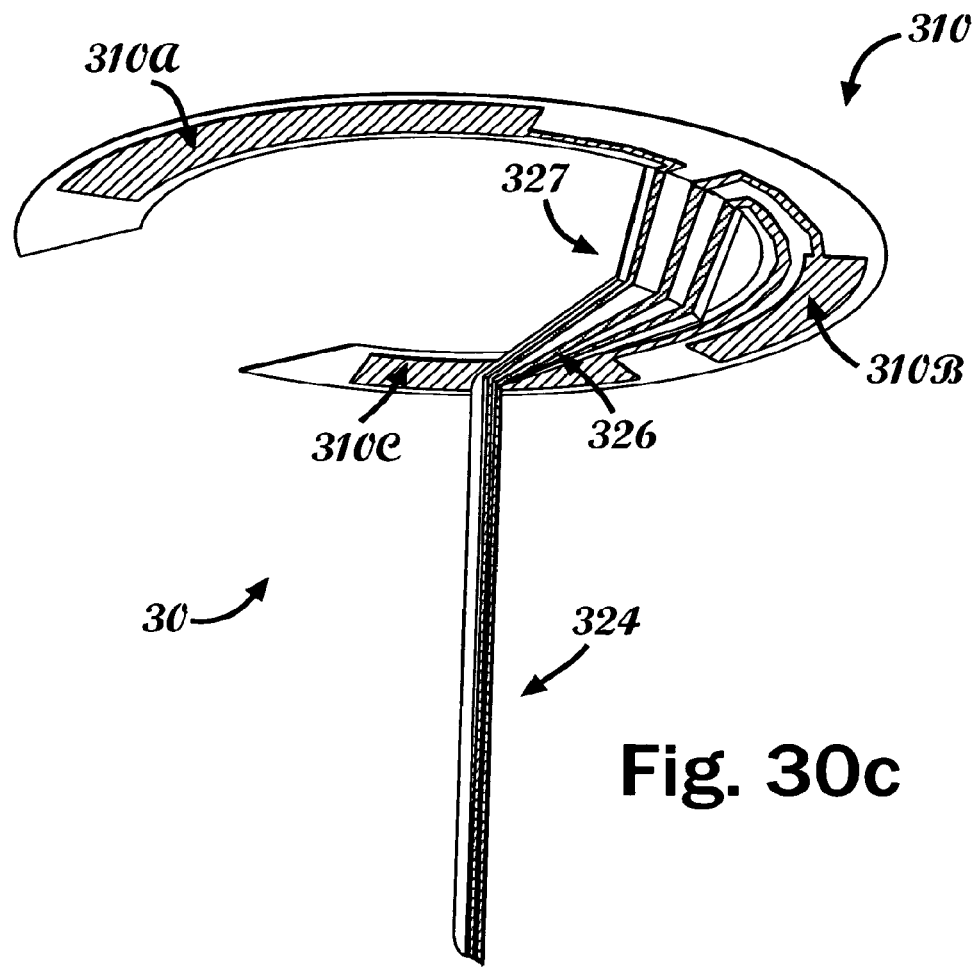
Figure 30D:
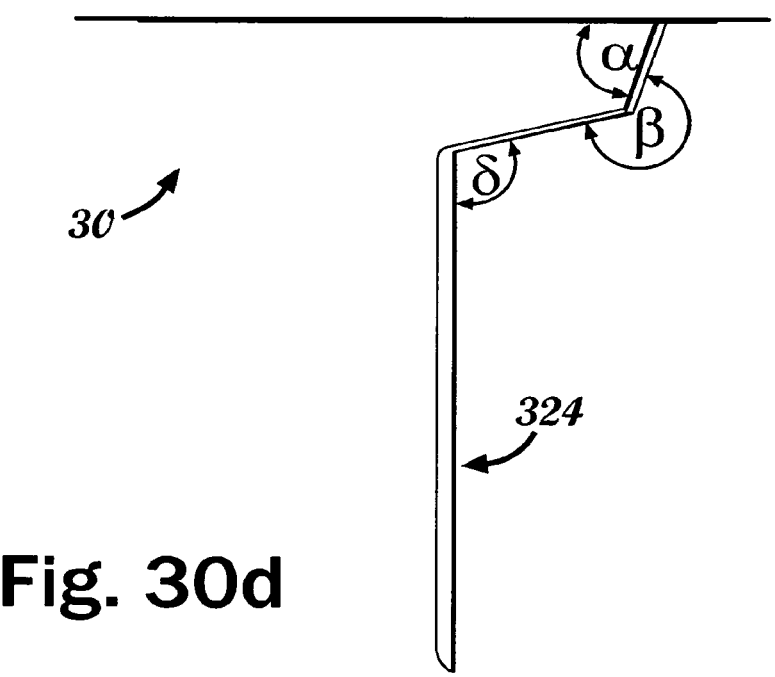
Figure 32A:
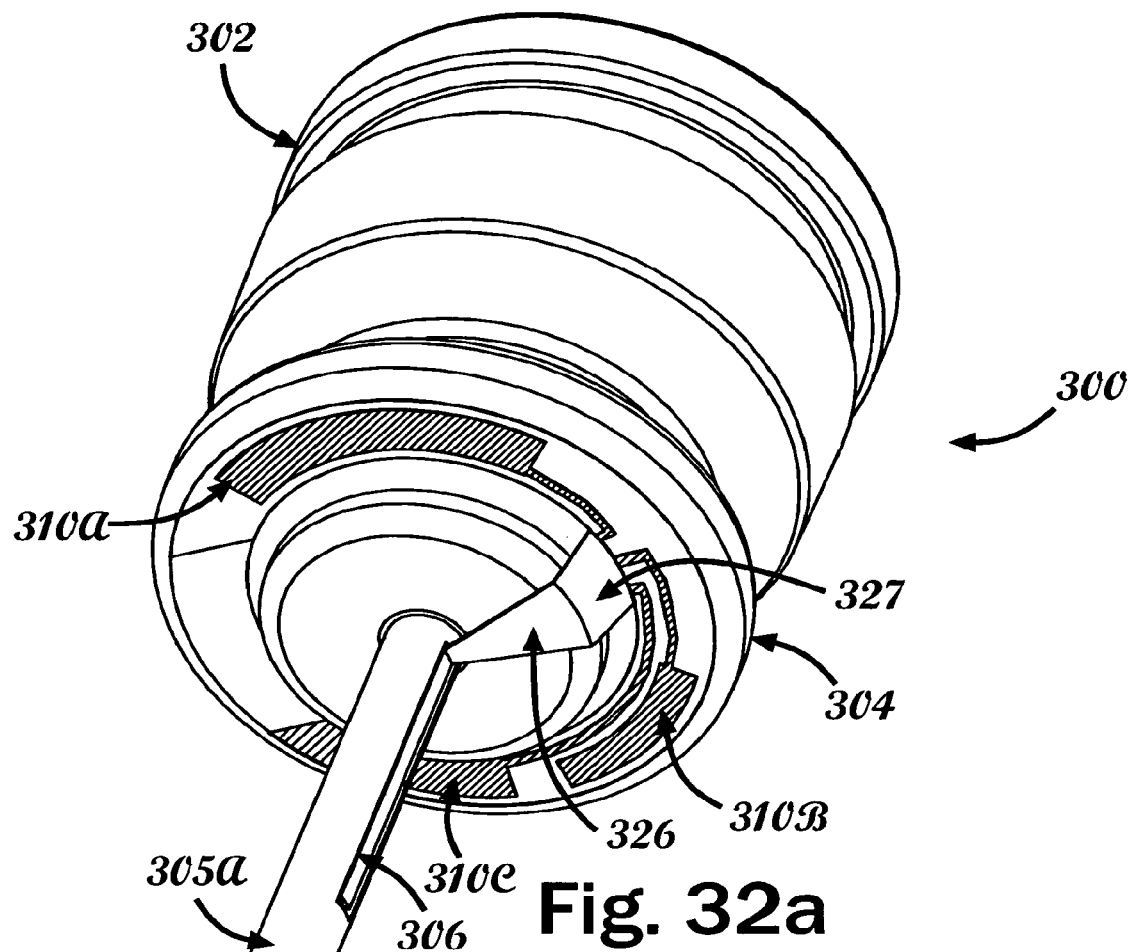
FIGS. 32a-c show a spatial and bottom views of the tip according to some embodiments of the disclosure.

Accordingly, FIG. 30a illustrates the probe 30 before insertion into cannula lumen and folding. The probe 30 may include a distal end 324 configured for residing within the cannula lumen and a proximal end configured to be located below the bottom side of the cannula housing. The distal end 324 may include sensing electrodes and connecting wires transferring current generated on the electrodes to connectors 310a, 310b, 310c, located at a proximal end of the probe. In some embodiment, the proximal end may be wider to match the bottom side of a cannula housing form/shape, and is preferably arched (e.g., circular, half circular or partially circular). At the proximal end of the probe the wires may be folded into one or more surfaces to fit the bottom side of the cannula housing, as illustrated in FIG. 32a. For example, the wires may be folded at pivots (see dotted lines) as illustrated in FIG. 30a, into two folded surfaces 326, and 327 (for example). FIG. 30b shows a bottom view of the probe 30, illustrated in FIG. 30a. FIG. 30c shows a spatial view of the probe 30 including the folded surfaces 326 and 327 of connecting electrical wires, and connectors 310a, 310b, 310c. FIG. 30d shows schematically the folded probe 30. Accordingly, the probe is folded at pivotal lines according to folding angles $\delta$, $\beta$, and $\alpha$.

Figure 31:
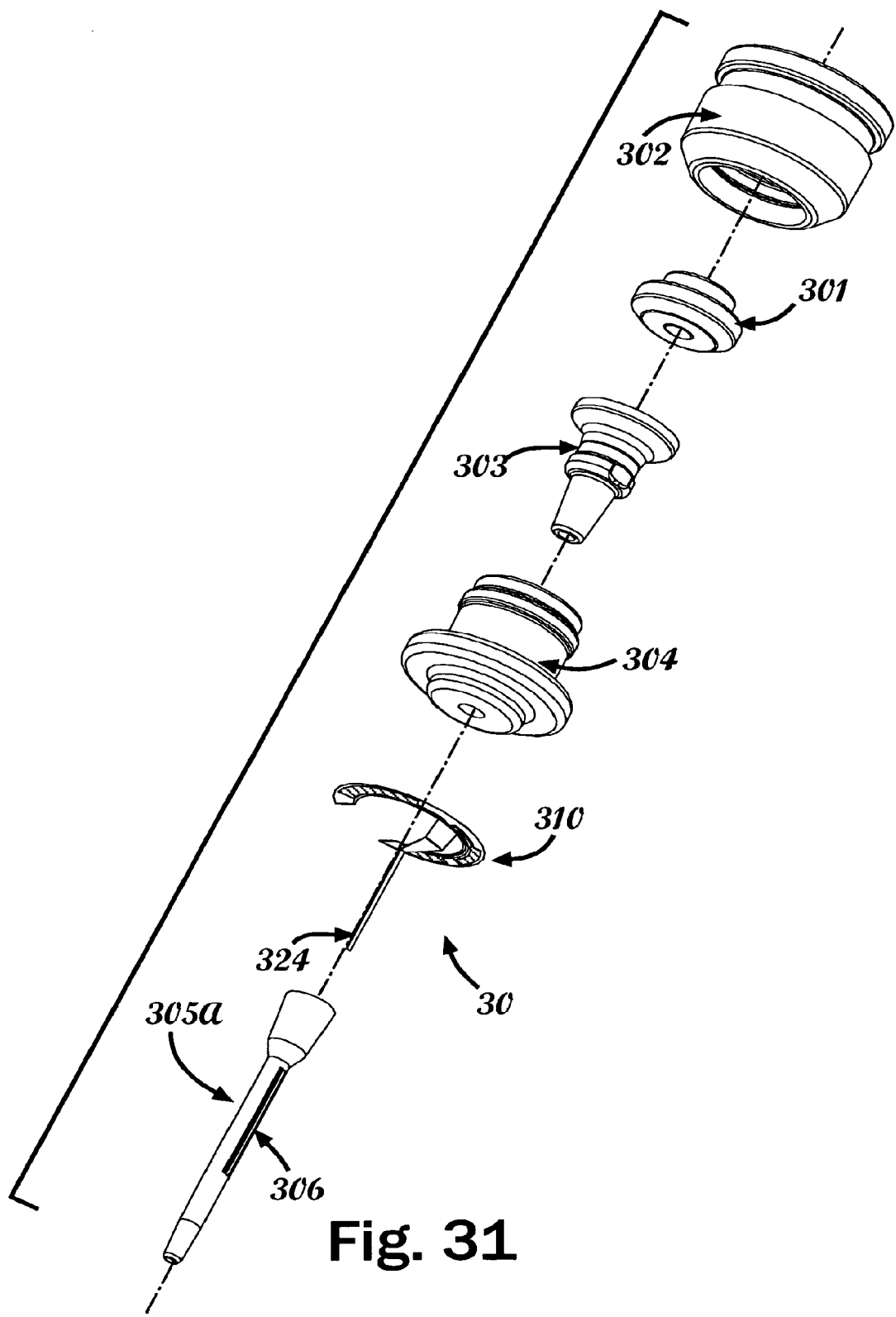
FIG. 31 shows a spatial view of tip components before assembly according to some embodiments of the disclosure.

FIG. 31 shows a spatial view of various parts of the tip 300 (as illustrated in FIG. 26 for example, implementing the probe 30 illustrated in FIGS. 30a-d. In some embodiments the distal end 324 of the probe 30, as illustrated in FIGS. 30a-d, may be inserted to the second lumen through opening 306.

Figure 32B:
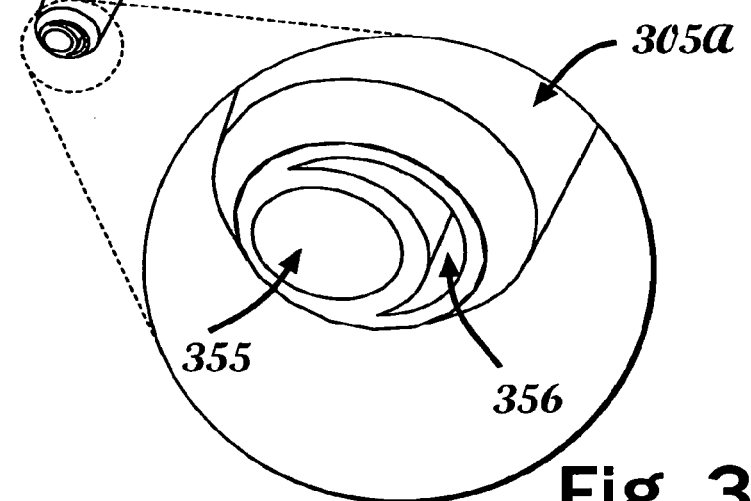

FIGS. 32a-b show spatial views of the tip 300 described in FIG. 30a-31 for example, according to some embodiments. The probe's proximal end may include at least a portion of the connecting wires folded over cannula housing 304 according to surfaces 326 and 327, and electrical connectors 310a, 310b, and 310c located at the bottom of the cannula housing 304. In some embodiments, the electrical connectors 310a, 310b, and 310c may be spatially arranged around the bottom of the cannula housing 304 to fit corresponding connectors located, for example, within the well of the cradle.

FIG. 32b shows a magnified view of the bottom side of the double lumen cannula 305a, illustrated in FIG. 32a.

Figure 32C:
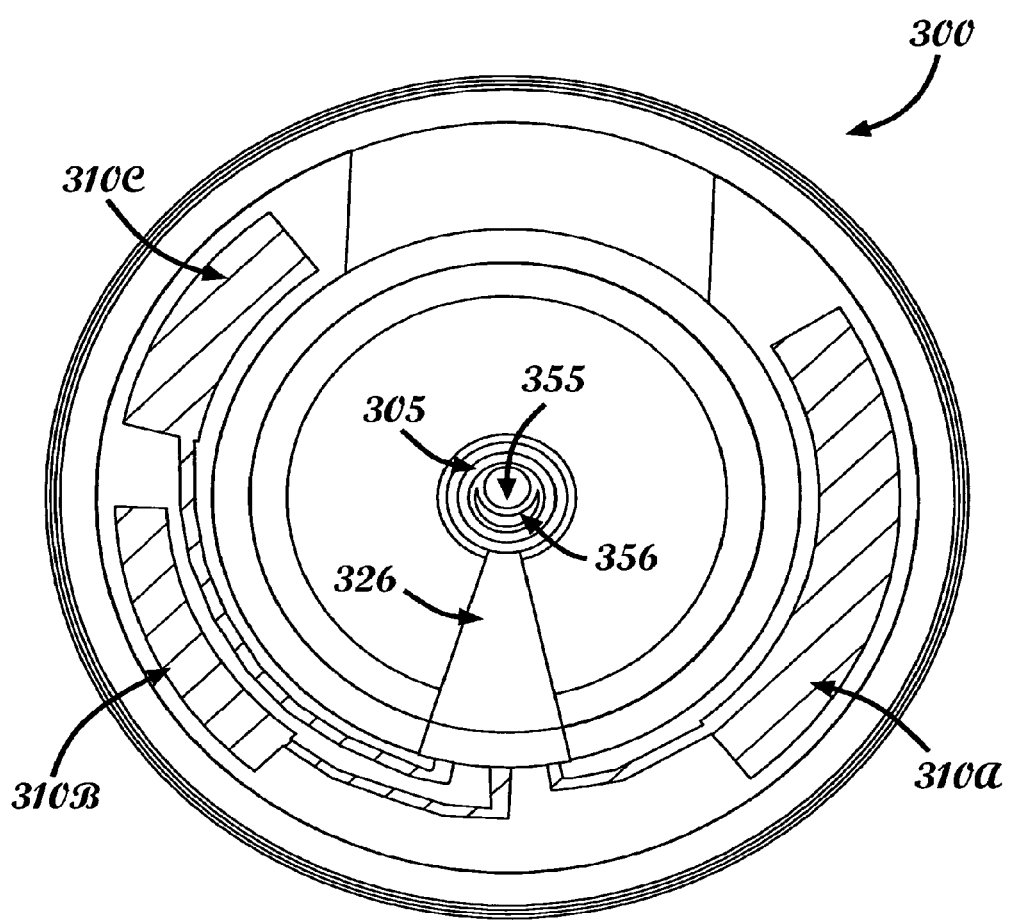

FIG. 32c shows a bottom view of the tip 300 described above, including the multi-lumen cannula 305a having lumens 355 for delivering fluids and a second lumen 356 including a distal end of the probe. The electrical wires may be folded along surfaces 326, 327, enabling the proximal end to be placed at a bottom side of the cannula housing.

FIG. 33a shows the tip 300 before connection to the cradle 20, according to some embodiments. Upon insertion of tip 300 into the body of the patient, recess 309 is engaged with a well protrusion providing rigid connection of the tip 300 to the cradle 20 and stable contact between the tip connectors 310 and the cradle connectors 251, 252, 253, such that electrical communication between the probe and the cradle wires 231, 232, 233 may be maintained. In some embodiments, the tip connectors 310 may be spatially arranged around the bottom of the cannula housing 304 to be aligned with corresponding connectors located on protrusions at the bottom side of the well 25. In the example shown, upon insertion of the tip 300, connector 251 is located on a first protrusion within the well and connectors 252, 253 are located on a second protrusion.

Figures 34A, 34B, 34C:
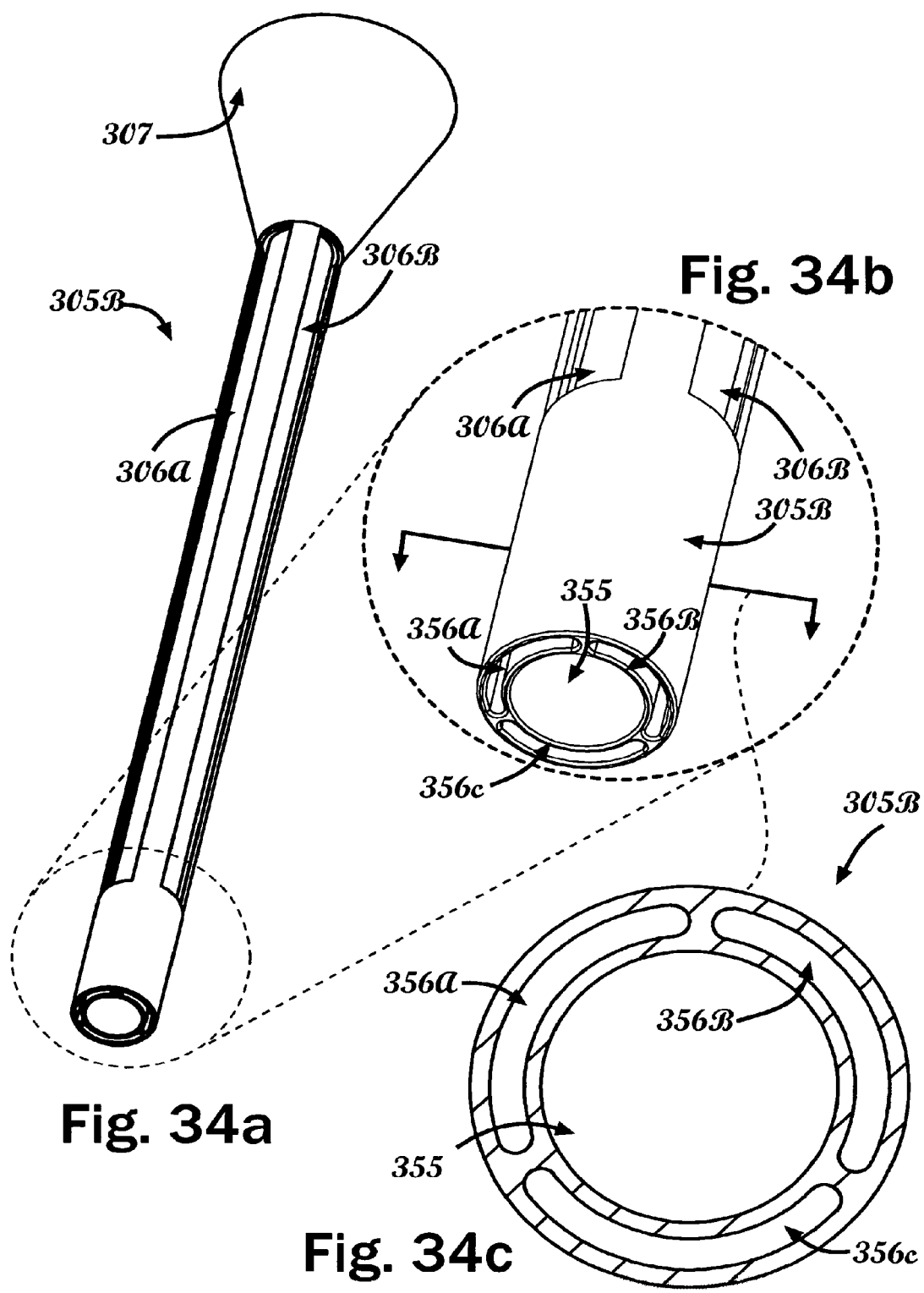
FIGS. 34a-c shows a multi-lumen cannula according to some embodiments of the disclosure.

FIGS. 34a-c illustrate a tip configuration, according to some embodiments of the present disclosure, having a multi-lumen cannula and sensing electrodes as previously shown for example in FIGS. 9b, 12c and 12d. According to this configuration, the multi-lumen cannula 305b may include more than two lumens (e.g., 4 lumens), and, similarly with previously discussed embodiments, a first lumen 355 providing a passageway for fluids (e.g., insulin) delivery and two or more second lumens (e.g., 356a, 356b, 356c) for accommodating (and/or supporting) the sensing electrodes, i.e., each electrode is provided at one of the two (2) or more second lumens. In some embodiments, the sensing electrodes include three (3) electrodes (e.g., working electrode, counter electrode and reference electrode) and the two (2) or more second lumens include three (3) lumens respectively, as shown in FIGS. 34a-c. In some embodiments, the sensing electrodes include two (2) electrodes (e.g., working electrode and counter electrode) and the two (2) or more second lumens include two (2) lumens each providing one (1) electrode. In some embodiments, more than one electrode of each kind may be provided, whereas each electrode may be provided by a separate second lumen. In some embodiments, the multi-lumen cannula 305b may be configured such that the first lumen 355 is in the center of the cannula ("central lumen") and the two (2) or more lumens 356a, 356b, 356c encircle the first lumen ("circumferential lumens").

FIG. 34a shows a spatial view of an example of a multi-lumen cannula 305b, FIG. 34b is a magnified view of the distal end of the cannula 305b, and FIG. 34c is a transverse cross sectional view of the cannula 305b illustrating a central lumen 355 for fluid delivery and circumferential lumens 356a, 356b, and 356c providing the electrodes. In some embodiments, the second lumens 356a, 356b, 356c may be closed at the bottom side of the cannula (i.e., at the distal end) enabling contact with the ISF only through openings 306a, 306b, 306c. In some embodiments, the electrodes may be configured as "leads" or "ribbons" inserted through the two or more second lumens, and in some embodiments, the one or more electrodes may be embedded within the material of the walls of the cannula 305b.

FIGS. 35a-39b illustrate an example of a tip having a multi-lumen cannula according to the configuration shown schematically in FIG. 12c, for example. In this example, the multi-lumen cannula includes one central lumen for fluid delivery and, for example, three (3) circumferential lumens each providing an electrode. In some embodiments, a connectors-plate 330 may be provided at the bottom side of cannula housing for maintaining electrical communication between the electrodes provided by the circumferential lumens and cradle connectors.

FIGS. 35a-c show spatial (FIG. 35a), top (FIG. 35b) and bottom (FIG. 35c) views of the connectors-plate 330. The connectors-plate 330 may include, for example, three (3) folded electrode connectors 334, 335, and 336, configured to contact the electrodes provided by circumferential lumens. The connectors-plate 330 may further include, for example, three (3) cradle connectors 331, 332, and 333 configured to contact connectors of a cradle. The connectors-plate 330 may be consisted of a conductive material (e.g., a metal) for conducting currents from the electrode connectors 334, 335, 336 to the cradle connectors 331, 332, 333. In other embodiments, a different combination of electrodes and connectors may be implemented, i.e., three (3) electrodes and three (3) connectors are brought merely as an example.

Figure 36:
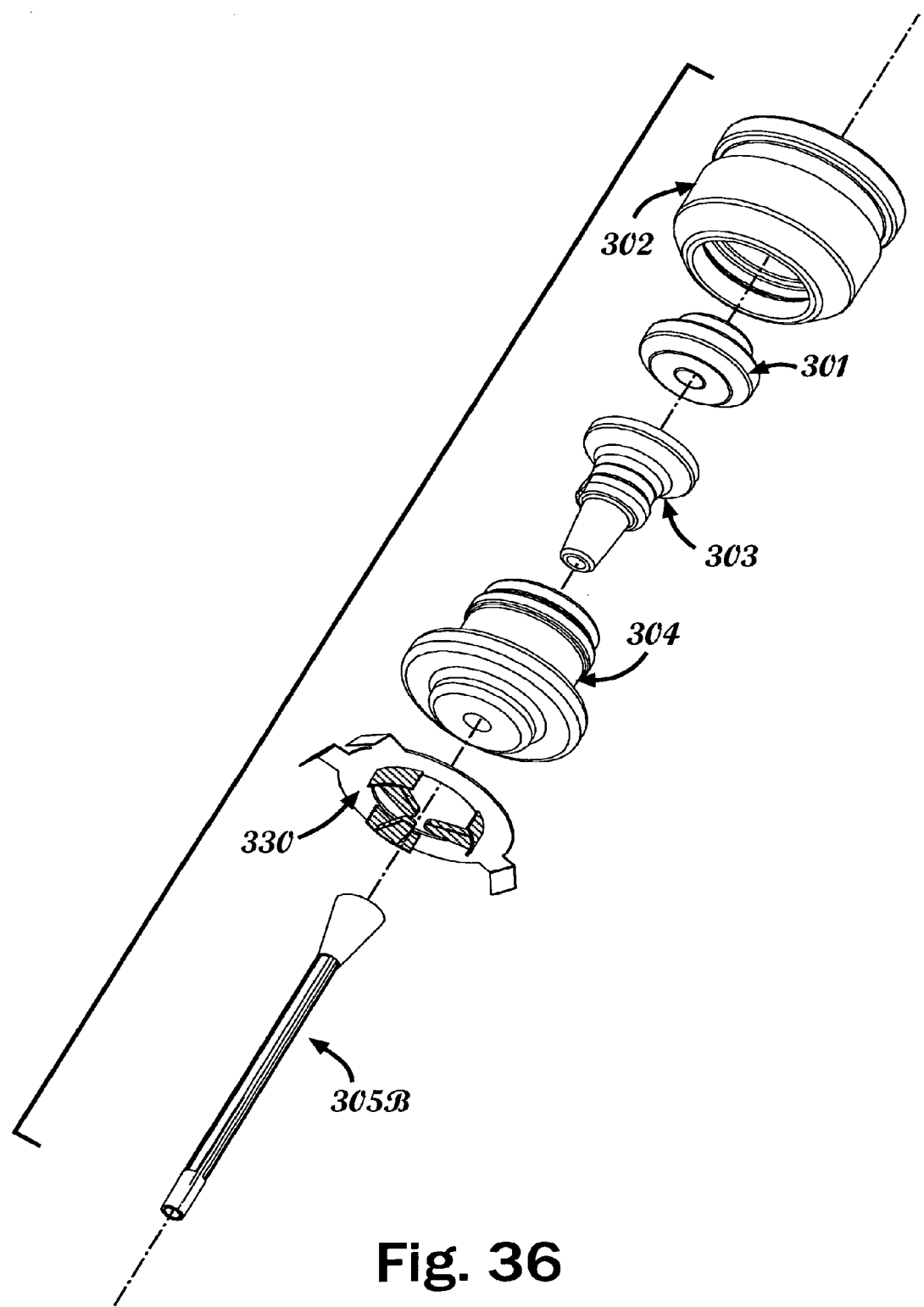
FIG. 36 shows a spatial view of tip components before assembly according to some embodiments of the disclosure.

FIG. 36 shows an exploded view of the various part of tip 300 before assembly, as previously described for example in FIG. 26, including cannula 305b with four (4) lumens. The connectors-plate 330 may be pressed and/or adhered to the bottom of the cannula housing 304 such that the inner opening of the plate and the folded electrode connectors may receive a protruded portion in the bottom of the cannula housing 304. The electrode connectors 334, 335, 336 may be further configured to contact the electrodes provided by the circumferential lumens 356a, 356b, and 356c through the openings (e.g., 306a, 306b, 306c), respectively.

Figure 37A:
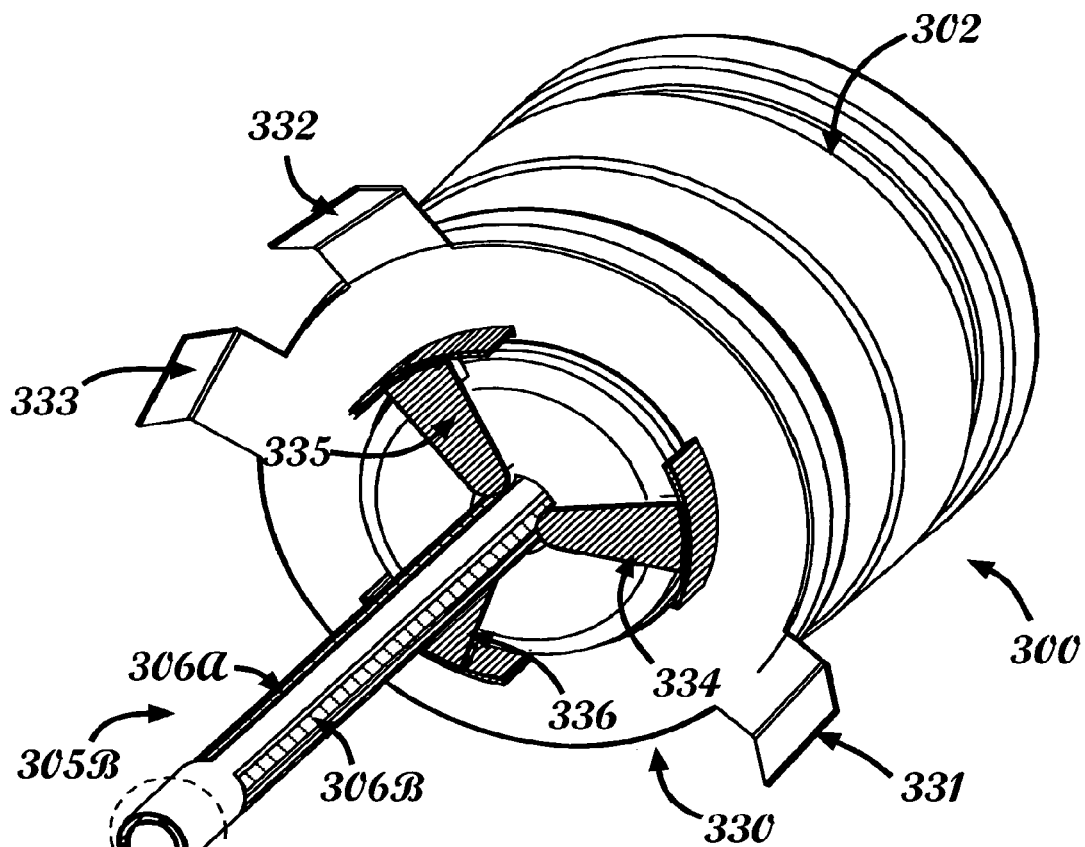
FIGS. 37a-b show attachment of the connectors-plate to the tip according to some embodiments of the disclosure.
Figure 37B:
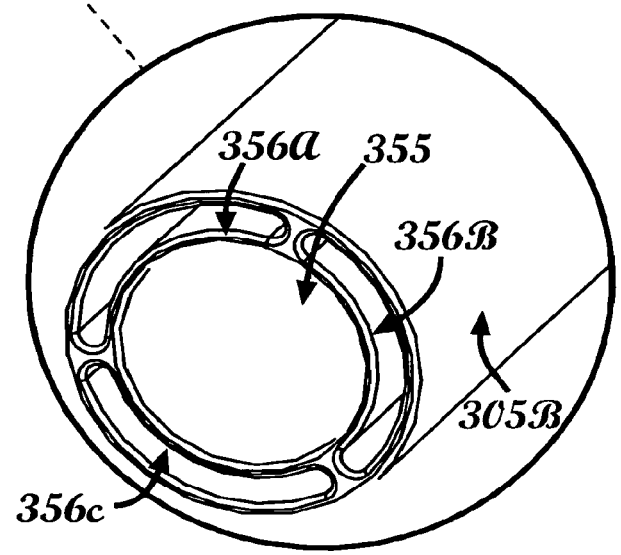

FIGS. 37a-b illustrate the assembled tip 300, which, in some embodiments, is similar to earlier described embodiments of the tip.

Figure 38:
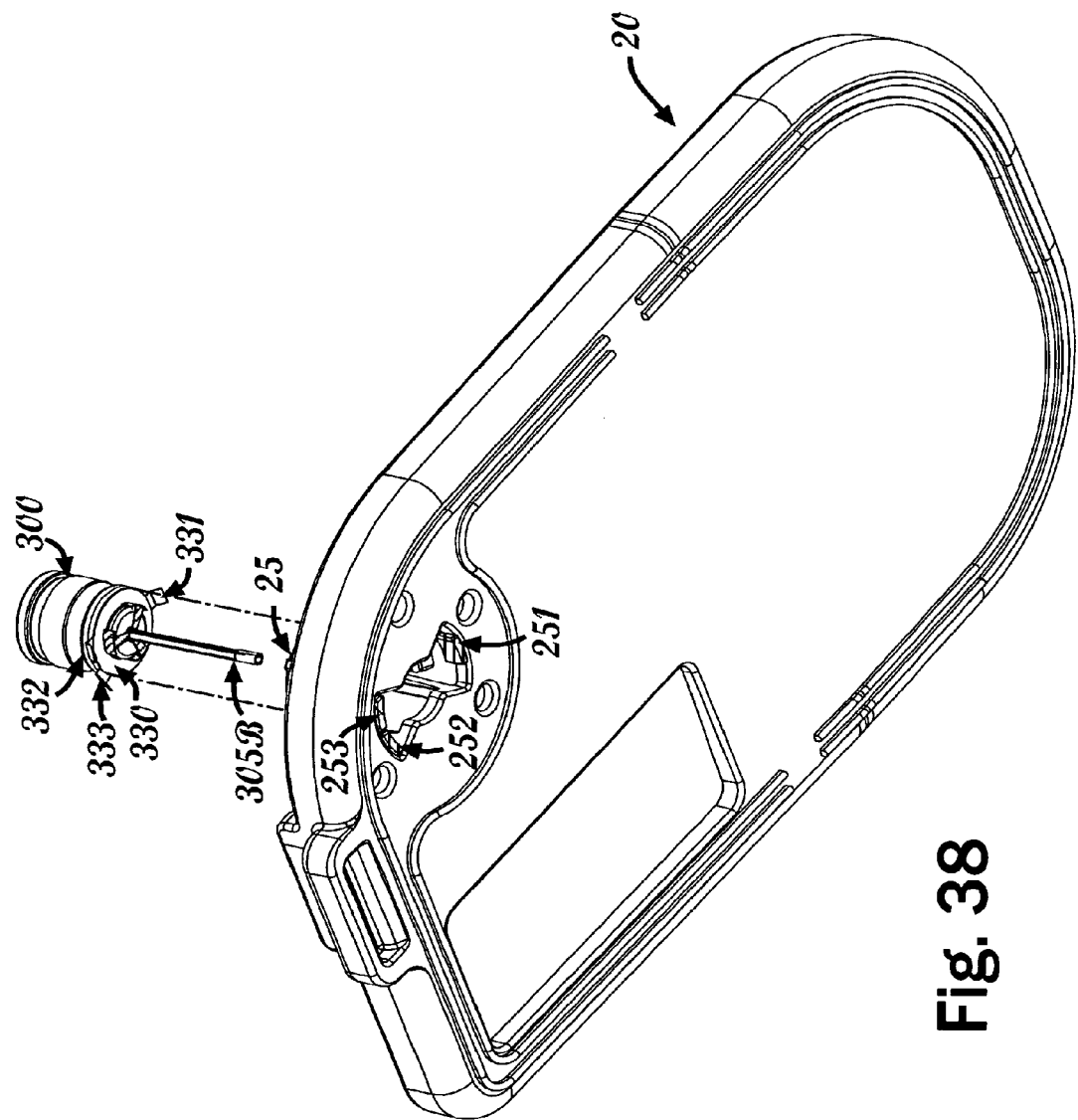
FIG. 38 shows the tip before insertion onto cradle according to some embodiments of the disclosure.
Figure 39A:
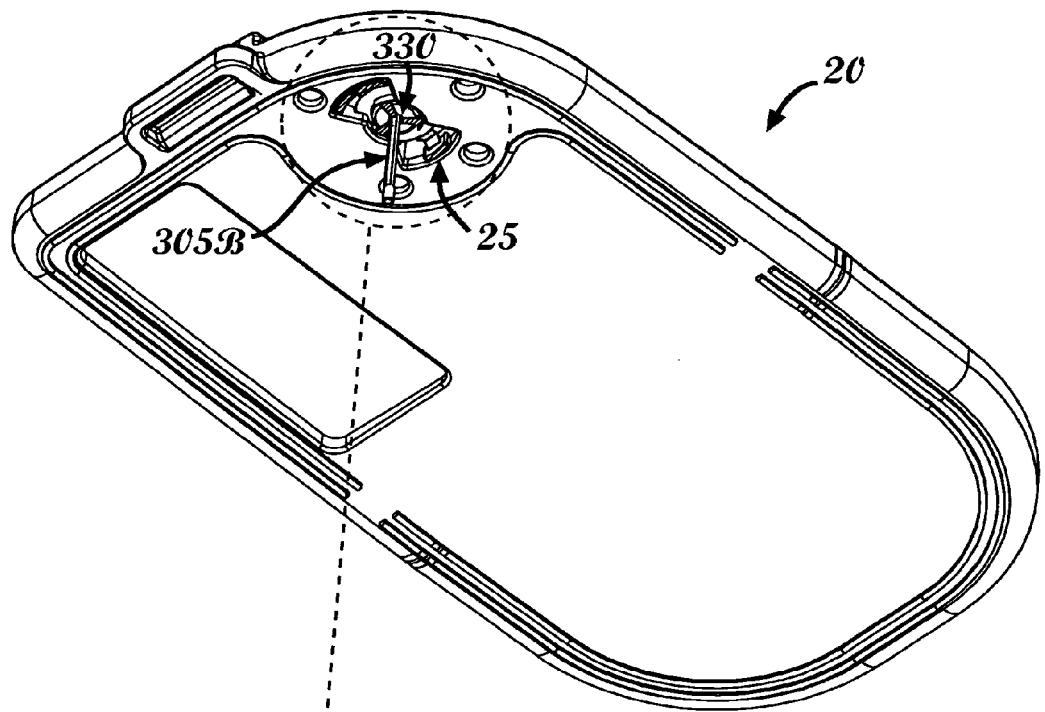
FIGS. 39a-b shows a bottom view of the tip and the cradle after tip insertion according to some embodiments of the disclosure.
Figure 39B:
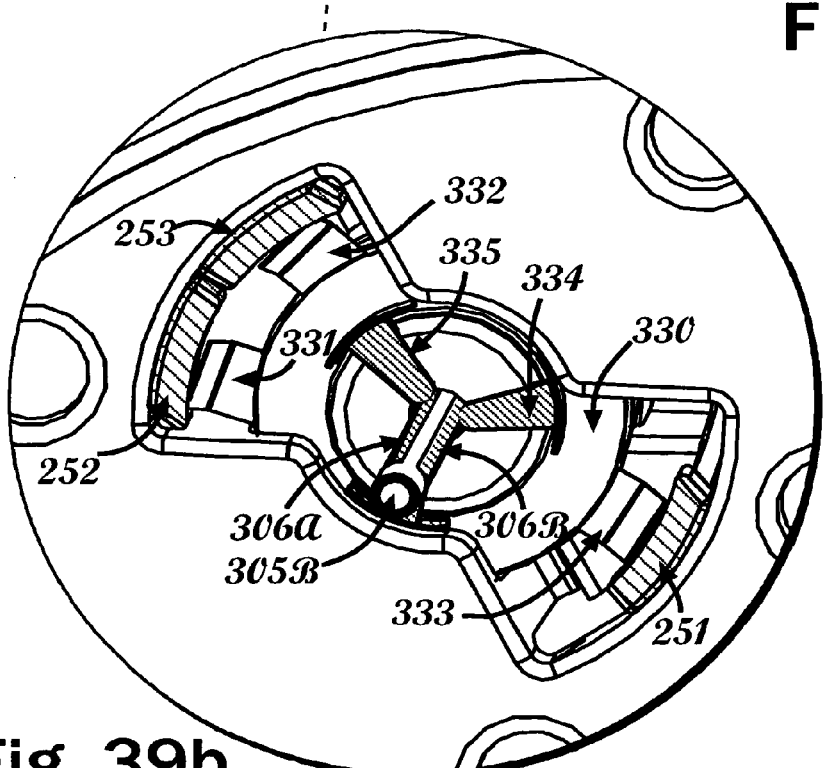

FIG. 38 shows the tip 300 before connection to the cradle 20. Connectors (e.g., three connectors) 251, 252, and 253 ("well connectors") may be provided at the bottom of the side walls of the well for contacting cradle connectors 331, 332, 333 of the connectors-plate 330. In some embodiments, two of the well connectors 252, 253 may be provided on one side wall of the well and the third connector 251 may be provided on the opposite wall. Accordingly, two of the cradle connectors 332, 333 may be located on one side of the connectors-plate and the third cradle connector 331 may be located on another side (e.g., across). The cradle connectors 331, 332, 333 may be resilient to ensure contact with the well connectors 251, 252, 253 after tip insertion. FIGS. 39a-b show a bottom view of the tip 300 (having the cannula 305b) and the cradle 20 after connection, including the connectors-plate 330 that comprises three (3) electrodes connectors 334, 335, (336 not shown) and three (3) cradle connectors 331, 332, and 333, for example.

Figure 40:
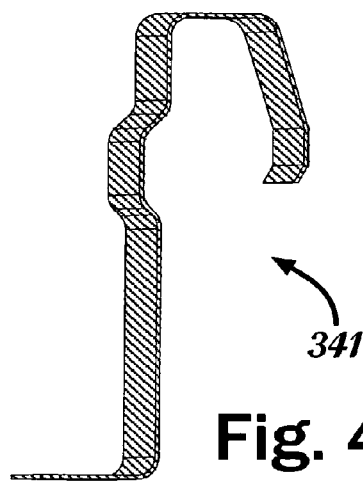
FIG. 40 shows a folded electrode according to some embodiments of the disclosure.
Figure 41:
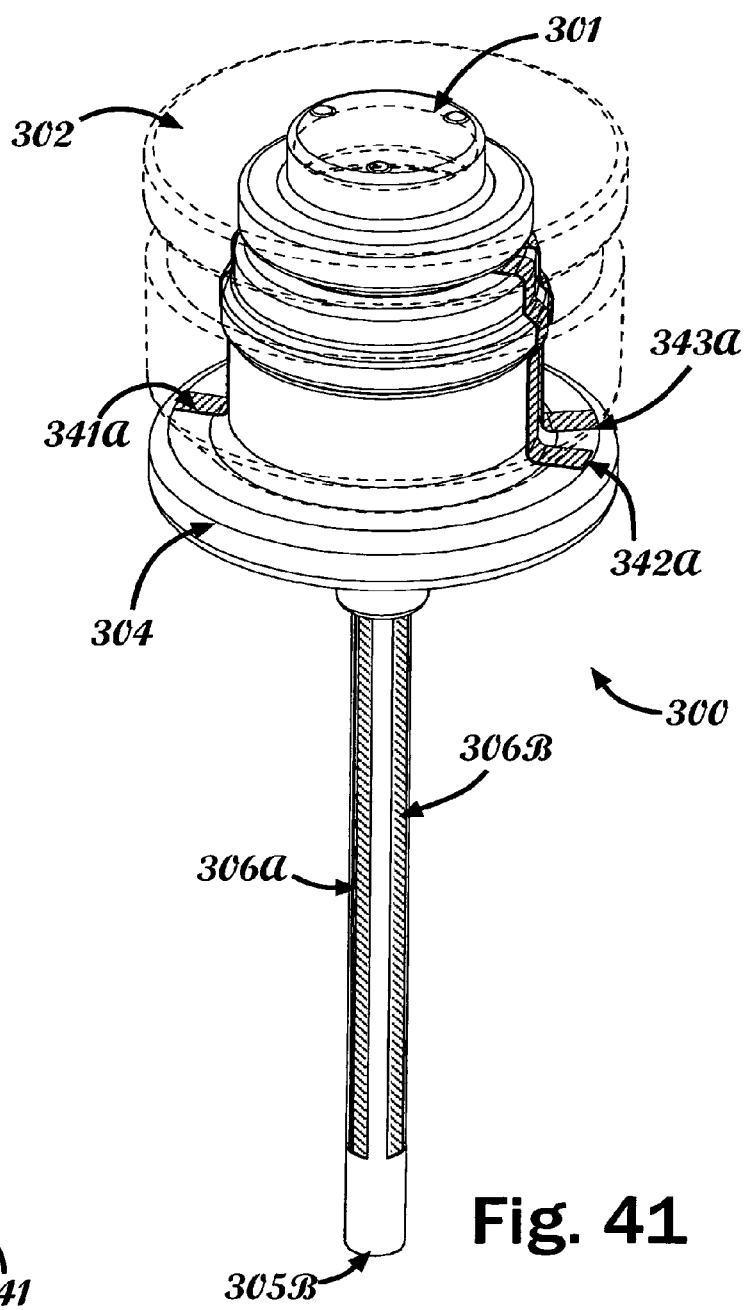
FIG. 41 shows a tip that comprises folded electrodes according to some embodiments of the disclosure.

FIGS. 40-43b illustrate an example of a tip having a multi-lumen cannula according to the configuration shown schematically in FIG. 12d, for example. In this example, the multi-lumen cannula includes one central lumen for fluid delivery and, for example, three (3) circumferential lumens each providing an electrode. According to some embodiments of the current configuration, the electrical connecting wires are inserted to the lumens within the cannula through the bushing and the inner side of the cannula housing and they are folded around outer surface of cannula housing. An example of such a folded wire 341 is illustrated in FIG. 40. The three (3) connectors 341a, 342a, 343a of the three (3) electrodes may be provided by a recess (e.g., an annular recess) formed between the cannula housing 304 and the cover 302, as illustrated in FIG. 41. In some embodiments, the wires may be integrally formed with the electrodes and/or with the connectors, forming a single continuous element.

Figure 42:
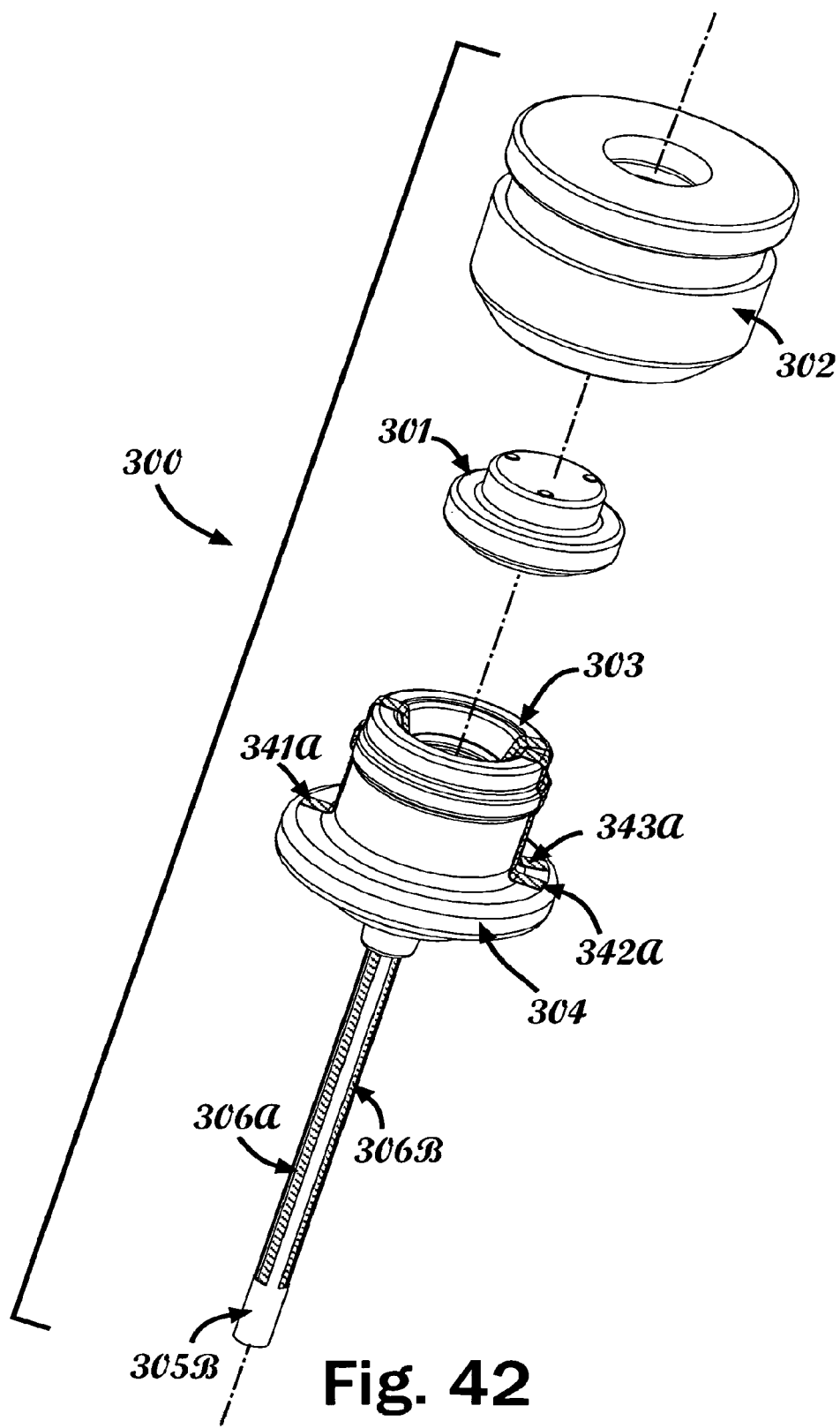
FIG. 42 shows tip components including the folded electrodes before assembly according to some embodiments of the disclosure.

FIG. 42 shows an exploded view of tip 300 implementing cannula 305b and three (3) electrodes including folded wire connected to connectors 341a, 342a, and 343a, respectively. The electrodes wires may be folded from the inner portion of the cannula housing toward its external side, such that the connectors 341a, 342a, and 343a are located on the external side of the cannula housing 304 in a recess (e.g., an annular recess) formed between the cannula housing 304 and the cover 302. The self-sealable septum 301 and the cover 302 may be placed on top of the cannula housing 304 such that the septum is received in an aperture on the upper portion of the cover.

FIGS. 43a-b show the tip illustrated in FIG. 42 and the cradle before connection. FIG. 43b shows a magnified bottom view of the tip 300 and the well 25 during insertion process, before they are connected to one another. In some embodiments, two connectors 252, 253 may be provided on one protrusion 24b and one connector 251 may be provided on a second protrusion 24a. Respectively, two connectors 342, 343 may be provided on an opposite side to the third connector 341 within the recess of the tip 300, such that after tip 300 insertion through the well 25 the tip connectors 341, 342, and 343 contact the cradle connectors 251, 252, and 253.

FIGS. 44a-48b illustrate an example of a configuration of current transfer structure within a cradle, according to some embodiments. In this configuration, electrical wires and connectors are located on or within the adhesive layer placed at the bottom of the cradle.

Figure 44A:
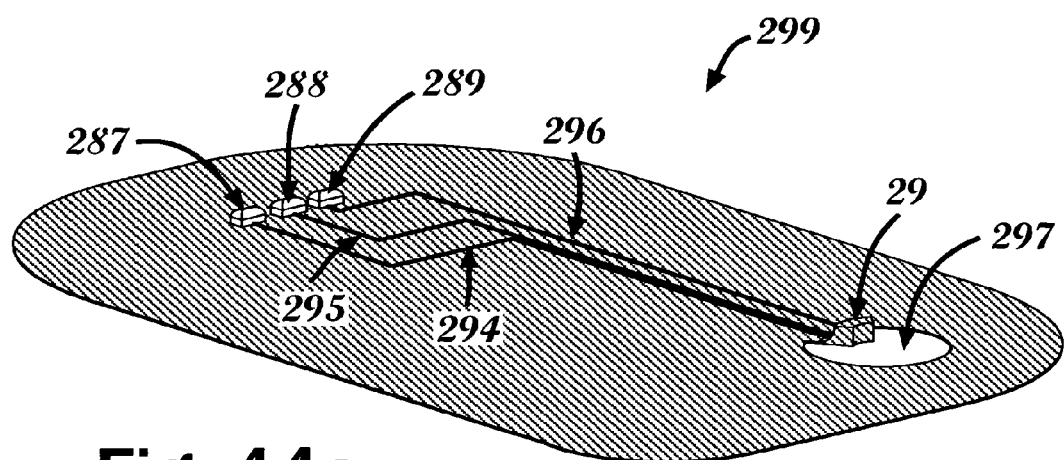
FIGS. 44a-b show a conductive adhesive tape before attachment to the cradle according to some embodiments of the disclosure.
Figure 44B:
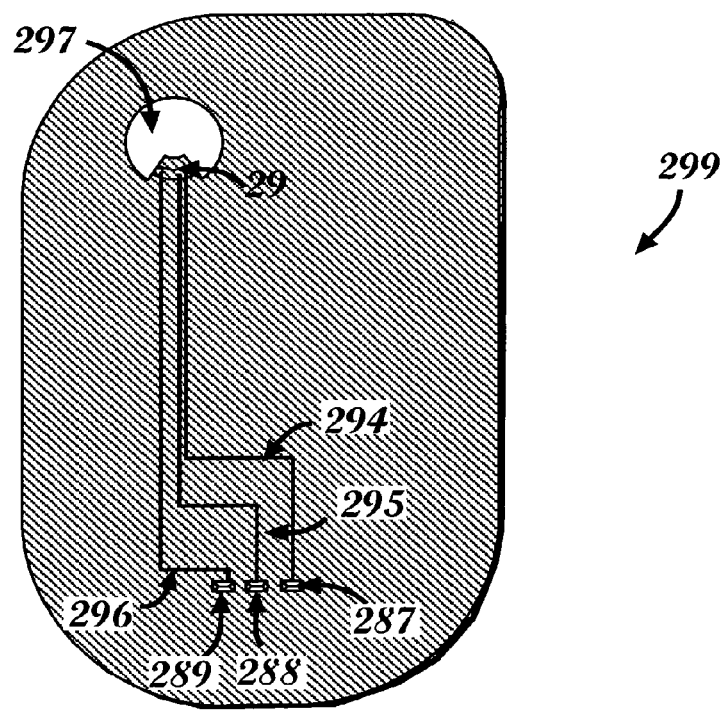

Accordingly, FIGS. 44a-b illustrate an adhesive layer 299, which may include an opening 297 aligned with an opening of the cradle providing a passageway for tip insertion into the body of the patient through the cradle and the adhesive layer. In some embodiments, one or more tip connectors 29 may be provided at or adjacent the opening 297 of the adhesive layer 299. For example, the tip connectors 29 may be located on a protruded portion of the adhesive layer 299 configured to be received within the cradle's opening. The one or more tip connectors 29 may come in contact (e.g., mechanical. physical) with one or more connectors provided one the tip when the tip is inserted through the cradle and the adhesive layer. The one or more tip connectors 29 may be connected via one or more wires (e.g., 294, 295, and 296) to one or more patch connectors (e.g., 287, 288, and 289). The one or more patch connectors may be configured to establish electrical communication with connector placed on the patch, when the patch is connected to the cradle.

Figure 45:
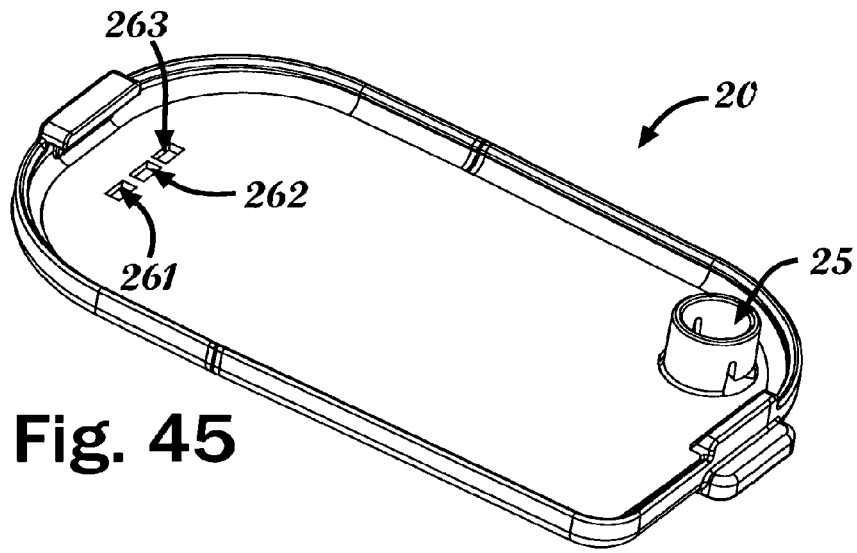
FIG. 45 shows a cradle that comprises a well opening and one or more connector's openings according to some embodiments of the disclosure.

FIG. 45 shows a top view of the cradle 20, before attachment of the adhesive layer to the cradle 20 and before insertion of a tip. The cradle may include an opening (e.g., a well) 25 configured to receive any of the tip's configurations described herein. The cradle 20 may further include one or more openings (e.g., 261, 262, 263) configured to receive the one or more patch connectors located on the adhesive layer enabling contact surface with connectors located at the bottom side of a patch upon connection therebetween. In some embodiments, a miniature amplifier may be located (at least in part) on the adhesive layer 299 for strengthening signals generated by the electrodes, and the adhesive layer may also include a power source enabling continuous operation of the electrodes, for example.

Figure 46A:
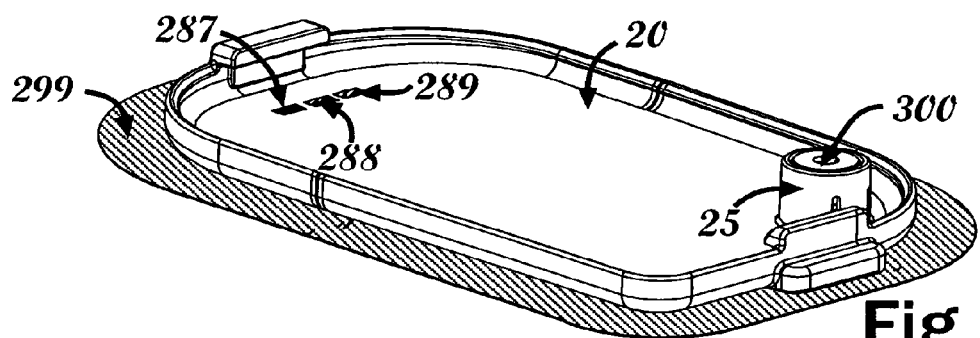
FIGS. 46a-b show the cradle after attachment to the conductive adhesive tape and after tip insertion through the well opening according to some embodiments of the disclosure.
Figure 46B:
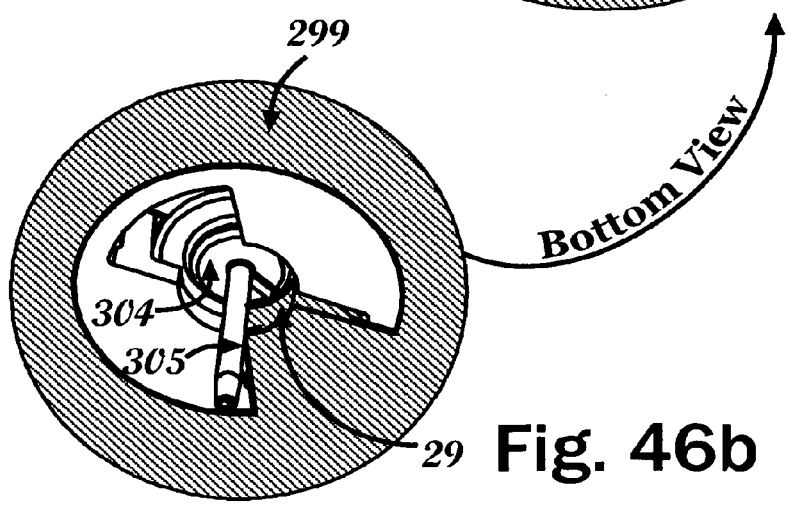

FIGS. 46a-b illustrate the cradle 20 depicted in FIG. 45, after attachment of the adhesive layer 299 to the cradle and after tip 300 insertion through the well 25. As illustrated in FIG. 46a, the one or more patch connectors 287, 288, and 289 protrude through the cradle openings providing contact pads on the surface of the cradle. The connectors 287, 288, and 289 may be configured such that they remain sealed when the patch is disconnected from the cradle. In some embodiments a sealing cap may be provided to cover the connectors 287, 288, and 289 when the patch unit is disconnected from the cradle. FIG. 46b shows a magnified bottom view of well 25 and adhesive layer 299 after insertion of the tip through the well opening. Upon insertion of the tip through the well opening the one or more tip connectors 29 may come in contact with a probe and/or electrodes and/or connectors located within the tip. The well 25 and/or the tip may be configured such that upon connection of the tip to the well 25, the connectors remain sealed.

Figure 47A:
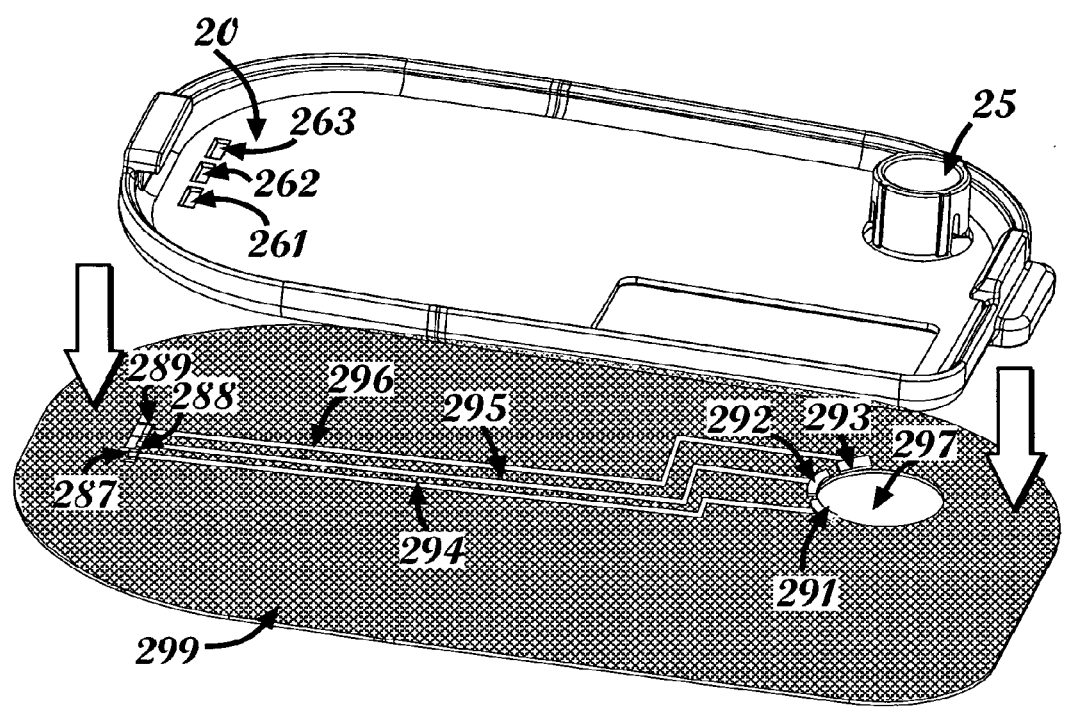
FIGS. 47a-b show the cradle before (47a) and after (47b) attachment to the conductive adhesive tape according to some embodiments of the disclosure.
Figure 47B:
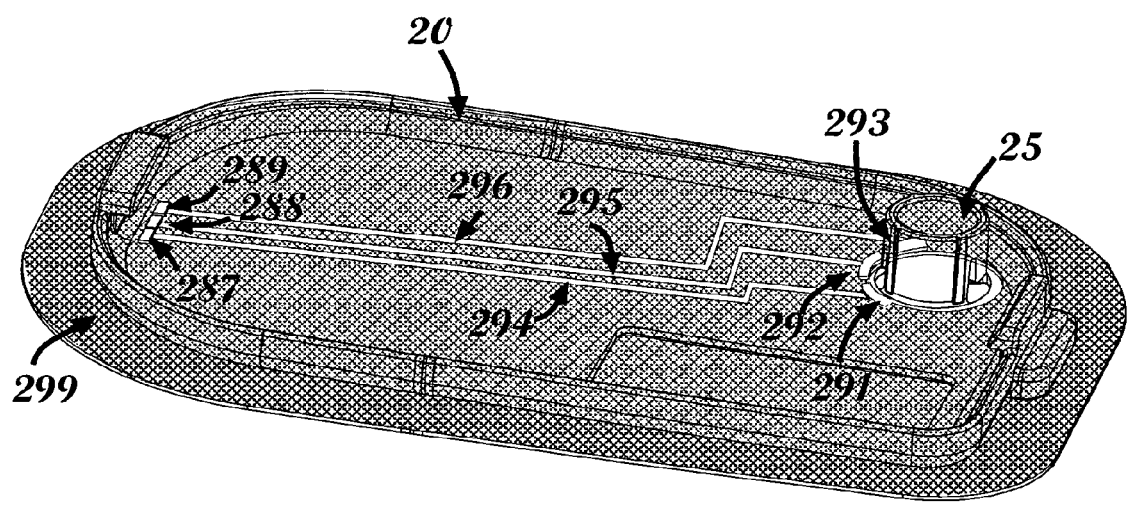

FIGS. 47a-b illustrate a specific example of the cradle 20 including three (3) tip connectors 291,292,293 located at the opening 297 of the adhesive layer 299. The adhesive layer further includes three (3) electrical wires 294,295,296 and three (3) patch connectors 287,288,289. FIG. 47a illustrates the adhesive and cradle prior their attachment, and FIG. 47b illustrates the cradle with the adhesive layer attached thereto.

FIGS. 48a-b illustrate the connection of the tip 300, the cradle 20 and the conductive adhesive layer 299. As illustrated in FIG. 48b (magnified view), connectors 320a, 320b, and 320c (also illustrated schematically in FIG. 12a, for example) are configured for coming in contact with the one or more tip connectors 29 upon insertion of the tip through the well 25 and the adhesive layer opening 297.

FIGS. 49a-52 illustrate examples of a tip cartridge (maybe also referred-to as "cannula cartridge") and an inserter. The cannula cartridge may be configured to receive a tip, as described in the various embodiments herein, and to be loaded onto the inserter. The cannula cartridge may include a penetrating member aiding in the insertion of the tip. The inserter may include a spring loaded mechanism for firing the penetrating member and the tip into a body of a patient. Upon operation of the inserter, the penetrating member and the tip are being fired from cannula cartridge into the body, and immediately after the insertion of the tip to the body the penetrating member is retracted into the cannula cartridge to avoid self-pricking. In some embodiments, during the insertion process the tip may be connected to a cradle secured to the body. The cannula cartridge (including the penetrating member) may be disconnected from the inserter and disposed.

Figure 49A:
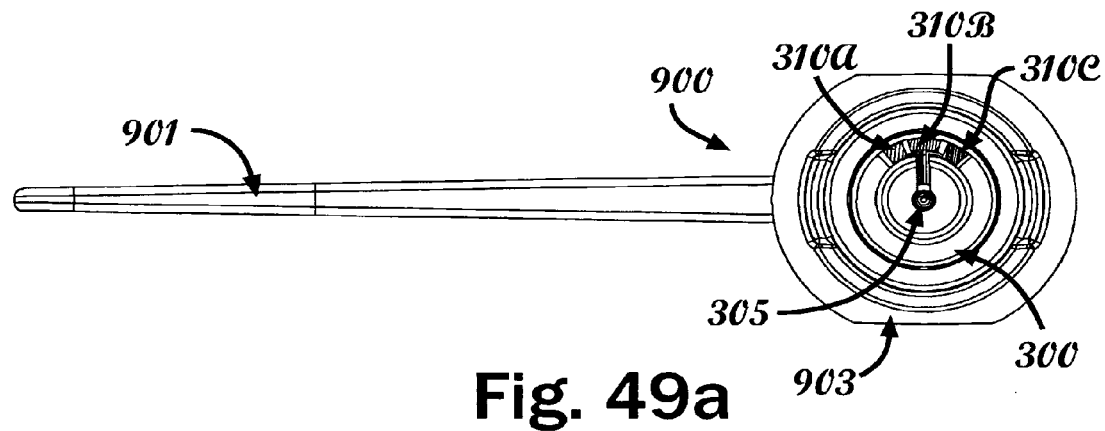
FIGS. 49a-b show bottom cross sectional view (49a) and spatial view (49b) of a cannula cartridge according to some embodiments of the disclosure.
Figure 49B:
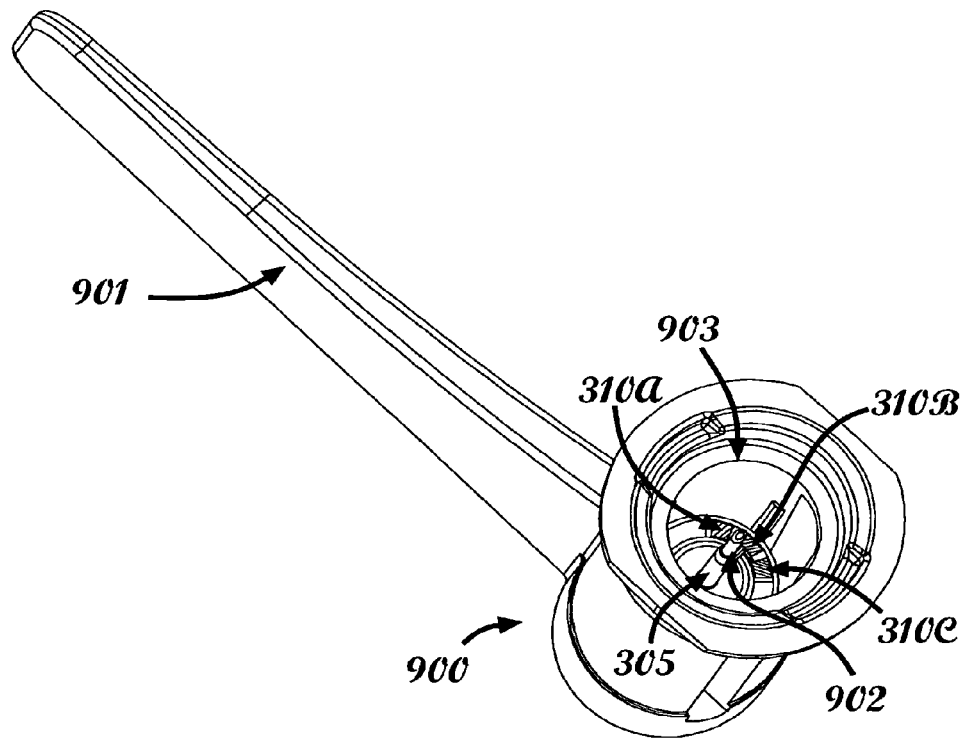

Accordingly, FIGS. 49a-b show a bottom cross sectional view (FIG. 49a) and a bottom spatial view (FIG. 49b) of a cannula cartridge 900. The cannula cartridge may include a body 903 and a handle 901. The tip 300 may be located within the cartridge body 903 (which may also be referred to as a housing) and comprise cannula 305 (or any other cannula such as for example 305a, 305b depicted above). Cannula 305 includes electrodes and connectors, for example connectors 310a, 310b, and 310c. The cannula 305 may include a first lumen for delivering fluids and one or more second lumens providing the electrodes. A needle 902 of the penetrating member is inserted longitudinally through a lumen within the cannula 305 for insertion of the cannula 305 to the body. Providing the electrodes by lumens within the cannula 305 omits the necessity of an outer penetrating member protecting the electrodes and enabling the use of an inner penetrating member for decreasing the penetrating area of the tip. In some embodiments, the perimeter of the cannula 305 having the electrodes is intact comparable with a cannula configuration which only delivers fluids. In some embodiments, the perimeter of the cannula 305 may be about 1.8 mm.

FIGS. 50a-e illustrate an assembly of tip 300, penetrating member 902, and cannula cartridge 900. FIG. 50a shows the tip 300 and the penetrating member 902 before connection. The tip 300 comprises a septum 301, a cover 302, a cannula housing 304 and a cannula 305 (for example) having electrodes and connectors. The penetrating member comprises the needle 902 and a needle cover 908. In some embodiments, a tooth/a protrusion/a latch 905 may be provided at the bottom of the needle cover 908 (as shown in FIG. 50c) and a corresponding groove 906 may be provided in the cover 302 of the tip (as shown in FIG. 50b) for aligning and coupling the needle cover 908 with the tip. In some embodiments, one or more grooves 904 may be provided in the needle cover 908 (as shown in FIG. 50a) and one or more protrusions 907 may be provided on cannula cartridge body 903 (as shown in FIG. 50d) for aligning (and coupling) the needle cover 908 with the cartridge (as shown in FIG. 50e). The one or more grooves 904 may be configured as tracks enabling movement of the needle cover 908 for insertion of the tip to the body of the patient while being aligned with the cannula cartridge. The alignment between the tip 300, the penetrating member 902 and the cartridge 900 achieves precision in locating the tip within the well of the cradle and for ensuring proper contact of the electrodes connectors and the well connectors.

Figure 51:
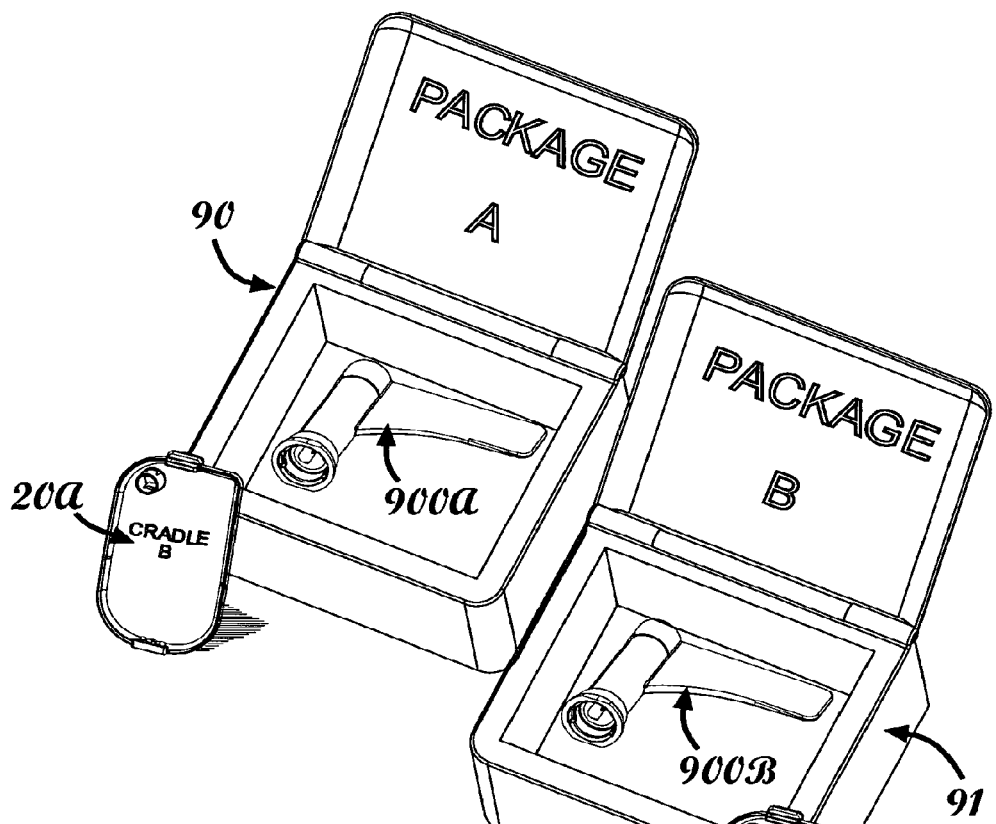
FIG. 51 shows an example package of the cannula cartridge and the cradle according to some embodiments of the disclosure.
Figure 52:
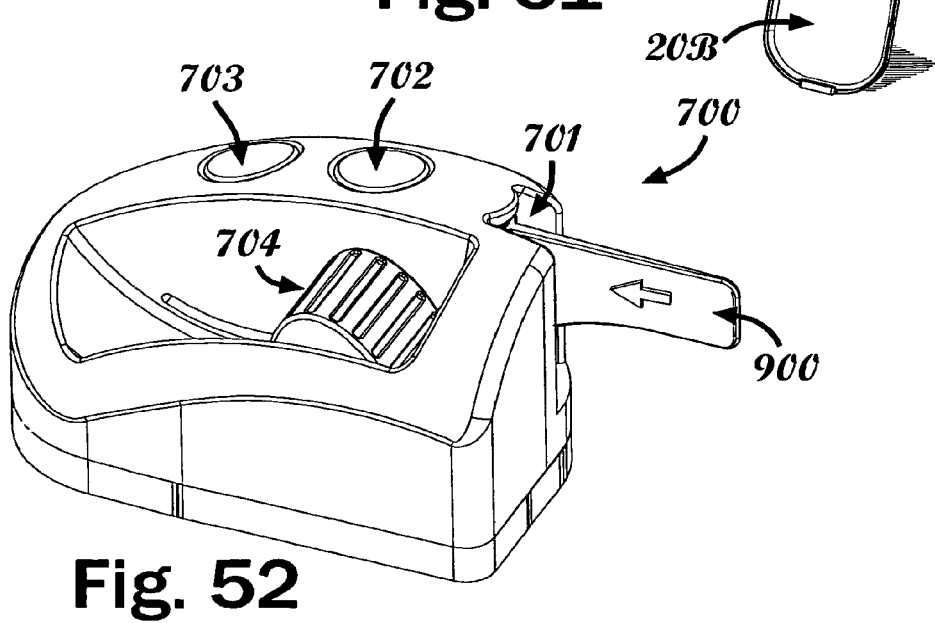
FIG. 52 shows the cannula cartridge loaded onto an inserter according to some embodiments of the disclosure.

FIG. 51 shows an example of packaging of a cannula cartridge and cradle of a sensing and dispensing device 90 and a dispensing only device 91. In the sensing/dispensing device, the cannula cartridge 900a includes a tip that comprises electrodes, wires and connectors and the cradle 20a comprises connectors and wires. In the dispensing only device, the cartridge 900b comprises a tip that includes only a fluid dispensing cannula and a cradle 20b that has no wires and connectors. In some embodiments, cartridge 900a and cartridge 900b may have similar physical dimensions (e.g., height, length). In some embodiments, cradle 20a and cradle 20b may also have similar physical dimensions.

FIG. 52 shows a cannula cartridge 900 loaded onto an inserter 700. The inserter comprises a slot 701 to accommodate the cannula cartridge, a winding means 704 and operating/triggering buttons 702, and 703. After firing the tip, the cartridge (including the needle of the penetrating member) can be disconnected from the inserter and disposed of.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, the logic flows depicted in the accompanying figures and described herein do not require the particular order shown, or sequential order, to achieve desirable results.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the exemplary claims. Other aspects, advantages, and modifications are considered to be within the scope of the following exemplary claims. The exemplary claims presented are representative of only some of the embodiments and features disclosed herein. Other unclaimed embodiments, inventions, and features are also contemplated.

What is claimed is:

1. A skin securable medical device comprising:
a tip configured for insertion and for delivering therapeutic fluid into the body of a patient;
a pump for delivering the therapeutic fluid into the body of the patient via the tip;
a sensor provided at the tip and configured for sensing a level of one or more analytes within the body of the patient and configured for providing at least one sensor signal indicative of the level of one or more sensed analytes;
a processor housed within a patch unit for processing the at least one sensor signal and for controlling the therapeutic fluid delivery;
at least one first connector provided on the tip for enabling an electrical communication between the sensor and the processor; and
an adherable housing portion comprising a cradle for securing at least part of the device to the skin of the patient, the adherable housing portion including a well for receiving the tip within an opening, and at least one second connector located on at least one protrusion extending laterally inward within the opening of the well;
wherein:
upon insertion of the tip through the well, the at least one first connector is coupled to the at least one second connector establishing the electrical communication therebetween and enabling transfer of the at least one sensor signal from sensor to the processor; and
the patch unit comprises at least one third connector extending away from the underside of the patch unit, and electrical currents are also sent to the processor from the well when the at least one third connector of the patch unit is pressed against a conductive protrusion extending upward and away from the cradle toward the patch unit, the pressing causing contacting pads in the conductive protrusion to contact wires extending from the well to the conductive protrusion.

2. The device according to claim 1, wherein the cradle includes at least one latch for connecting the cradle and the patch unit.

3. The device according to claim 2, wherein the cradle includes a power source enabling continuous or periodic operation of the electrodes or probe.

4. The device according to claim 3, wherein the continuous or periodic operation of the electrodes or probe occurs when the pump is disconnected.

5. The device according to claim 2 wherein the cradle includes an amplifier for amplifying the signals conveyed from the sensor.

6. The device according to claim 1, wherein the tip includes a first lumen for delivering the therapeutic fluid and one or more second lumens for providing at least a portion of the sensor.

7. The device, according to claim 6, wherein the one or more second lumens includes three lumens.

8. The device according to claim 6, wherein the one or more second lumens includes one or more windows enabling exposure of at least a portion of the sensor to the surrounding.

9. The device according to claim 6, wherein the one or more second lumens is substantially shorter than the first lumen.

10. The device according to claim 6, wherein the first lumen has a substantially circular cross section and the one or more second lumens has a substantially arched cross section.

11. The device according to claim 1, wherein the sensor comprises a plurality of electrodes for sensing the level of one or more analytes.

12. The device according to claim 11, wherein each electrode resides in a separate one or more second lumens of the tip.

13. The device according to claim 1, wherein the tip comprises a cannula for delivering the therapeutic fluid therethrough.

14. The device of claim 1 wherein the conductive protrusion is configured to remain sealed by a sealed cap when the patch unit is disconnected from the cradle.

15. The device according to claim 1, wherein at least a portion of the sensor is bent for enabling physical contact between the at least one first and second connectors upon insertion of the tip through the well.

16. The device according to claim 1, wherein the device operates in a mode selected from the group consisting of: a closed loop mode, a semi-closed loop mode, and an open loop mode.

17. The device according to claim 1, wherein the adherable housing portion comprises a latch including the at least one second connector for establishing the electrical communication with the at least one first connector.

18. The device according to claim 1, wherein the well is configured to enable tip insertion in an angle with respect to the adherable housing portion.

19. The device according to claim 1, further comprising:
a cannula cartridge unit;
a penetrating member for piercing the skin of the patient during insertion of the tip;
and an inserter;
wherein the cannula cartridge unit and the penetrating member are configured to align the tip, such that upon insertion of the tip through the well of the adherable housing portion, the at least one first connector contacts the at least one second connector.

20. The device according to claim 1, wherein the adherable housing portion includes an adhesive tape, the adhesive tape having at least one connector and at least one wire.

* * * * *